(12) United States Patent
Hosen et al.

(10) Patent No.: US 10,988,540 B2
(45) Date of Patent: *Apr. 27, 2021

(54) ANTIBODY

(71) Applicant: OSAKA UNIVERSITY, Suita (JP)

(72) Inventors: Naoki Hosen, Suita (JP); Haruo Sugiyama, Suita (JP); Atsushi Kumanogoh, Suita (JP); Junichi Takagi, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/905,211

(22) Filed: Jun. 18, 2020

(65) Prior Publication Data

US 2020/0385474 A1  Dec. 10, 2020

Related U.S. Application Data

(63) Continuation of application No. 16/808,451, filed on Mar. 4, 2020, which is a continuation of application No. 15/751,574, filed as application No. PCT/JP2016/072688 on Aug. 2, 2016, now Pat. No. 10,654,931.

(30) Foreign Application Priority Data

Aug. 11, 2015 (JP) ................ 2015-159240

(51) Int. Cl.
| | | |
|---|---|---|
| C07K 16/00 | (2006.01) | |
| C07K 16/46 | (2006.01) | |
| C07K 16/28 | (2006.01) | |
| A61K 35/17 | (2015.01) | |
| C12N 5/10 | (2006.01) | |
| C12N 15/09 | (2006.01) | |
| A61K 39/00 | (2006.01) | |
| C07K 19/00 | (2006.01) | |
| A61P 35/00 | (2006.01) | |
| C07K 16/30 | (2006.01) | |

(52) U.S. Cl.
CPC .......... C07K 16/2839 (2013.01); A61K 35/17 (2013.01); A61K 39/0011 (2013.01); A61P 35/00 (2018.01); C07K 19/00 (2013.01); C12N 5/10 (2013.01); C12N 15/09 (2013.01); A61K 2039/505 (2013.01); A61K 2039/5156 (2013.01); A61K 2039/5158 (2013.01); C07K 16/30 (2013.01); C07K 2317/34 (2013.01); C07K 2317/565 (2013.01); C07K 2317/622 (2013.01); C07K 2317/73 (2013.01); C07K 2317/92 (2013.01); C07K 2319/03 (2013.01); C07K 2319/33 (2013.01)

(58) Field of Classification Search
None
See application file for complete search history.

(56) References Cited

U.S. PATENT DOCUMENTS

| | | | | |
|---|---|---|---|---|
| 10,654,931 | B2 * | 5/2020 | Hosen ................ | A61K 39/0011 |
| 2012/0045446 | A1 | 2/2012 | Hosen et al. | |

FOREIGN PATENT DOCUMENTS

| | | | |
|---|---|---|---|
| CN | 1195374 | A | 10/1998 |
| CN | 103374073 | A | 10/2013 |
| JP | 06-086688 | A | 3/1994 |
| JP | 06-303990 | A | 11/1994 |
| JP | 2001-507210 | A | 6/2001 |
| JP | 2003-508355 | A | 3/2003 |
| JP | 2009-534401 | A | 9/2009 |
| JP | 2011-527572 | A | 11/2011 |
| JP | 2015-513394 | A | 5/2014 |
| WO | 97/39124 | A1 | 10/1997 |
| WO | 98/006248 | A2 | 2/1998 |
| WO | 01/12674 | A1 | 2/2001 |
| WO | 2007/124299 | A2 | 11/2007 |
| WO | 2010/005570 | A2 | 1/2010 |
| WO | 2010/107752 | A2 | 9/2010 |
| WO | 2010/117059 | A1 | 10/2010 |
| WO | 2013/123061 | A1 | 8/2013 |
| WO | 2014/160753 | A1 | 10/2014 |
| WO | 2015/013671 | A1 | 1/2015 |

OTHER PUBLICATIONS

Hosen et al. The activated conformation of integrin β7 is a novel multiple myeloma—specific target for CAR T cell therapy. Nat Med. Dec. 2017;23(12):1436-1443 (Year: 2017).*
Krissansen et al., Immunologic and structural relatedness of the integrinP,complex and the human intraepithelial lymphocyte antigen MML-1. FEES Lett. Jan. 13, 1992; 296(1):25-8 (Year: 1992).
Campbell A, General properties and applications of monoclonal antibodies, Elsevier Science Publishers, section 1.1, pp. 1-32, 1984. (Year: 1984).
Zhao et al., A Herceptin-Based Chimeric Antigen Receptor with Modified Signaling Domains Leads to Enhanced Survival of Transduced T Lymphocytes and Antitumor Activity, J Immunol. Nov. 1, 2009; 183(9): 5563-74 (Year: 2009).
Parker et al., A family of U7 integrins on human mucosal lymphocytes, Proc. Nadi. Acad. Sci. USA vol. 89, pp. 1924-1928, Mar. 1992 (Year: 1992).
Dulce Soler-Ferran, et al., "Integrin a4ß7 Antagonists: Activities, Mechanisms of Action and Therapeutic Prospects", Current Immunology Reviews, 2012, vol. 8, No. 2, pp. 118-134 (total 17 pages).
Asima Khan, "Production of a monoclonal antibody against the alpha 4 beta 7 integrin", San Jose State University, SJSU Scholar Works, Master's Thesis, Aug. 2009, URL:https://scholarworks.sjsu.edu/cgi/viewcontent.cgi?referer=https://scholar.google.com/&httpsredir=1&article=4690&context=etd_theses [retrieved on Dec. 12, 2018], pp. 1-74 (total 74 pages).

(Continued)

*Primary Examiner* — Maher M Haddad
(74) *Attorney, Agent, or Firm* — Sughrue Mion, PLLC

(57) ABSTRACT

Provided is an active ingredient of a pharmaceutical composition for treating myeloma. Specifically, provided is an antibody whose epitope is present in the region of the amino acid residue positions 20 to 109 of human integrin $\beta_7$.

12 Claims, 30 Drawing Sheets

Specification includes a Sequence Listing.

(56) References Cited

OTHER PUBLICATIONS

Davila et al., "Chimeric antigen receptors for the adoptive T cell therapy of hematologic malignancies", International Journal of Hematology, 2013, vol. 99, No. 4, pp. 361-371 (total 11 pages).
Kilger et al., "Differential Regulation of a4 Integrin-dependent Binding to Domains 1 and 4 of Vascular Cell Adhesion Molecule-1", The Journal of Biological Chemistry, 1995, vol. 270, No. 11, pp. 5979-5984 (total 6 pages).
Communication dated Jan. 2, 2019 from the European Patent Office in counterpart European Application No. 16835028.8.
Mark Tidswell, et al., "Structure-Function Analysis of the Integrin ß7 Subunit: Identification of Domains Involved in Adhesion to MAdCAM-1", Journal of Immunology, 1997, pp. 1497-1505, vol. 159, No. 3.
Anti-Integrin beta 7 antibody [EP5948] (ab137058), abcam [online], submitted Aug. 22, 2013, [retrieved Oct. 18, 2016], Retrieved from the Internet: <URL: http://www.abcam.com/integrin-beta-7-antibody-ep5948-ab137058.html>, 4 pages.
Geoffrey W. Krissansen, et al., "Immunologic and structural relatedness of the integrin ß7complex and the human intraepithelial lymphocyte antigen HML-1", FEBS Letters, Jan. 1992, pp. 25-28, vol. 296, No. 1.
Tetsuya Goto, et al., "A Novel Membrane Antigen Selectively Expressed on Terminally Differentiated Human B Cells", Blood, Sep. 15, 1994, pp. 1922-1930, vol. 84, No. 6.
Sagar Lonial, et al., "Elotuzumab in Combination With Lenalidomide and Low-Dose Dexamethasone in Relapsed or Refractory Multiple Myeloma", Journal of Clinical Oncology, Jun. 1, 2012, pp. 1953-1958, vol. 30, No. 16.
Michel De Weers, et al., "Daratumumab, a Novel Therapeutic Human CD38 Monoclonal Antibody, Induces Killing of Multiple Myeloma and Other Hematological Tumors", The Journal of Immunology, Feb. 1, 2011, pp. 1840-1848, vol. 186, No. 3.
Junpeng Qi, et al., "Identification, Characterization, and Epitope Mapping of Human Monoclonal Antibody J19 That Specifically Recognizes Activated Integrin a4ß7", The Journal of Biological Chemistry, May 4, 2012, pp. 15749-15759, vol. 287, No. 19.
Yangbing Zhao, et al., "A Herceptin-Based Chimeric Antigen Receptor with Modified Signaling Domains Leads to Enhanced Survival of Transduced T Lymphocytes and Antitumor Activity", The Journal of Immunology, Nov. 1, 2009, pp. 5563-5574, vol. 183, No. 9.
Shannon L. Maude, M.D., Ph.D., et al., "Chimeric Antigen Receptor T Cells for Sustained Remissions in Leukemia", The New England Journal of Medicine, Oct. 16, 2014, pp. 1507-1517, vol. 371, No. 16.
John Maher, et al., "Human T-lymphocyte cytotoxicity and proliferation directed by a single chimeric TCR? /CD28 receptor", Nature Biotechnology, Jan. 2002, pp. 70-75, vol. 20, No. 1.
Bjorn Forsstrom, et al., "Dissecting Antibodies with Regards to Linear and Conformational Epitopes", PLoS One, DOI:10.1371/journal.pone.0121673, Mar. 27, 2015, 11 pages, vol. 10, No. 3.
Greg A. Lazar, et al., "Engineered antibody Fc variants with enhanced effector function", PNAS, Mar. 14, 2006, pp. 4005-4010, vol. 103, No. 11.
Robert L. Shields, et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, Mar. 2, 2001, pp. 6591-6604, vol. 276, No. 9.
Michael S. Cole, et al., "Human IgG2 Variants of Chimeric Anti-CD3 Are Nonmitogenic to T Cells", The Journal of Immunology, 1997, pp. 3613-3621, Vo. 159.
Zhiqiang An, et al., "IgG2m4, an engineered antibody isotype with reduced Fc function", mAbs, Dec. 2009, pp. 572-579, vol. 1, No. 6.
International Search Report for PCT/JP2016/072688 dated Nov. 1, 2016 [PCT/ISA/210].
Jinli, Li, "High Affinity Human Monoclonal Antibody to Integrin Alpha4 Beta7 Screening and Functional Testing," Dissertation Submitted to the Graduate School of Henan Normal University in Partial Fulfillment of the Requirements for the Degree of Master of Science, May, 2014, pp. 1-49 English Translation.

\* cited by examiner

Alignment: human vs. mouse β7 integrin

```
human b7    1:mvalpmvlvlllvlsrgesELDAKIPSTGDATEWRNPHLSMGSCQPAPSCQKCILSHPSCAWCQLNFTASGEAEARRCARREILLARG  90
mouse b7    1:mvdsstvlifilvlgggsELDTKIMSSCEAEWEDPDLSLQSSCQPVPSCQKCILSHPSCAWCQLNFTASGEAEARRCARREILLARG  90
                 * *  ** *    ****.*. .* .* *  .**  *:************************************** human b7   91:CPLEELEEPRGQQEVLQDQPLSQGARGEGATQLAPQRVRVTLRPGEPQQLQVRFLRAEGYPVDLYYLMDLSYSMKDDLERVRQLGHALLV 180
mouse b7   91:CPAQELEEPRGRQEVLQDKPLSQGDRGEGATQLAPQRIRVTLRPGEPQRFRVRFLRAAGYPVDLYYLMDLSYSMKDDLERVRQLGHALLV 180
               :*** :*:.*********:******: :** ***************************** human b7  181:RLQEVTHSVRIGFGSFVDKTVLPFVSTVPSKLRHPCPTRLERCQSPFSFHHVLSLTGDAQAFEREVGRQSVSGNLDSPEGGFDAILQAAL 270
mouse b7  181:RLQEVTHSVRIGFGSFVDKTVLPFVSTVPSKLRHPCPSRLERCQPPFSFHHVLSLTGDAQAFEREVGRQNVSGNLDSPEGGFDAILQAAL 270
              ***********************************:**.******************* ***************** human b7  271:CQEQIGWRNVSRLLVFTSDDTFHTAGDGKLGGIFMPSDGHCHLDSNGLYSRSTEFDYPSVGQVAQALSAANIQPIFAVTSAALPVYQELS 360
mouse b7  271:CQEQIGWRNVSRLLVFTSDDTFHTAGDGRCHLDSNGVTINSAEFDYPSVGQVAQALTAANIQPIFAVIGATLPVYQELR 360
              *****************************               * * * *   **************** .* ****** :

human b7  361:KLIPKSAVGELSEDSSNVVQLIMDAYNSLSSTVTLEHSSLPPGVHISYESQCEEGPEKREGKAEDRGQCNHVRINQTVTFWVSLQATHCLP 450
mouse b7  361:QLIPKSAVGELSEDSSNVVQLIMDAYDSLSSTVTLEHSPLPPGVSISFESHCKGPEKTEGEAGDRGQCNDVRVNQTVDFWVTLQATHCLP 450
              :*************************:***********.***** **:**:*: **** **.* ****** ** **** ***:******
```

From FIG. 24A

```
human b7  451:EPHLLRLRALGFSEELIVELHILCDCMCSDTQPQAPHCSDGQGHLQCGVCSCAPGRLGRLCECSVAELSSPDLESGCRAPNGTGPLCSGK 540
mouse b7  451:EAHVLRLWALGFSEETIVELHTVCDCNCGDAQPHAPYCSDGQSDLQCGICSCAPGRLGQLCRCSEADLSSPDLESGCRAPNGTGPLCSGK 540
              * ** ***  **** ***** ***  ** *** ***  *** **  ****** *** * * ** *** *** ********** *****

564
                                      |
human b7  541:GHCQCGRCSCSGGSSGHLCECDDASCERHEGILCGGFGRCCCGVCHCHANRTGRACECSGDMDSCISPEGGLCSGHGRCKCNRCCCLDGY 630
mouse b7  541:GRCQCGRCSCSGGQSGRICECDCDDASCERHEGILCGGFGRCCCGVCHCHANHTGRACECSKSVDSCVSPEGGLCSGHGYCKCNRCQCLDGY 630
              * *********   * *************** ***** ****     ****** ** *** human b7  631:YGALCDQCPGCKTPCERHRDCAECGAFRTGPLATNCSTACAHTNVTLALAPILDBGWCKERTLDNQLFFLIVEDDARGTVVLRVRPQEKG 720
mouse b7  631:YGALCDQCLGCKSPCEQYRDCAECGAFGTGPLAANCSVVCADVNVTLTLAPNLDDGWCKERTIDNQLFFLVE-HAASGIVLRVRPQEKG 719
              ******** *** *** ** ****** ****** ** *** *** ** *******  ******* ** *   ***********

722
            |
human b7  721:ADHTQAIVLGCVCGGIVAVGLGLVLAVRLSVETYDRREYSRFEKEQQLNWKQDSNPLYKSAITTTINPRFQ--EADSPTL 798
mouse b7  720:VDHTRAITLGCTGGIVAVGLGIVLAVRLSVEIYDRREVRREKEQQLNWKQDNNPLYKSAITTTVNPRFQGTNGRSPSLSLTREAD 806
              ****  *  **  ******** *********  ***** * ***************  ******  ****     *
```

FIG. 24B

SEQUENCE LISTING

```
<160> NUMBER OF SEQ ID NOS: 31

<210> SEQ ID NO 1
<211> LENGTH: 8
<212> TYPE: PRT
<213> ORGANISM: Artificial Sequence
<220> FEATURE:
<223> OTHER INFORMATION: synthetic VH CDR1 of MMG49 antibody

<400> SEQUENCE: 1

Gly Tyr Thr Phe Ser Ser Tyr Trp
1               5

<210> SEQ ID NO 2
<211> LENGTH: 8
<212> TYPE: PRT
<213> ORGANISM: Artificial Sequence
<220> FEATURE:
```

```
<223> OTHER INFORMATION: synthetic VH CDR2 of MMG49 Antibody

<400> SEQUENCE: 2

Met Leu Pro Gly Ser Gly Ser Ser
1               5

<210> SEQ ID NO 3
<211> LENGTH: 12
<212> TYPE: PRT
<213> ORGANISM: Artificial Sequence
<220> FEATURE:
<223> OTHER INFORMATION: synthetic VH CDR3 of MMG49 Antibody

<400> SEQUENCE: 3

Ala Arg Gly Asp Gly Asn Tyr Trp Tyr Phe Asp Val
1               5                   10

<210> SEQ ID NO 4
<211> LENGTH: 131
<212> TYPE: PRT
<213> ORGANISM: Artificial Sequence
<220> FEATURE:
<223> OTHER INFORMATION: synthetic VH of MMG49 Antibody

<400> SEQUENCE: 4

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Ile Ser Cys Lys Ala Ser Gly Tyr Thr Phe
            35                  40                  45

Ser Ser Tyr Trp Ile Glu Trp Val Lys Gln Arg Pro Gly His Gly Leu
        50                  55                  60

Glu Trp Ile Gly Glu Met Leu Pro Gly Ser Gly Ser Ser Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
                100                 105                 110

Tyr Tyr Cys Ala Arg Gly Asp Gly Asn Tyr Trp Tyr Phe Asp Val Trp
            115                 120                 125

Gly Ala Gly
        130

<210> SEQ ID NO 5
<211> LENGTH: 461
<212> TYPE: PRT
<213> ORGANISM: Artificial Sequence
<220> FEATURE:
<223> OTHER INFORMATION: synthetic Heavy Chain of MMG49 Antibody

<400> SEQUENCE: 5

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Ile Ser Cys Lys Ala Ser Gly Tyr Thr Phe
            35                  40                  45

Ser Ser Tyr Trp Ile Glu Trp Val Lys Gln Arg Pro Gly His Gly Leu
        50                  55                  60
```

```
Glu Trp Ile Gly Glu Met Leu Pro Gly Ser Gly Ser Asn Tyr Asn
 65                  70                  75                  80

Glu Lys Phe Lys Gly Lys Ala Thr Phe Thr Ala Asp Thr Ser Ser Asn
                 85                  90                  95

Thr Ala Tyr Met Gln Leu Ser Ser Leu Thr Ser Glu Asp Ser Ala Val
             100                 105                 110

Tyr Tyr Cys Ala Arg Gly Asp Gly Asn Tyr Trp Tyr Phe Asp Val Trp
         115                 120                 125

Gly Ala Gly Ala Lys Thr Thr Ala Pro Ser Val Tyr Pro Leu Ala Pro
130             135                 140

Val Cys Gly Asp Thr Thr Gly Ser Ser Val Thr Leu Gly Cys Leu Val
145             150                 155                 160

Lys Gly Tyr Phe Pro Glu Pro Val Thr Leu Thr Trp Asn Ser Gly Ser
                 165                 170                 175

Leu Ser Ser Gly Val His Thr Phe Pro Ala Val Leu Gln Ser Asp Leu
             180                 185                 190

Tyr Thr Leu Ser Ser Ser Val Thr Val Thr Ser Ser Thr Trp Pro Ser
         195                 200                 205

Gln Ser Ile Thr Cys Asn Val Ala His Pro Ala Ser Ser Thr Lys Val
210             215                 220

Asp Lys Lys Ile Glu Pro Arg Gly Pro Thr Ile Lys Pro Cys Pro Pro
225                 230                 235                 240

Cys Lys Cys Pro Ala Pro Asn Leu Leu Gly Gly Pro Ser Val Phe Ile
                 245                 250                 255

Phe Pro Pro Lys Ile Lys Asp Val Leu Met Ile Ser Leu Ser Pro Ile
             260                 265                 270

Val Thr Cys Val Val Val Asp Val Ser Glu Asp Asp Pro Asp Val Gln
         275                 280                 285

Ile Ser Trp Phe Val Asn Asn Val Glu Val His Thr Ala Gln Thr Gln
290             295                 300

Thr His Arg Glu Asp Tyr Asn Ser Thr Leu Arg Val Val Ser Ala Leu
305                 310                 315                 320

Pro Ile Gln His Gln Asp Trp Met Ser Gly Lys Glu Phe Lys Cys Lys
                 325                 330                 335

Val Asn Asn Lys Asp Leu Pro Ala Pro Ile Glu Arg Thr Ile Ser Lys
             340                 345                 350

Pro Lys Gly Ser Val Arg Ala Pro Gln Val Tyr Val Leu Pro Pro Pro
         355                 360                 365

Glu Glu Glu Met Thr Lys Lys Gln Val Thr Leu Thr Cys Met Val Thr
370             375                 380

Asp Phe Met Pro Glu Asp Ile Tyr Val Glu Trp Thr Asn Asn Gly Lys
385                 390                 395                 400

Thr Glu Leu Asn Tyr Lys Asn Thr Glu Pro Val Leu Asp Ser Asp Gly
                 405                 410                 415

Ser Tyr Phe Met Tyr Ser Lys Leu Arg Val Glu Lys Lys Asn Trp Val
             420                 425                 430

Glu Arg Asn Ser Tyr Ser Cys Ser Val Val His Glu Gly Leu His Asn
         435                 440                 445

His His Thr Thr Lys Ser Phe Ser Arg Thr Pro Gly Lys
450                 455                 460

<210> SEQ ID NO 6
<211> LENGTH: 5
<212> TYPE: PRT
```

-continued

<210> SEQ ID NO 6
<211> LENGTH: (not shown)
<212> TYPE: PRT
<213> ORGANISM: Artificial Sequence
<220> FEATURE:
<223> OTHER INFORMATION: synthetic VL CDR1 of MMG49 Antibody

<400> SEQUENCE: 6

Ser Ser Val Gly Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: synthetic VL CDR2 of MMG49 Antibody

<400> SEQUENCE: 7

Ala Thr Ser
1

<210> SEQ ID NO 8
<211> LENGTH: 9
<212> TYPE: PRT
<213> ORGANISM: Artificial Sequence
<220> FEATURE:
<223> OTHER INFORMATION: synthetic VL CDR3 of MMG49

<400> SEQUENCE: 8

Gln Gln Trp Ser Ser Asp Pro Pro Thr
1               5

<210> SEQ ID NO 9
<211> LENGTH: 128
<212> TYPE: PRT
<213> ORGANISM: Artificial Sequence
<220> FEATURE:
<223> OTHER INFORMATION: synthetic VL of MMG49 ANtibody

<400> SEQUENCE: 9

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Gly Tyr Met His Trp Phe Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Ala Arg Phe Ser Gly Ser Glu Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Ser Ser Asp Pro Pro Thr Phe Gly Gly Gly Thr Lys Leu Glu Ile Lys
            115                 120                 125

<210> SEQ ID NO 10
<211> LENGTH: 234
<212> TYPE: PRT
<213> ORGANISM: Artificial Sequence
<220> FEATURE:
<223> OTHER INFORMATION: synthetic Light Chain of MMG49 Antibody

<400> SEQUENCE: 10

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Gly Tyr Met His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Glu Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Ser Ser Asp Pro Pro Thr Phe Gly Gly Gly Thr Lys Leu Glu Ile Lys
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 11
<211> LENGTH: 24
<212> TYPE: DNA
<213> ORGANISM: Artificial Sequence
<220> FEATURE:
<223> OTHER INFORMATION: synthetic VH CDR1 of MMG49 Antibody

<400> SEQUENCE: 11
ggctacacat tcagtagcta ctgg                                          24

<210> SEQ ID NO 12
<211> LENGTH: 24
<212> TYPE: DNA
<213> ORGANISM: Artificial Sequence
<220> FEATURE:
<223> OTHER INFORMATION: synthetic VH CDR2 of MMG49 Antibody

<400> SEQUENCE: 12
atgttacctg gaagtggtag ttct                                          24

<210> SEQ ID NO 13
<211> LENGTH: 36
<212> TYPE: DNA
<213> ORGANISM: Artificial Sequence
<220> FEATURE:
<223> OTHER INFORMATION: synthetic VH CDR3 of MMG49 Antibody

<400> SEQUENCE: 13
``` gcaaggggg atggtaacta ctggtacttc gatgtc                        36

<210> SEQ ID NO 14
<211> LENGTH: 393
<212> TYPE: DNA
<213> ORGANISM: Artificial Sequence
<220> FEATURE:
<223> OTHER INFORMATION: synthetic VH of MMG49 Antibody

<400> SEQUENCE: 14
atggaatgga cctgggtctt tctcttcctc ctgtcagtaa ctgcaggtgt ccactcccag    60
gttcagctgc agcagtctgg agctgagctg atgaagcctg gggcctcagt gaagatatcc   120
tgcaaggctt ctggctacac attcagtagc tactggatag agtgggtaaa gcagaggcct   180
ggacatggcc ttgagtggat tggagagatg ttacctggaa gtggtagttc taactacaat   240
gagaagttca agggcaaggc cacattcact gcagatacat cctccaacac agcctacatg   300
caactcagca gcctgacatc tgaggactct gccgtctatt actgtgcaag ggggatggt    360
aactactggt acttcgatgt ctggggcgca ggg                              393

<210> SEQ ID NO 15
<211> LENGTH: 1383
<212> TYPE: DNA
<213> ORGANISM: Artificial Sequence
<220> FEATURE:
<223> OTHER INFORMATION: synthetic Heavy Chain of MMG49 Antibody

<400> SEQUENCE: 15
atggaatgga cctgggtctt tctcttcctc ctgtcagtaa ctgcaggtgt ccactcccag    60
gttcagctgc agcagtctgg agctgagctg atgaagcctg gggcctcagt gaagatatcc   120
tgcaaggctt ctggctacac attcagtagc tactggatag agtgggtaaa gcagaggcct   180
ggacatggcc ttgagtggat tggagagatg ttacctggaa gtggtagttc taactacaat   240
gagaagttca agggcaaggc cacattcact gcagatacat cctccaacac agcctacatg   300
caactcagca gcctgacatc tgaggactct gccgtctatt actgtgcaag ggggatggt    360
aactactggt acttcgatgt ctggggcgca ggggctaaaa caacagcccc atcggtctat   420
ccactggccc ctgtgtgtgg agatacaact ggctcctcgg tgactctagg atgcctggtc   480
aagggttatt ccctgagcc agtgaccttg acctggaact ctggatccct gtccagtggt   540
gtgcacacct tcccagctgt cctgcagtct gacctctaca ccctcagcag ctcagtgact   600
gtaacctcga gcacctggcc cagccagtcc atcacctgca atgtggccca cccggcaagc   660
agcaccaagg tggacaagaa aattgagccc agagggccca atcaagcc ctgtcctcca    720
tgcaaatgcc cagcacctaa cctcttgggt ggaccatccg tcttcatctt ccctccaaag   780
atcaaggatg tactcatgat ctccctgagc cccatagtca catgtgtggt ggtggatgtg   840
agcgaggatg acccagatgt ccagatcagc tggtttgtga acaacgtgga agtacacaca   900
gctcagacac aaacccatag agaggattac aacagtactc tccgggtggt cagtgccctc   960
cccatccagc accaggactg gatgagtggc aaggagttca aatgcaaggt caacaacaaa  1020
gacctcccag cgcccatcga gaaccatc tcaaaaccca agggtcagt aagagctcca   1080
caggtatatg tcttgcctcc accagaagaa gagatgacta agaaacaggt cactctgacc  1140
tgcatggtca cagacttcat gcctgaagac atttacgtgg agtggaccaa caacgggaaa  1200
acagagctaa actacaagaa cactgaacca gtcctggact ctgatggttc ttacttcatg  1260
tacagcaagc tgagagtgga aaagaagaac tgggtggaaa gaaatagcta ctcctgttca  1320

```
gtggtccacg agggtctgca caatcaccac acgactaaga gcttctcccg gactccgggt    1380
aaa                                                                 1383

<210> SEQ ID NO 16
<211> LENGTH: 15
<212> TYPE: DNA
<213> ORGANISM: Artificial Sequence
<220> FEATURE:
<223> OTHER INFORMATION: synthetic VL CDR1 of MMG49 Antibody

<400> SEQUENCE: 16
tcaagtgtag gttac                                                      15

<210> SEQ ID NO 17
<211> LENGTH: 9
<212> TYPE: DNA
<213> ORGANISM: Artificial Sequence
<220> FEATURE:
<223> OTHER INFORMATION: synthetic VL CDR2 of MMG49 Antibody

<400> SEQUENCE: 17 gccacatcc                                                              9

<210> SEQ ID NO 18
<211> LENGTH: 27
<212> TYPE: DNA
<213> ORGANISM: Artificial Sequence
<220> FEATURE:
<223> OTHER INFORMATION: synthetic VL CDR3 of MMG49 Antibody

<400> SEQUENCE: 18
cagcagtgga gtagtgaccc accgacg                                         27

<210> SEQ ID NO 19
<211> LENGTH: 384
<212> TYPE: DNA
<213> ORGANISM: Artificial Sequence
<220> FEATURE:
<223> OTHER INFORMATION: synthetic VL of MMG49 Antibody

<400> SEQUENCE: 19
atggattttc aagtgcagat tttcagcttc ctgctaatca gtgcttcagt cataatgtcc     60
agaggacaaa ttgttctctc ccagtctcca gcaatcctgt ctgcatctcc aggggagaag    120
gtcacaatga cttgcagggc cagctcaagt gtaggttaca tgcactggtt ccagcagaag    180
ccaggatcct cccccaaacc ctggatttat gccacatcca acctggcttc tggagtccct    240
gctcgcttca gtggcagtga gtctgggacc tcttactctc tcacaatcag cagagtggag    300
gctgaagatg ctgccactta ttactgccag cagtggagta gtgacccacc gacgttcggt    360
ggaggcacca agctggaaat caaa                                           384

<210> SEQ ID NO 20
<211> LENGTH: 702
<212> TYPE: DNA
<213> ORGANISM: Artificial Sequence
<220> FEATURE:
<223> OTHER INFORMATION: synthetic Light Chain of MMG49 Antibody

<400> SEQUENCE: 20
atggattttc aagtgcagat tttcagcttc ctgctaatca gtgcttcagt cataatgtcc     60
agaggacaaa ttgttctctc ccagtctcca gcaatcctgt ctgcatctcc aggggagaag    120
```

```
gtcacaatga cttgcagggc cagctcaagt gtaggttaca tgcactggtt ccagcagaag    180
ccaggatcct cccccaaacc ctggatttat gccacatcca acctggcttc tggagtccct    240
gctcgcttca gtggcagtga gtctgggacc tcttactctc tcacaatcag cagagtggag    300
gctgaagatg ctgccactta ttactgccag cagtggagta gtgacccacc gacgttcggt    360
ggaggcacca agctggaaat caaagcagat gctgcaccaa ctgtatccat cttcccacca    420
tccagtgagc agttaacatc tggaggtgcc tcagtcgtgt gcttcttgaa caacttctac    480
cccaaagaca tcaatgtcaa gtggaagatt gatggcagtg aacgacaaaa tggcgtcctg    540
aacagttgga ctgatcagga cagcaaagac agcacctaca gcatgagcag caccctcacg    600
ttgaccaagg acgagtatga acgacataac agctatacct gtgaggccac tcacaagaca    660
tcaacttcac ccattgtcaa gagcttcaac aggaatgagt gt                       702

<210> SEQ ID NO 21
<211> LENGTH: 485
<212> TYPE: PRT
<213> ORGANISM: Artificial Sequence
<220> FEATURE:
<223> OTHER INFORMATION: synthetic CAR described in example

<400> SEQUENCE: 21

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Gly Tyr Met His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Glu Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asp Pro Pro Thr Phe Gly Gly Gly Thr Lys Leu Glu Ile Lys
        115                 120                 125

Arg Gly Ser Thr Ser Gly Ser Gly Lys Pro Gly Ser Gly Glu Gly Ser
    130                 135                 140

Gln Val Gln Leu Gln Gln Ser Gly Ala Glu Leu Met Lys Pro Gly Ala
145                 150                 155                 160

Ser Val Lys Ile Ser Cys Lys Ala Ser Gly Tyr Thr Phe Ser Ser Tyr
                165                 170                 175

Trp Ile Glu Trp Val Lys Gln Arg Pro Gly His Gly Leu Glu Trp Ile
            180                 185                 190

Gly Glu Met Leu Pro Gly Ser Gly Ser Ser Asn Tyr Asn Glu Lys Phe
        195                 200                 205

Lys Gly Lys Ala Thr Phe Thr Ala Asp Thr Ser Ser Asn Thr Ala Tyr
    210                 215                 220

Met Gln Leu Ser Ser Leu Thr Ser Glu Asp Ser Ala Val Tyr Tyr Cys
225                 230                 235                 240

Ala Arg Gly Asp Gly Asn Tyr Trp Tyr Phe Asp Val Trp Gly Ala Gly
                245                 250                 255

Thr Thr Val Thr Val Ser Ser Ala Ala Ala Ile Glu Val Met Tyr Pro
```

```
                    260                 265                 270
Pro Pro Tyr Leu Asp Asn Glu Lys Ser Asn Gly Thr Ile Ile His Val
            275                 280                 285

Lys Gly Lys His Leu Cys Pro Ser Pro Leu Phe Pro Gly Pro Ser Lys
            290                 295                 300

Pro Phe Trp Val Leu Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
                340                 345                 350

Gly Pro Thr Arg Lys His Tyr Gln Pro Tyr Ala Pro Pro Arg Asp Phe
                355                 360                 365

Ala Ala Tyr Arg Ser Arg Val Lys Phe Ser Arg Ser Ala Asp Ala Pro
            370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
        450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 22
<211> LENGTH: 1468
<212> TYPE: DNA
<213> ORGANISM: Artificial Sequence
<220> FEATURE:
<223> OTHER INFORMATION: CAR described in example

<400> SEQUENCE: 22
gaattccacc atggattttc aagtgcagat tttcagcttc ctgctaatca gtgcttcagt      60
cataatgtcc agaggacaaa ttgttctctc ccagtctcca gcaatcctgt ctgcatctcc     120
aggggagaag gtcacaatga cttgcagggc cagctcaagt gtaggttaca tgcactggtt     180
ccagcagaag ccaggatcct cccccaaacc ctggatttat gccacatcca acctggcttc     240
tggagtccct gctcgcttca gtggcagtga gtctgggacc tcttactctc tcacaatcag     300
cagagtggag gctgaagatg ctgccactta ttactgccag cagtggagta gtgacccacc     360
gacgttcggt ggaggcacca agctggaaat caaacggggc tccactagcg gttccggcaa     420
acctggcagc ggagaaggca gccaggttca gctgcagcag tctggagctg agctgatgaa     480
gcctggggcc tcagtgaaga tatcctgcaa ggcttctggc tacacattca gtagctactg     540
gatagagtgg gtaaagcaga ggcctggaca tggccttgag tggattggag agatgttacc     600
tggaagtggt agttctaact acaatgagaa gttcaagggc aaggccacat tcactgcaga     660
tacatcctcc aacacagcct acatgcaact cagcagcctg acatctgagg actctgccgt     720
ctattactgt gcaagggggg atggtaacta ctggtacttc gatgtctggg gcgcagggac     780
```

```
cacggtcacc gtctcctcag cggccgcaat tgaagttatg tatcctcctc cttacctaga      840
caatgagaag agcaatggaa ccattatcca tgtgaaaggg aaacaccttt gtccaagtcc      900
cctatttccc ggaccttcta agcccttttg ggtgctggtg gtggttggtg gagtcctggc      960
ttgctatagc ttgctagtaa cagtggcctt tattattttc tgggtgagga gtaagaggag     1020
caggctcctg cacagtgact acatgaacat gactccccgc cgccccgggc ccacccgcaa     1080
gcattaccag ccctatgccc caccacgcga cttcgcagcc tatcgctcca gagtgaagtt     1140
cagcaggagc gcagacgccc ccgcgtacca gcagggccag aaccagctct ataacgagct     1200
caatctagga cgaagagagg agtacgatgt tttggacaag agacgtggcc gggaccctga     1260
gatgggggga aagccgagaa ggaagaaccc tcaggaaggc ctgtacaatg aactgcagaa     1320
agataagatg gcgaggcct acagtgagat tgggatgaaa ggcgagcgcc ggaggggcaa     1380
ggggcacgat ggcctttacc agggtctcag tacagccacc aaggacacct acgacgccct     1440
tcacatgcag gccctgcccc ctcgctaa                                        1468
```

<210> SEQ ID NO 23
<211> LENGTH: 31
<212> TYPE: DNA
<213> ORGANISM: Artificial Sequence
<220> FEATURE:
<223> OTHER INFORMATION: synthetic Primer

<400> SEQUENCE: 23

```
gaattccacc atggattttc aagtgcagat t                                     31
```

<210> SEQ ID NO 24
<211> LENGTH: 42
<212> TYPE: DNA
<213> ORGANISM: Artificial Sequence
<220> FEATURE:
<223> OTHER INFORMATION: synthetic Primer

<400> SEQUENCE: 24

```
gccggaaccg ctagtggagc cccgtttgat ttccagcttg gt                         42
```

<210> SEQ ID NO 25
<211> LENGTH: 45
<212> TYPE: DNA
<213> ORGANISM: Artificial Sequence
<220> FEATURE:
<223> OTHER INFORMATION: synthetic Primer

<400> SEQUENCE: 25

```
gctgccttct ccgctgccag gtttgccgga accgctagtg gagcc                      45
```

<210> SEQ ID NO 26
<211> LENGTH: 44
<212> TYPE: DNA
<213> ORGANISM: Artificial Sequence
<220> FEATURE:
<223> OTHER INFORMATION: synthetic Primer

<400> SEQUENCE: 26

```
aaacctggca gcggagaagg cagccaggtt cagctgcagc agtc                       44
```

<210> SEQ ID NO 27
<211> LENGTH: 20
<212> TYPE: DNA
<213> ORGANISM: Artificial Sequence
<220> FEATURE:

<223> OTHER INFORMATION: synthetic Primer

<400> SEQUENCE: 27
tgaggagacg gtgaccgtgg        20

<210> SEQ ID NO 28
<211> LENGTH: 44
<212> TYPE: DNA
<213> ORGANISM: Artificial Sequence
<220> FEATURE:
<223> OTHER INFORMATION: synthetic Primer

<400> SEQUENCE: 28
atacataact tcaattgcgg ccgctgagga gacggtgacc gtgg        44

<210> SEQ ID NO 29
<211> LENGTH: 30
<212> TYPE: DNA
<213> ORGANISM: Artificial Sequence
<220> FEATURE:
<223> OTHER INFORMATION: synthetic Primer

<400> SEQUENCE: 29
ctaggcgccg gaattccacc atggattttc        30

<210> SEQ ID NO 30
<211> LENGTH: 29
<212> TYPE: DNA
<213> ORGANISM: Artificial Sequence
<220> FEATURE:
<223> OTHER INFORMATION: synthetic Primer

<400> SEQUENCE: 30
aatgtcgacc tcgagtggct gttagcgag        29

<210> SEQ ID NO 31
<211> LENGTH: 798
<212> TYPE: PRT
<213> ORGANISM: Homo sapiens

<400> SEQUENCE: 31

Met Val Ala Leu Pro Met Val Leu Val Leu Leu Val Leu Ser Arg
1               5                   10                  15

Gly Glu Ser Glu Leu Asp Ala Lys Ile Pro Ser Thr Gly Asp Ala Thr
            20                  25                  30

Glu Trp Arg Asn Pro His Leu Ser Met Leu Gly Ser Cys Gln Pro Ala
        35                  40                  45

Pro Ser Cys Gln Lys Cys Ile Leu Ser His Pro Ser Cys Ala Trp Cys
    50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
                85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
    130                 135                 140

Leu Arg Ala Glu Gly Tyr Pro Val Asp Leu Tyr Tyr Leu Met Asp Leu
145                 150                 155                 160

```
Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
    210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
        275                 280                 285

Asp Asp Thr Phe His Thr Ala Gly Asp Gly Lys Leu Gly Gly Ile Phe
    290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                325                 330                 335

Leu Ser Ala Ala Asn Ile Gln Pro Ile Phe Ala Val Thr Ser Ala Ala
            340                 345                 350

Leu Pro Val Tyr Gln Glu Leu Ser Lys Leu Ile Pro Lys Ser Ala Val
        355                 360                 365

Gly Glu Leu Ser Glu Asp Ser Ser Asn Val Val Gln Leu Ile Met Asp
    370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Arg
        515                 520                 525

Ala Pro Asn Gly Thr Gly Pro Leu Cys Ser Gly Lys Gly His Cys Gln
    530                 535                 540

Cys Gly Arg Cys Ser Cys Ser Gly Gln Ser Ser Gly His Leu Cys Glu
545                 550                 555                 560

Cys Asp Asp Ala Ser Cys Glu Arg His Glu Gly Ile Leu Cys Gly Gly
                565                 570                 575
```

-continued

```
Phe Gly Arg Cys Gln Cys Gly Val Cys His Cys His Ala Asn Arg Thr
                580             585             590

Gly Arg Ala Cys Glu Cys Ser Gly Asp Met Asp Ser Cys Ile Ser Pro
            595             600             605

Glu Gly Gly Leu Cys Ser Gly His Gly Arg Cys Lys Cys Asn Arg Cys
        610             615             620

Gln Cys Leu Asp Gly Tyr Tyr Gly Ala Leu Cys Asp Gln Cys Pro Gly
625             630             635             640

Cys Lys Thr Pro Cys Glu Arg His Arg Asp Cys Ala Glu Cys Gly Ala
            645             650             655

Phe Arg Thr Gly Pro Leu Ala Thr Asn Cys Ser Thr Ala Cys Ala His
            660             665             670

Thr Asn Val Thr Leu Ala Leu Ala Pro Ile Leu Asp Asp Gly Trp Cys
            675             680             685

Lys Glu Arg Thr Leu Asp Asn Gln Leu Phe Phe Phe Leu Val Glu Asp
            690             695             700

Asp Ala Arg Gly Thr Val Val Leu Arg Val Arg Pro Gln Glu Lys Gly
705             710             715             720

Ala Asp His Thr Gln Ala Ile Val Leu Gly Cys Val Gly Gly Ile Val
                725             730             735

Ala Val Gly Leu Gly Leu Val Leu Ala Tyr Arg Leu Ser Val Glu Ile
            740             745             750

Tyr Asp Arg Arg Glu Tyr Ser Arg Phe Glu Lys Glu Gln Gln Gln Leu
            755             760             765

Asn Trp Lys Gln Asp Ser Asn Pro Leu Tyr Lys Ser Ala Ile Thr Thr
770             775             780

Thr Ile Asn Pro Arg Phe Gln Glu Ala Asp Ser Pro Thr Leu
785             790             795
```

ANTIBODY

CROSS REFERENCE TO RELATED APPLICATIONS

This application is a continuation of U.S. application Ser. No. 16/808,451, filed Mar. 4, 2020, which is a continuation of U.S. application Ser. No. 15/751,574, filed on Feb. 9, 2018 (now U.S. Pat. No. 10,654,931, issued May 19, 2020), which is a National Stage of International Application No. PCT/JP2016/072688, filed on Aug. 2, 2016, which claims priority from Japanese Patent Application No. 2015-159240, filed on Aug. 11, 2015, the contents of all of which are incorporated herein by reference in their entirety.

TECHNICAL FIELD

A novel antibody, a use thereof, and the like are disclosed.

BACKGROUND ART

Multiple myeloma, which is a typical example of a disease causing neoplastic growth of plasma cells, accounts for about 1% of all cancers, and accounts for a little more than 10% of all hematological malignant tumors. Multiple myeloma is a disease in which a plasma cell present in bone marrow becomes cancerous (becomes an abnormal plasma cell as a result) and undergoes monoclonal growth.

In multiple myeloma, abnormal plasma cells (myeloma cells) spread to the bone marrow throughout the body and grow in every part of the bone marrow throughout the entire body. When the abnormal plasma cells grow, various symptoms including bone breakage appear. The myeloma cells produce M protein, which is an abnormal immunoglobulin, to increase an M protein concentration in blood, and hence the blood becomes viscous.

The M protein does not function as an original antibody, which recognizes a foreign substance, such as a pathogen, which has entered the body. Accordingly, immunocompetence is reduced. Those phenomena affect many organs, and thus various symptoms occur. Typical symptoms are bone pain and damage, hypercalcaemia, nephropathy and renal failure, anemia, and the like.

At present, as treatment of multiple myeloma, proteasome inhibitors, iMIDs, such as thalidomide and a derivative thereof, specifically lenalidomide, and chemotherapy using, for example, melphalan in combination with prednisone, and hematopoietic stem cell transplantation are mainly employed.

However, the myeloma cells eventually acquire resistance to those therapeutic agents in most cases. Accordingly, the reality of the current treatment means is that a myeloma patient has an unpromising prognosis with a mean survival period after onset of from about 3 years to about 5 years. In addition, those therapeutic agents do not specifically act on only tumor cells serving as targets, and hence have a problem of showing toxicity also to normal cells, consequently causing serious side effects.

There have been attempts to develop a treatment method for multiple myeloma utilizing a monoclonal antibody. For example, an anti-CS1 antibody, and an anti-CD38 antibody, and the like are considered promising (Non Patent Literatures 1 and 2). In addition, in Patent Literature 1, there is disclosed a therapeutic agent for multiple myeloma or the like, which uses an anti-human CD48 monoclonal antibody as an active ingredient.

Integrins mainly form a heterodimer of an α-chain and a β-chain to serve a function as a receptor on a cell surface in a living body. There are many combinations of α-chains and β-chains of such integrins.

In addition, in Non Patent Literatures 4 to 6, there are disclosed chimeric antigen receptor T-cells (CAR-T cells) including an antigen recognition site having an affinity for a certain antigen.

CITATION LIST

Patent Literature

PTL 1: WO 2010/117059 A1

Non-Patent Literature

NPL 1: Journal of Clinical Oncology, 2012 Jun. 1; 30(16): 1953-9.
NPL 2: Journal of immunology, 2011 Feb. 1; 186(3): 1840-8.
NPL 3: J Biol Chem. 2012 May 4; 287(19): 15749-59.
NPL 4: J Immunol. 2009 Nov. 1; 183(9): 5563-74.
NPL 5: N Engl J Med. 2014 Oct. 16; 371(16): 1507-17.
NPL 6: Nat Biotechnol. 2002 January; 20(1): 70-5.

SUMMARY OF INVENTION

Technical Problem

The anti-CS1 antibody has relatively high specificity to myeloma cells. However, the antibody alone cannot be said to have a high anti-myeloma effect, and its effectiveness as a single agent has not been demonstrated in a clinical test. It has been found that the anti-tumor effect of the anti-CS1 antibody is increased through combined use with lenalidomide, and it is considered that an approval is being sought for the combined use. Meanwhile, CD38 is also expressed in many normal blood cells including CD34-positive hematopoietic progenitor cells, and hence is an antigen having low specificity as a therapeutic target of multiple myeloma. Under such circumstances, an object of the present invention is to provide means that is more effective for the treatment of, for example, a disease involving neoplastic growth of plasma cells, such as multiple myeloma.

Solution to Problem

The inventors of the present invention have made extensive investigations in order to achieve such object, and as a result, have obtained an MMG49 antibody by performing screening through use of specific binding to myeloma cells and progenitors thereof as an indicator. In addition, the inventors have confirmed that such antibody binds to a certain region of human integrin $\beta_7$, and have found that CAR-T cells generated using an antigen recognition site of such antibody are extremely useful for the treatment of myeloma. In addition, the inventors have also elucidated that an epitope of the MMG49 antibody is present in the region of the amino acid residue positions 20 to 109 of the human integrin $\beta_7$.

The present invention has been completed on the basis of such findings, and encompasses inventions of a wide range of aspects described below.

(I) Antibody

An antibody (I) encompasses antibodies described in the following items (I-1) to (I-25).

(I-1)

An anti-human integrin $\beta_7$ antibody, whose epitope is present in a region of the amino acid residue positions 20 to 109 of human integrin $\beta_7$.

(I-1A)

An antibody according to the item (I-1), whose epitope is present in a region of the amino acid residue positions 33 to 109 of the human integrin $\beta_7$.

(I-1B)

An antibody according to the item (I-1), whose epitope is present in a region of the amino acid residue positions 20 to 90 of the human integrin $\beta_7$.

(I-1C)

An antibody according to the item (I-1), whose epitope is present in a region of the amino acid residue positions 33 to 90 of the human integrin $\beta_7$.

(I-2)

An antibody according to the item (I-1), whose affinity for the epitope is increased in the presence of at least part of a region of the amino acid residue positions 379 to 721 of the human integrin $\beta_7$.

(I-3)

An antibody according to the item (I-2), whose affinity for the epitope is increased in the presence of at least part of a region of the amino acid residue positions 417 to 721 of the human integrin $\beta_7$.

(I-4)

An antibody according to the item (I-2), whose affinity for the epitope is increased in the presence of at least part of a region of the amino acid residue positions 564 to 721 of the human integrin $\beta_7$.

(I-5)

An antibody according to the item (I-2), whose affinity for the epitope is increased in the presence of at least part of a region of the amino acid residue positions 379 to 563 of the human integrin $\beta_7$.

(I-6)

An antibody according to the item (I-2), whose affinity for the epitope is increased in the presence of at least part of a region of the amino acid residue positions 417 to 563 of the human integrin $\beta_7$.

(I-7)

An antibody according to the item (I-2), whose affinity for the epitope is increased in the presence of at least part of a region of the amino acid residue positions 379 to 416 of the human integrin $\beta_7$.

(I-8)

An antibody according to any one of the items (I-1) to (I-7), whose affinity for the epitope is increased through activation of the human integrin $\beta_7$.

(I-9)

An anti-human integrin $\beta_7$ antibody, whose affinity for human integrin $\beta_7$ expressed on myeloma cells is higher than for human integrin $\beta_7$ expressed on normal cells.

(I-10)

An antibody according to any one of the items (I-1) to (I-9), whose epitope is identical to that of an MMG49 antibody.

(I-11)

An antibody according to any one of the items (I-1) to (I-10), the antibody including:

a heavy chain variable region including:
heavy-chain CDR1 having the amino acid sequence set forth in SEQ ID NO: 1;
heavy-chain CDR2 having the amino acid sequence set forth in SEQ ID NO: 2; and/or
heavy-chain CDR3 having the amino acid sequence set forth in SEQ ID NO: 3; and/or a light chain variable region including:
light-chain CDR1 having the amino acid sequence set forth in SEQ ID NO: 6;
light-chain CDR2 having the amino acid sequence set forth in SEQ ID NO: 7; and/or
light-chain CDR3 having the amino acid sequence set forth in SEQ ID NO: 8.

(I-12)

An antibody according to any one of the items (I-1) to (I-10), the antibody including:

a heavy chain variable region having the amino acid sequence set forth in SEQ ID NO: 4; and/or a light chain variable region having the amino acid sequence set forth in SEQ ID NO: 9.

(I-13)

An antibody according to any one of the items (I-1) to (I-12), which is Fv, scFv, a diabody, a triabody, a tetrabody, or a combination thereof.

(I-14)

An antibody according to any one of the items (I-1) to (I-11), the antibody including a constant region.

(I-15)

An antibody according to any one of the items (I-1) to (I-12) and (I-14), which is a chimeric antibody.

(I-16)

An antibody according to any one of the items (I-1) to (I-12) and (I-14), which is a humanized antibody.

(I-17)

An antibody according to any one of the items (I-1) to (I-12) and (I-14), which is a human antibody.

(I-18)

An antibody according to any one of the items (I-1) to (I-12) and (I-14) to (I-17), which is an immunoglobulin, Fab, F(ab')$_2$, a minibody, scFv-Fc, or a combination thereof.

(I-19)

An antibody according to any one of the items (I-1) to (I-12) and (I-14) to (I-18), which is IgA, IgD, IgE, IgG, or IgM.

(I-20)

An antibody according to any one of the items (I-1) to (I-12) and (I-14) to (I-19), the antibody including a heavy chain having the amino acid sequence set forth in SEQ ID NO: 5 and/or a light chain having the amino acid sequence set forth in SEQ ID NO: 10.

(I-21)

An antibody according to any one of the items (I-1) to (I-20), which has cytotoxic activity.

(I-22)

An antibody according to the item (I-21), in which the cytotoxic activity is ADCC activity and/or CDC activity.

(I-23)

An antibody according to any one of the items (I-1) to (I-22), which is a multispecific antibody.

(I-24)

An antibody according to any one of the items (I-1) to (I-23), which has a cytotoxin bound thereto.

(I-25)

An antibody according to any one of the items (I-1) to (I-24), which is a monoclonal antibody.

(II) Polynucleotide

A polynucleotide (II) encompasses a polynucleotide described in the following item (II-1).

(II-1)

A polynucleotide, which has a base sequence encoding the amino acid sequence of the antibody (I).

(III) Host Cell

A host cell (III) encompasses a host cell described in the following item (III-1) or (III-2).

(III-1)

A host cell, which harbors the polynucleotide (II).

(III-2)

A host cell according to the item (III-1), which is a eukaryotic cell.

(IV) Chimeric Antigen Receptor

A chimeric antigen receptor (IV) encompasses chimeric antigen receptors described in the following items (IV-1) to (IV-5).

(IV-1)

A chimeric antigen receptor, whose epitope is identical to that of the antibody (I).

(IV-2)

A chimeric antigen receptor according to the item (IV-1), the chimeric antigen receptor including an antigen recognition site of the antibody (I).

(IV-3)

A chimeric antigen receptor according to the item (IV-1) or (IV-2), the antigen recognition site including:

a heavy chain variable region including:
heavy-chain CDR1 having the amino acid sequence set forth in SEQ ID NO: 1;
heavy-chain CDR2 having the amino acid sequence set forth in SEQ ID NO: 2; and/or
heavy-chain CDR3 having the amino acid sequence set forth in SEQ ID NO: 3; and/or
a light chain variable region including:
light-chain CDR1 having the amino acid sequence set forth in SEQ ID NO: 6;
light-chain CDR2 having the amino acid sequence set forth in SEQ ID NO: 7; and/or
light-chain CDR3 having the amino acid sequence set forth in SEQ ID NO: 8.

(IV-4)

A chimeric antigen receptor according to any one of the items (IV-1) to (IV-3), in which the antigen recognition site includes:

a heavy chain variable region having the amino acid sequence set forth in SEQ ID NO: 4; and/or
a light chain variable region having the amino acid sequence set forth in SEQ ID NO: 9.

(IV-5)

A chimeric antigen receptor according to any one of the items (IV-1) to (IV-4), the chimeric antigen receptor having the amino acid sequence set forth in SEQ ID NO: 21.

(V) Polynucleotide

A polynucleotide (V) encompasses a polynucleotide described in the following item (V-1) or (V-2) unlike the polynucleotide (II).

(V-1)

A polynucleotide, which encodes the amino acid sequence of the chimeric antigen receptor (IV).

(V-2)

A polynucleotide according to the item (V-1), which has the base sequence set forth in SEQ ID NO: 22.

(VI) Cell

A cell (VI) encompasses a cell described in any one of the following items (VI-1) to (VI-4) unlike the host cell (III).

(VI-1)

A cell, which harbors the polynucleotide (V).

(VI-2)

A cell according to the item (VI-1), which is a eukaryotic cell.

(VI-3)

A cell according to the item (VI-1) or (VI-2), which is a T-cell or an NK cell.

(VI-4)

A cell according to any one of the items (VI-1) to (VI-3), which is a chimeric antigen receptor T-cell or a chimeric antigen receptor NK cell.

(VII) Pharmaceutical Composition

A pharmaceutical composition (VII) encompasses pharmaceutical compositions described in the following items (VII-1) to (VII-5).

(VII-1)

A pharmaceutical composition, including the antibody (I) or the cell (VI).

(VII-2)

A pharmaceutical composition according to the item (VII-1), in which the cell is the chimeric antigen receptor T-cell (VI-4).

(VII-3)

A pharmaceutical composition according to the item (VII-1) or (VII-2), which is for use in treatment of cancer.

(VII-4)

A pharmaceutical composition according to the item (VII-3), in which the cancer is blood cancer.

(VII-5)

A pharmaceutical composition according to the item (VII-4), in which the blood cancer is a disease causing neoplastic growth of plasma cells.

(VIII) Treatment or Prevention Method for Disease

A treatment or prevention method (VIII) for a disease encompasses treatment or prevention methods for a disease described in the following items (VIII-1) to (VIII-6).

(VIII-1)

A treatment or prevention method for a disease, including administering a therapeutically effective amount of the antibody (I) or the cell (VI) to a subject.

(VIII-2)

A treatment or prevention method according to the item (VIII-1), in which the cell is the chimeric antigen receptor T-cell (VI-4).

(VIII-3)

A treatment or prevention method according to the item (VIII-1) or (VIII-2), in which the disease is cancer, and in which the subject is a patient who has developed cancer or an animal having a risk of developing cancer.

(VIII-4) A treatment or prevention method according to the item (VIII-3), in which the cancer is blood cancer.

(VIII-5)

A treatment or prevention method according to the item (VIII-4), in which the blood cancer is a disease causing neoplastic growth of plasma cells.

(VIII-6)

A treatment or prevention method for multiple myeloma, targeting active-form human integrin $\beta_7$.

(IX) Use

A use (IX) encompasses uses described in the following items (IX-1) to (IX-5).

(IX-1)

A use of the antibody (I) or the cell (VI), for producing a pharmaceutical composition.

(IX-2)

A treatment or prevention method according to the item (IX-1), in which the cell is the chimeric antigen receptor T-cell (VI-4).

(IX-3)

A use according to the item (IX-1) or (IX-2), which is for treatment of cancer.

(IX-4)

A use according to the item (IX-3), in which the cancer is blood cancer.

(IX-5)

A use according to the item (IX-4), in which the blood cancer is a disease causing neoplastic growth of plasma cells.

(X) Screening Method

A screening method (X) encompasses screening methods described in the following (X-1) to (X-5).

(X-1)

A screening method for an active ingredient of a pharmaceutical composition for treating or preventing cancer, the method including selecting, from a compound library, a candidate substance that specifically binds to human integrin $\beta_7$ and binds to a region of the amino acid residue positions 20 to 109 of the human integrin $\beta_7$.

(X-2)

A screening method according to the item (X-1), further including selecting a substance having cytotoxic activity.

(X-3)

A screening method according to the item (X-1) or (X-2), in which the substance to be selected is a monoclonal antibody.

(X-4)

A screening method according to any one of the items (X-1) to (X-3), in which the cancer is blood cancer.

(X-5)

A screening method according to the item (X-4), in which the blood cancer is a disease causing neoplastic growth of plasma cells.

(XI) Diagnosis Method

A diagnosis method (XI) encompasses diagnosis methods described in the following items (XI-1) to (XI-5).

(XI-1)

A diagnosis method for cancer, including bringing a sample collected from a subject into contact with the antibody (I).

(XI-2)

A diagnosis method according to the item (XI-1), in which the sample collected from a subject is blood or bone marrow fluid.

(XI-3)

A diagnosis method according to the item (XI-1) or (XI-2), further including judging that the subject has developed, or has a risk of developing, cancer when cells that bind to the antibody (I) are detected.

(XI-4)

A diagnosis method according to the item (XI-3), in which the cancer is blood cancer.

(XI-5)

A diagnosis method according to the item (XI-4), in which the cells are plasma cells, and in which the cancer is a disease causing neoplastic growth of plasma cells.

(XII) Kit

A kit (XII) encompasses kits described in the following items (XII-1) to (XII-3).

(XII-1)

A kit for diagnosis of cancer, including the antibody (I).

(XII-2)

A diagnosis method according to the item (XII-1), in which the cancer is blood cancer.

(XII-3)

A kit according to the item (XII-2), in which the cancer is a disease causing neoplastic growth of plasma cells.

Advantageous Effects of Invention

The antibody of the present invention does not recognize normal cells, and hence is useful as an active ingredient of a pharmaceutical composition. In particular, the antibody of the present invention is useful as an active ingredient of a therapeutic agent for cancer (e.g., blood cancer).

The antibody of the present invention is useful because chimeric antigen receptor T-cells produced by applying its antigen recognition site to a chimeric antigen receptor can be used as an active ingredient of such pharmaceutical composition as described above.

BRIEF DESCRIPTION OF DRAWINGS

In FIG. 7A, a comparison between hematopoietic stem cell and progenitor cell fractions, and myeloma cells is shown, and in FIG. 7B, a comparison between B/T lymphocyte fractions, and myeloma progenitor cell and myeloma plasma cell fractions is shown.

FIGS. 24A and 24B are views for illustrating a comparison between the amino acid sequence of integrin $\beta_7$ of human origin and the amino acid sequence of integrin $\beta_7$ of mouse origin.

DESCRIPTION OF EMBODIMENTS

Figure 1:
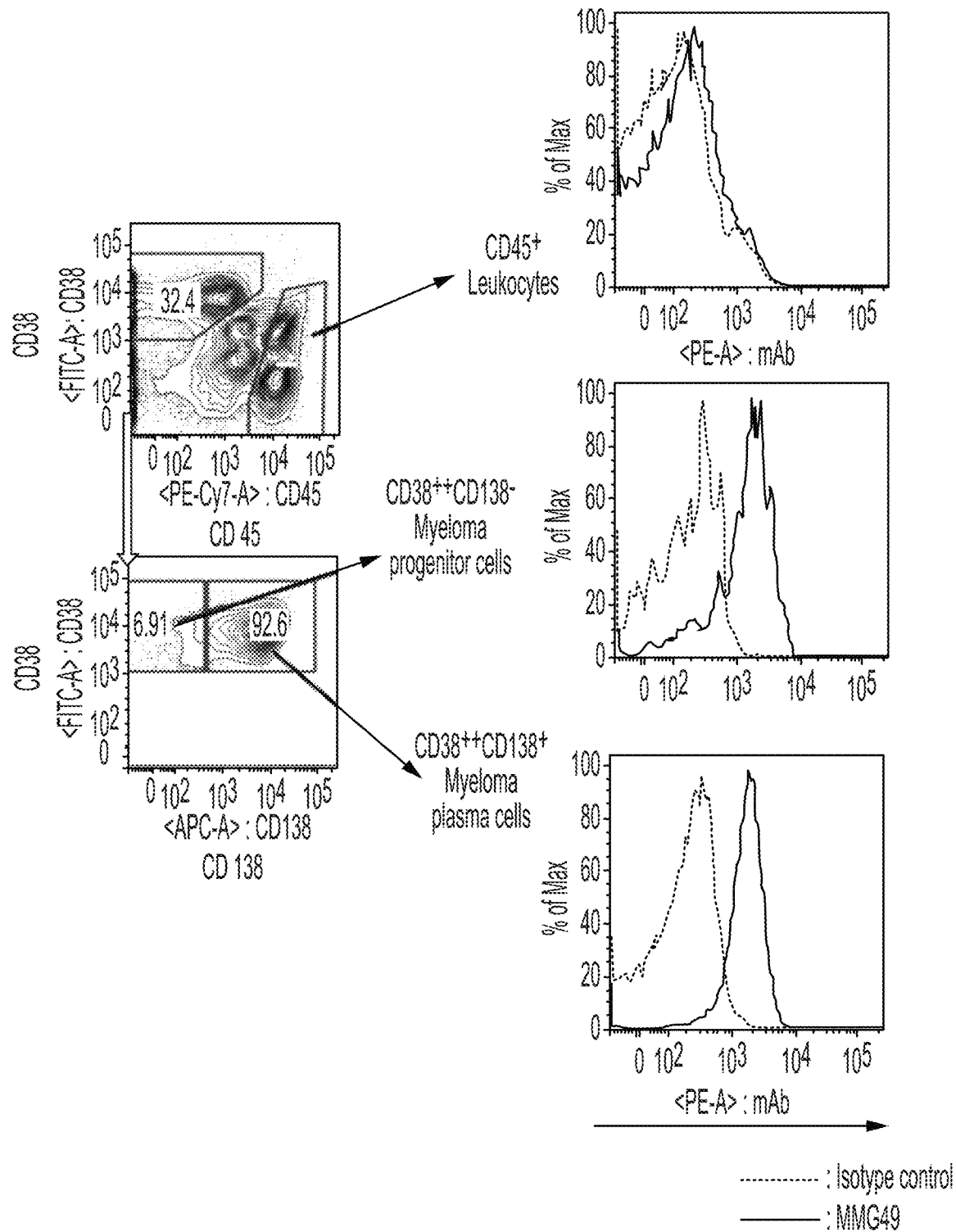
FIG. 1 shows results obtained in Example 2 by analyzing the binding of an MMG49 antibody to myeloma patient-derived bone marrow cells through use of FACS. (Left) A diagram for illustrating a method of identifying a myeloma progenitor cell fraction (Myeloma progenitor cells), a myeloma plasma cell fraction (Myeloma plasma cells), and CD45$^+$ leukocytes (CD45$^+$ leukocytes). (Right) Graphs for showing the binding of the MMG49 antibody to each of the fractions.

Herein, "include" and "have" are so-called open language, but are each a concept including the closed language "consisting of", and in one embodiment, may be replaced by "consisting of".

A "myeloma progenitor cell" is a progenitor cell in a stage before differentiating into a myeloma plasma cell, and is characterized by highly expressing CD38, but not expressing CD138, which serves as a marker specific to a mature plasma cell. Therefore, the myeloma progenitor cell is sometimes referred to as "CD38$^{++}$CD138$^-$ cell" or "CD19$^-$CD38$^{++}$CD138$^-$ cell".

A "myeloma plasma cell" is generally also called a myeloma cell, and is a cell that produces M protein, which is an abnormal immunoglobulin. The myeloma plasma cell expresses CD138 in addition to highly expressing CD38. Therefore, the myeloma plasma cell is sometimes referred to as "CD38$^{++}$CD138$^+$ cell" or "CD19$^-$ CD38$^{++}$CD138$^+$ cell".

The myeloma progenitor cell and the myeloma plasma cell also mean a tumor progenitor cell and a neoplastic plasma cell, respectively, in a disease causing neoplastic growth of plasma cells other than multiple myeloma.

A "hematopoietic progenitor cell" is a cell capable of differentiating into various hematopoietic cells. The hematopoietic progenitor cell is characterized by expressing CD34. Therefore, herein, the hematopoietic progenitor cell is sometimes referred to as "CD34+ cell".

(I) Antibody

An antibody (I) is preferably an anti-human integrin $\beta_7$ antibody whose epitope is present in the region of the amino acid residue positions 20 to 109 of human integrin $\beta_7$.

More preferred examples of the antibody (I) may include: an antibody whose epitope is present in the region of the amino acid residue positions 33 to 109 of human integrin $\beta_7$; and an antibody whose epitope is present in the region of the amino acid residue positions 20 to 90 of human integrin $\beta_7$. The most preferred example thereof may be an antibody whose epitope is present in the region of the amino acid residue positions 33 to 90 of human integrin $\beta_7$.

The human integrin $\beta_7$ is not particularly limited, and may be a transmembrane protein having the amino acid sequence set forth in SEQ ID NO: 31, the protein being capable of forming a heterodimer with integrin $\alpha$. Specific examples of the integrin $\alpha$ may include integrin $\alpha_4$ and integrin $\alpha_E$.

Specific examples of the amino acid sequence of the human integrin $\beta_7$ may include, in addition to the amino acid sequence set forth in SEQ ID NO: 31, amino acid sequences described in, for example: ACCESSION: EAW96675, VERSION: EAW96675.1, GI: 119617081; ACCESSION: NM000889, VERSION: NM000889.2, GI: 540344585; ACCESSION: XM005268851, VERSION: XM005268851.2, GI: 767974096; ACCESSION: XM006719376, VERSION: XM006719376.2, GI: 767974098; and ACCESSION: XM005268852, VERSION: XM005268852.3, GI: 767974097, listed in the NCBI database.

The following description regarding the human integrin $\beta_7$ is made on the basis of the amino acid sequence set forth in SEQ ID NO: 31. However, for any other amino acid sequence of the human integrin $\beta_7$, a person skilled in the art can easily judge which region or site of the other amino acid sequence of the human integrin $\beta_7$ corresponds to a region and/or site of the human integrin $\beta_7$ to be described below by determining the homology of the other amino acid sequence to the amino acid sequence set forth in SEQ ID NO: 31 in silico.

The region of the amino acid residue positions 1 to 19 of the human integrin $\beta_7$ is a peptide fragment serving as a signal peptide and being absent when the human integrin $\beta_7$ functions as a membrane protein in a living body. Accordingly, when the human integrin $\beta_7$ exhibits a function as a membrane protein, its N-terminus is the amino acid residue at position 20 of the above-mentioned amino acid sequence.

The region of the amino acid residue positions 20 to 109 of the human integrin $\beta_7$ includes a PSI domain. The PSI domain of the human integrin $\beta_7$ and the PSI domain of mouse integrin $\beta_7$ are known to have a high homology of about 80% or more. However, as illustrated in FIG. 24, when compared to each other, the amino acid residues of the regions of the amino acid residue positions 20 to 109 including the PSI domains of the human integrin $\beta_7$ and the mouse integrin $\beta_7$ differ from each other at a total of 15 amino acid residues, specifically amino acid residues at position 23, position 26, position 28, position 30, position 32, position 35, position 36, position 38, position 41, position 42, position 48, position 93, position 94, position 102, and position 109 of the human integrin $\beta_7$.

Therefore, it is preferred that the epitope of the antibody (I) be associated with any one or more, preferably two or more, more preferably three or more of those 15 amino acid residues. Specifically, the epitope of the antibody (I) is preferably present in the region of the amino acid residue positions 23 to 109 of the human integrin $\beta_7$, more preferably present in the region of the amino acid residue positions 23 to 48 or the region of the amino acid residue positions 93 to 109.

The epitope of the antibody (I) in another more preferred embodiment may be: the region of the amino acid residue positions 23 to 48; the region of the amino acid residue positions 93 to 109; or a three-dimensional region that is a combination of the region of the amino acid residue positions 23 to 48 and the region of the amino acid residue positions 93 to position 109.

The epitope of the antibody (I) may be a linear epitope, or may be a conformational epitope (also called a non-linear epitope). It is known to a person skilled in the art that the linear epitope is a case in which consecutive amino acid residues serve as an epitope and the conformational epitope is an epitope formed of non-consecutive amino acid residues.

For example, the case in which the above-mentioned three-dimensional region that is a combination of the region of the amino acid residue positions 23 to 48 and the region of the amino acid residue positions 93 to 109 serves as the epitope may be given as an example corresponding to the conformational epitope, and a case in which a region of non-consecutive amino acid residues included in the region of the amino acid residue positions 20 to 109 serves as the epitope is also encompassed in the conformational epitope.

Of the above-mentioned epitopes, it is preferred that the amino acid residue at position 48 be strongly related to the epitope of the antibody (I) or be included in the epitope of the antibody (I).

A person skilled in the art can understand about specific linear epitopes and conformational epitopes with reference to, for example, JP 2011-527572 A, JP 2009-534401 A, or "Dissecting antibodies with regards to linear and conformational epitopes." Forsstrom B, Axnas B B, Rockberg J, Danielsson H, Bohlin A, Uhlen M. PLoS One. 2015 Mar. 27; 10(3): e0121673. doi: 10.1371/journal.pone.0121673. eCollection 2015.

In other words, the foregoing means that the antibody (I) is an antibody that specifically binds to the region of the amino acid residue positions 20 to 109 of the human integrin $\beta_7$, and in particular, preferably specifically binds to the region at positions from 23 to 109, more preferably specifically binds to the region at positions from 23 to 48 and/or positions from 93 to 109.

In addition, the property of the antibody (I) of binding to the region of the amino acid residue positions 20 to 109 of the integrin $\beta_7$, which serves as the epitope, is sometimes referred to as affinity for the epitope. Accordingly, the term "affinity for the epitope is increased" has the same meaning as "specific binding capacity for the epitope is increased."

The term "specific" may be distinguished from the term "selective".

As another embodiment of the antibody (I), it is preferred that the affinity of the antibody (I) for the epitope be increased in the presence of at least part of the region of the amino acid residue positions 379 to 721 of the human integrin $\beta_7$.

The "at least part of the region of the amino acid residue positions 379 to 721" means that any one of the region of the amino acid residue positions 379 to 721 and a partial region thereof may be adopted. Specific examples of the "partial region thereof" include: at least part of the region of the amino acid residue positions 417 to 721 of the human integrin $\beta_7$; at least part of the region of the amino acid residue positions 564 to 721 of the human integrin $\beta_7$; at least part of the region of the amino acid residue positions 379 to 563 of the human integrin $\beta_7$; at least part of the region of the amino acid residue positions 417 to 563 of the human integrin $\beta_7$; and at least part of the region of the amino acid residue positions 379 to 416 of the human integrin $\beta_7$. That is, the affinity of the antibody (I) for the epitope can be increased in the presence of any of those regions.

The term "in the presence of" means that the region of the amino acid residue positions 20 to 109 of the human integrin $\beta_7$ and at least part of the region of the amino acid residue positions 379 to 721 of the human integrin $\beta_7$ may be present in the same molecule, or the two regions may be present as separate molecules. It is preferred that the two regions be present in the same molecule. The term "in the presence of" may be read as "by".

A person skilled in the art can easily confirm that the affinity of the above-mentioned antibody (I) for the epitope is increased, by a commonly used immunoassay method described in, for example, Examples to be described below.

For example, cells caused to express a human/mouse chimeric integrin $\beta_7$ protein (#4960), which is various human/mouse chimeric integrin $\beta_7$ proteins described in Example 8, and which includes the region of the amino acid residue positions 1 to 109 of integrin $\beta_7$ of human origin and includes the region of the amino acid residue positions 722 to 798 of the integrin $\beta_7$ of human origin, are prepared, and a human/mouse chimeric integrin $\beta_7$ protein (#4961) in which the region of #4960 of the amino acid residue positions 379 to 721 of the integrin $\beta_7$ of human origin is replaced with the region of the amino acid residue positions 379 to 721 of integrin $\beta_7$ of mouse origin is prepared. In this case, the increase in the affinity of the antibody (I) for the epitope may be confirmed by comparing the degrees of binding of the antibody (I) between cells expressing the latter (#4961) and cells expressing the former (#4960).

As another embodiment of the antibody (I), it is preferred that the affinity of the antibody (I) for the epitope be increased by activating the human integrin $\beta_7$. Probably because activated human integrin $\beta_7$ has a structural feature in a region including the epitope, the affinity of the antibody (I) for the epitope is increased.

A method of activating the human integrin $\beta_7$ is known. For example, by allowing a phorbol ester, such as PMA, a manganese salt, or the like to act on cells expressing the human integrin $\beta_7$, e.g., cells selected from blood cells and immune cells, such as plasma cells, NK cells, T-cells, B-cells, lymphoblasts, Burkitt lymphoma-derived cells, and dendritic cells, the human integrin $\beta_7$ expressed in the cells may be activated. In addition, without being limited to the above-mentioned specific cells, cells caused to express the human integrin $\beta_7$ may be used and treated with a phorbol ester, a manganese salt, or the like to activate the human integrin $\beta_7$.

A person skilled in the art can easily confirm that the affinity of the antibody (I) for the epitope is increased through activation of the human integrin $\beta_7$, by a commonly used immunoassay method described in, for example, Examples to be described below.

For example, cells caused to express #4960 or #4961, which is the various human/mouse chimeric integrin $\beta_7$ proteins described in Example 8 and includes the region of the amino acid residue positions 1 to 109, are prepared, and the cells are subjected to integrin $\beta_7$-activating means as described in Example 7. After that, affinities before and after the activation treatment are compared to each other through measurement using immunoassay means. Thus, the increase in the affinity of the antibody (I) for the epitope in the cells after the activation may be confirmed.

As another embodiment of the antibody (I), the antibody (I) may be an anti-human integrin $\beta_7$ antibody having a feature of having a higher affinity for human integrin $\beta_7$ expressed on myeloma-derived cells than for human integrin $\beta_7$ expressed on normal cells.

The normal cells are not particularly limited as long as the cells are derived from a healthy person, and may be, for example, blood-derived normal cells. Of such normal cells, normal plasma cells are preferred.

A method of confirming that the antibody has a higher affinity for human integrin $\beta_7$ expressed on myeloma cells than for human integrin $\beta_7$ expressed on such normal cells can easily be performed by a person skilled in the art by a commonly used immunoassay method described in, for example, Examples to be described below.

The "commonly used immunoassay method" is not particularly limited as long as the method involves measurement using various antibodies irrespective of the antigen. Examples thereof may include a flow cytometry method (FACS), cell sorting involved therein, western blotting, ELISA, an immunoprecipitation method, a SPR method, and a QCM method.

As another embodiment of the antibody (I), an epitope of the antibody (I) is preferably identical to that of an MMG49 antibody disclosed in Examples to be described later. An antibody identical to the MMG49 antibody is most preferred. For a method of producing the MMG49 antibody, reference may be made to Examples to be described below.

As another embodiment of the antibody (I), the antibody (I) is preferably an antibody of an embodiment including a heavy chain variable region and/or a light chain variable region. That is, the antibody (I) may be the heavy chain variable region alone, or may be the light chain variable region alone. The antibody (I) is preferably an antibody including the heavy chain variable region and the light chain variable region.

A variable region is also called an antigen recognition site, and is understood by a person skilled in the art to be a site important for an antibody to recognize an antigen. Such variable region has three regions called hypervariable regions (also referred to as complementarity determining regions [CDRs]), and it is also known to a person skilled in the art that the CDRs are extremely important regions most involved in the antigen recognition function of an antibody.

The heavy chain variable region included in the other embodiment of the antibody (I) includes any one or more of heavy-chain CDR1, heavy-chain CDR2, and heavy-chain CDR3. That is, the heavy chain variable region may contain heavy-chain CDR1, heavy-chain CDR2, or heavy-chain CDR3 alone, and preferably includes at least heavy-chain CDR3. A more preferred embodiment includes heavy-chain CDR1, heavy-chain CDR2, and heavy-chain CDR3 in the stated order from the amino-terminus (N-terminus).

The light chain variable region may be similar to the heavy chain variable region, i.e., includes, for example, any one of light-chain CDR1, light-chain CDR2, and light-chain CDR3, preferably includes at least light-chain CDR3, and preferably includes light-chain CDR1, light-chain CDR2, and light-chain CDR3 in the stated order from the N-terminus of the light chain variable region.

Regions other than CDR1 to CDR3 in each of the heavy chain variable region and the light chain variable region are sometimes referred to as FRs. More specifically, a region between the N-terminus and the CDR1 is called FR1, a region between the CDR1 and the CDR2 is called FR2, a region between the CDR2 and the CDR3 is called FR3, and a region between the CDR3 and the carboxy-terminus (C-terminus) is called FR4, and the names are designated for each of the heavy chain variable region and the light chain variable region.

The amino acid sequences of the heavy-chain CDR1 to CDR3 and the light-chain CDR1 to CDR3 are not particularly limited. Examples thereof include heavy-chain CDR1 having the amino acid sequence set forth in SEQ ID NO: 1, heavy-chain CDR2 having the amino acid sequence set forth in SEQ ID NO: 2, heavy-chain CDR3 having the amino acid sequence set forth in SEQ ID NO: 3, light-chain CDR1 having the amino acid sequence set forth in SEQ ID NO: 6, light-chain CDR2 having the amino acid sequence set forth in SEQ ID NO: 7, and light-chain CDR3 having the amino acid sequence set forth in SEQ ID NO: 8 serving as heavy-chain CDRs 1 to 3 or light-chain CDRs 1 to 3 of the MMG49 antibody.

As a preferred embodiment of the heavy chain variable region including the heavy-chain CDR1 to CDR3, there may be given, for example, a heavy chain variable region having the amino acid sequence set forth in SEQ ID NO: 4, which is a heavy chain variable region of the MMG49 antibody. In addition, as a preferred embodiment of the light chain variable region including the light-chain CDR1 to CDR3, there may be given, for example, a light chain variable region having the amino acid sequence set forth in SEQ ID NO: 9, which is a light chain variable region of the MMG49 antibody.

The above-mentioned amino acid sequences of the MMG49 antibody set forth in SEQ ID NOS: 1 to 4 and 6 to 9 are as shown in Table 1 below. Underlined parts in each of the amino acid sequences of the heavy chain and variable regions set forth in SEQ ID NOS: 4 and 9 in Table 1 indicate portions located at the CDR1, the CDR2, and the CDR3 in the stated order from the N-terminus.

TABLE 1

<Amino acid sequences of MMG49 antibody>

| | | |
|---|---|---|
| HeavyCDR1 | (SEQ ID NO: 1) | GYTFSSYW |
| chainCDR2 | (SEQ ID NO: 2) | MLPGSGSS |
| CDR3 | (SEQ ID NO: 3) | ARGDGNYWYFDV |
| Variable region (SEQ ID NO: 4) | | MEWTWVFLFLLSVTAGVHSQVQLQQS GAELMKPGASVKISCKASGYTFSSYW IEWVKQRPGHGLEWIGEMLPGSGSSN YNEKFKGKATFTADTSSNTAYMQLSS LTSEDSAVYYCARGDGNYWYFDVWGA G |
| LightCDR1 | (SEQ ID NO: 6) | SSVGY |
| chainCDR2 | (SEQ ID NO: 7) | ATS |
| CDR3 | (SEQ ID NO: 8) | QQWSSDPPT |
| Variable region (SEQ ID NO: 9) | | MDFQVQIFSFLLISASVIMSRGQIVL SQSPAILSASPGEKVTMTCRASSSVG YMHWFQQKPGSSPKPWIYATSNLASG VPARFSGSESGTSYSLTISRVEAEDA ATYYCQQWSSDPPTFGGGTKLEIK |

The structure of the antibody (I) is not limited. Specific examples of the structure include Fv, scFv, a diabody, a triabody, and a tetrabody, and the structure may also be a structure obtained by appropriately combining these structures. In addition, those structures including the combined structures as well are each sometimes also called a fragment antibody. Such fragment antibody may be an artificially designed recombinant protein including Fv, or may be one fused with a biomolecule, such as a protein.

The Fv is also called the smallest structural unit of an antibody, and is a structure in which a heavy chain variable region and a light chain variable region are associated with each other through a non-covalent intermolecular interaction. Further, the Fv may be a structure in which the thiol groups of cysteine residues present in the heavy chain variable region and the light chain variable region form a disulfide bond with each other.

The scFv is a structure in which the C-terminus of a heavy chain variable region and the N-terminus of a light chain variable region are linked through a linker, and is also called a single-chain antibody. In addition, the C-terminus and N-terminus to be linked through a linker may be the C-terminus of the light chain variable region and the N-terminus of the heavy chain variable region. The structure of the scFv may be formed by association based on a non-covalent intermolecular interaction or the like as in the Fv.

The diabody, the triabody, and the tetrabody are structures in which the above-mentioned scFv forms a dimer, a trimer, and a tetramer, respectively, and is associated in the structurally most stable state through a non-covalent intermolecular interaction or the like between variable regions as in the Fv or the like.

A person skilled in the art can easily produce the antibody (I) having any of such various structures by: constructing an expression vector through use of commonly used genetic engineering means; and using, with such expression vector, an expression system adopting host cells suited for antibody production, such as prokaryotic cells (such as *Escherichia coli* or actinomycetes) or eukaryotic cells (such as yeast cells, insect cells, or mammalian cells), a commonly used cell-free expression system, or the like. The produced antibody may be appropriately subjected to a commonly used purification process so as to be obtained in a high-purity state.

As another embodiment of the antibody (I), the antibody (I) may contain a constant region. The constant region is understood by a person skilled in the art to be as follows: a heavy chain constant region includes CH1, CH2, and CH3, and a light chain constant region includes CL. In addition, a region including CH2 and CH3 is sometimes called an Fc domain.

A specific origin of the constant region is not particularly limited. Examples thereof may include constant regions originating from animal species capable of mass production, animal species closely related to humans, animal species that are less liable to cause immunogenicity in administration to a human, and the like, e.g., constant regions of human origin, mouse origin, rat origin, rabbit origin, monkey origin, and chimpanzee origin.

In the antibody (I), when the heavy chain variable region and/or the light chain variable region have an amino acid sequence of mouse origin, for example, a constant region of human origin may be combined therewith, to thereby provide the antibody (I) as a chimeric antibody.

In addition, heavy-chain FR1 to FR4 and/or light-chain FR1 to FR4 in the above-mentioned chimeric antibody may be replaced with amino acid sequences of human origin, to thereby provide the antibody (I) as a humanized antibody.

Further, heavy-chain CDR1 to CDR3 and/or light-chain CDR1 to CDR3 in the above-mentioned humanized antibody may be replaced with amino acid sequences of human origin to the extent that the functions of the CDRs are not reduced, to thereby provide the antibody (I) as a human antibody. The term "human antibody" is sometimes called a "completely humanized antibody".

Examples of the structure of the antibody (I) of the embodiment including a constant region may include structures such as Fab, F(ab')$_2$, a minibody, and scFv-Fc, as well as an immunoglobulin having a four-chain structure including a pair of heavy chains each having a heavy chain variable region and a heavy chain constant region, and a pair of light chains each having a light chain variable region and a light chain constant region. Further, a structure obtained by appropriately combining those structures may also be adopted. In addition, those structures including combined structures are each sometimes called a fragment antibody. Such fragment antibody may be an artificially designed recombinant protein including Fv, or may be one fused with a biomolecule, such as a protein.

The Fab includes a heavy chain fragment including a heavy chain variable region and CH1 in a heavy chain constant region, and a light chain including a light chain variable region and a light chain constant region, and has a structure in which the heavy chain variable region and the light chain variable region are associated with each other through the above-mentioned non-covalent intermolecular interaction, or are bonded to each other through a disulfide bond. Further, the Fab may be such that the CH1 and the CL form a disulfide bond between the thiol groups of cysteine residues respectively present therein.

The F(ab')$_2$ has a pair of the Fabs, and has a structure in which the CH1s form a disulfide bond between the thiol groups of cysteine residues respectively included therein.

The minibody has a pair of antibody fragments each including the scFv and CH3, and has a structure in which such antibody fragments are associated with each other through a non-covalent intermolecular interaction between the CH3s.

The scFv-Fc has a pair of antibody fragments each including the scFv, CH2, and CH3, and has a structure in which, as in the minibody, the antibody fragments are associated with each other through a non-covalent intermolecular interaction between the CH3s, and form a disulfide bond between the thiol groups of cysteine residues included in the respective CH3s.

A person skilled in the art can easily produce the antibody (I) including a constant region having any of such various structures as with the antibody (I) including no constant region, by constructing an expression vector through use of commonly used genetic engineering means, and using, with such expression vector, an expression system adopting host cells suited for antibody production. The produced antibody may be appropriately subjected to a commonly used purification process so as to be obtained in a high-purity state.

The Fab may be obtained by, for example, digesting an immunoglobulin IgG with a protease such as papain. In addition, F(ab')$_2$, the F(ab')$_2$ may be obtained by digesting IgG with a protease such as pepsin.

Of the above-mentioned antibodies (I) each including a constant region, a preferred structure is an immunoglobulin. The subtype of such immunoglobulin is not particularly limited, and examples thereof may include IgA, IgD, IgE, IgG, and IgM. Of those, IgG is preferred, and for example, in the case of IgG of mouse origin, IgG2 is preferred out of the four subclasses.

Of the above-mentioned antibodies (I) each including a constant region, an antibody of a more preferred embodiment is an antibody including a heavy chain having the amino acid sequence set forth in SEQ ID NO: 5 and/or a light chain having the amino acid sequence set forth in SEQ ID NO: 10. The most preferred antibody is an antibody including a heavy chain having the amino acid sequence set forth in SEQ ID NO: 5 and a light chain having the amino acid sequence set forth in SEQ ID NO: 10.

A mutation may be introduced into each of the above-mentioned amino acid sequences depending on the situation. It is preferred that such mutation be not introduced into heavy-chain CDRs and light-chain CDRs. That is, the mutation is preferably introduced into a heavy-chain FR or a light-chain FR. When the antibody (I) includes a constant region, a mutation may be further introduced in addition to a mutation for adjusting ADCC activity or CDC activity to be described below.

A specific number of amino acid residues at which mutations are introduced is not particularly limited. For example, identity between an amino acid sequence before mutation introduction and an amino acid sequence after mutation introduction is about 70%, preferably about 75%, more preferably about 80%, more preferably about 85%, more preferably about 90%, more preferably about 95%, more preferably about 96%, more preferably about 97%, more preferably about 98%, most preferably about 99%. Such numerical value is one obtained by rounding.

The term "identity" refers to the degree of amino acid sequences identical to each other in two or more comparable amino acid sequences. Therefore, as the identity between given two amino acid sequences increases, it can be said that those sequences have not only higher identity but also higher similarity.

The identity of amino acids may be calculated using an analytical tool that is commercially available or available through the Internet (e.g., software such as FASTA, BLAST, PSI-BLAST, or SSEARCH). For example, main initial conditions to be generally used for a BLAST search are as described below. That is, a value (%) for the identity between amino acid sequences may be calculated by performing a search on Advanced BLAST 2.1 with blastp being used as a program, the Expect value being set to 10, all Filters being turned OFF, BLOSUM62 being used for Matrix, the Gap existence cost, Per residue gap cost, and Lambda ratio being set to 11, 1, and 0.85 (default values), respectively, and the other various parameters being also set to default values.

The above-mentioned introduction of a mutation into an amino acid sequence refers to substitution, deletion, insertion, or the like. Specific mutation introduction is not particularly limited as long as the mutation introduction can be achieved by adopting a commonly used method. For example, in the case of the substitution, a conservative substitution technology may be adopted.

The term "conservative substitution technology" means a technology involving substituting a certain amino acid residue with an amino acid residue having a side chain similar thereto.

For example, substitution between amino acid residues each having a basic side chain, such as lysine, arginine, and histidine, is a conservative substitution technology. In addition, each of substitutions between: amino acid residues each having an acidic side chain, such as aspartic acid and glutamic acid; amino acid residues each having an uncharged polar side chain, such as glycine, asparagine, glutamine, serine, threonine, tyrosine, and cysteine; amino acid residues each having a non-polar side chain, such as alanine, valine, leucine, isoleucine, proline, phenylalanine, methionine, and tryptophan; amino acid residues each having a β-branched side chain, such as threonine, valine, and isoleucine; and amino acid residues each having an aromatic side chain, such as tyrosine, phenylalanine, tryptophan, and histidine, is similarly a conservative substitution technology.

As another embodiment of the antibody (I), the antibody (I) may have cytotoxic activity. The cytotoxic activity refers to such activity that the antibody binds to cells, and as a result, causes some damage to the cells bound to the antibody.

Examples of such cytotoxic activity include ADCC activity and CDC activity. The term "ADCC activity" is an abbreviation of antibody-dependent cytotoxic activity (Antibody-Dependent Cellular Cytotoxicity), and is activity of recruiting cells having cytotoxic activity, such as NK cells expressing a receptor specific to a constant region of an antibody, to the vicinity of the antibody, to thereby induce damage to cells to which the antibody binds through the action of such cells and the like.

The term "CDC activity" is an abbreviation of complement-dependent cytotoxic activity (Complement-Dependent Cytotoxicity), and refers to activity that the antibody recruits a complement to its vicinity, to thereby induce an action of causing damage to cells bound to the antibody through the action of such complement.

Here, each of the ADCC activity and the CDC activity may be adjusted by introducing a mutation into a constant region while appropriately referring to the literature, such as Lazar G A et al., Proc Natl Acad Sci USA, 103: 4005-10 (2006), Shields R L et al., J Biol Chem, 276: 6591-604 (2001)), Moore G L et al., J Immunol, 159:3613-21 (1997), An Z et al., MAbs, 1:572-9 (2009).

For example, when the constant region is human IgG1, the ADCC activity may be increased by introducing a mutation such as S239D, I332E, S239D/I332E, S239D/I332E/A330L, S298A, K334A, S298A/K334A, or S298A/E333A/K334A.

In addition, when the constant region is human IgG1 as in the foregoing, the ADCC activity may be decreased by introducing a mutation such as V234A/G237A, or H268Q/V309L/A330S/P331S.

With regard to the CDC activity, when the constant region is human IgG1, the activity may be increased by introducing a mutation such as S267E, H268F, S324T, S267E/H268F, S267E/S324T, H268F/S324T, or S267E/H268F/S324T.

The ADCC activity may be measured in accordance with Brunner K. T., et al.'s method (Brunner, K. T., et al., Immunology, 1968. 14:181-96). For example, myeloma cells are cultured in RPMI1640 medium supplemented with 10% FCS, and are prepared so that the number of cells may be from $0.5 \times 10^4$ to $1.0 \times 10^4$. An appropriate amount of $Na_2{}^{51}CrO_4$ is added thereto and allowed to react therewith at 37° C. for 1 hour to label the cells with $^{51}Cr$, and the resultant cells are washed and then used as target cells. As effector cells, ones obtained by culturing SCID mouse bone marrow cells for 6 days in RPMI1640 supplemented with 10% FBS, 10 ng/ml mouse GM-CSF, and 40 IU/ml human IL2, or the like may be used. To a 96-well plate, an antibody to be tested or an isotype antibody thereof serving as a control is added at a final concentration from 0.05 μg/mL to 10 μg/mL, and the target cells ($1.0 \times 10^4$ cells) and the effector cells ($5 \times 10^5$ cells) are further added. The mixture is subjected to a reaction at 37° C. for 4 hours and centrifuged, and then $^{51}Cr$ released into the supernatant is measured with a γ-counter. The ADCC activity may be determined on the basis of the following equation.

ADCC activity={(([$^{51}$Cr release from target cells]–[spontaneous $^{51}$Cr release under antibody-free state])/([maximum $^{51}$Cr release amount caused by 1% Triton X-100 addition]–[spontaneous $^{51}$Cr release under antibody-free state])}×100

The CDC activity may also be measured in accordance with Brunner K. T., et al.'s method (Brunner, K. T., et al., Immunology, 1968. 14:181-96). For example, myeloma cells to be used as target cells are cultured in RPMI1640 medium supplemented with 10% FCS, and are prepared so that the number of cells may be from $0.5 \times 10^4$ to $1.0 \times 10^4$. An appropriate amount of $Na_2{}^{51}CrO_4$ is added thereto and allowed to react therewith at 37° C. for 1 hour to label the cells with $^{51}Cr$, and the resultant cells are washed and then used as target cells. An antibody to be tested or an isotype antibody serving as a control suspended in RPMI1640 medium supplemented with fetal bovine serum is added to a 96-well plate at a final concentration of from 0.5 μg/mL to 50 μg/mL, and then the target cells and a complement are added, followed by a reaction for 1.5 hours. The reaction liquid is centrifuged, and $^{51}Cr$ released into the supernatant is measured with a γ-counter. The CDC activity may be determined on the basis of the following equation.

CDC activity={(([$^{51}$Cr release from target cells]–[spontaneous $^{51}$Cr release under antibody-free state])/([maximum $^{51}$Cr release amount caused by 1% Triton X-100 addition]–[spontaneous $^{51}$Cr release under antibody-free state])}×100

The antibody having cytotoxic activity may be obtained by, for example, evaluating the presence or absence of cytotoxic activity through use of the above-mentioned method, and selecting an antibody having the activity.

As another embodiment of the antibody (I), the antibody (I) may be a multispecific antibody. That is, the antibody (I) may have binding capacity with specificity to an antigen other than the region of the amino acid residue positions 20 to 109 of the human integrin $\beta_7$ (the antigen is hereinafter referred to as other antigen).

The other antigen is preferably an antigen structurally dissimilar to the region of the amino acid residue positions 20 to 109 of the human integrin $\beta_7$.

A specific other antigen is not particularly limited. Examples thereof include CD3, CD16, C1q, and Adenovirus knob domain, and at least one of those antigens in appropriate combination may be appropriately adopted as the other antigen. It is preferred that one of the antigens given as examples above be selected as the other antigen. That is, a preferred multispecific antibody is a bispecific antibody.

A person skilled in the art can easily produce such multispecific antibody by appropriately adopting a commonly used technology. For example, the multispecific antibody may be obtained in the following manner: hybridomas generated using antibody-producing cells, such as B-cells, obtained from an animal immunized with cells expressing a peptide fragment corresponding to the region of the amino acid residue positions 20 to 109 of the human integrin $\beta_7$, or chimeric integrin $\beta_7$ in which only the region of the amino acid residue positions 20 to 109 of the human integrin $\beta_7$ is of human origin and the rest is of non-human origin, such as mouse origin, are prepared; separately, hybridomas are generated using antibody-producing cells, such as B-cells, obtained from an animal immunized with the above-mentioned other antigen; and screening is performed, by a commonly used method, for new hybridomas obtained by cell fusion between the above-mentioned hybridomas (the new hybridomas are also referred to as quadromas in the case of producing a bispecific antibody).

In addition to the foregoing, for example, in the case of a bispecific antibody, the bispecific antibody may be generated by a procedure described in the following (1) to (4):

(1) An antibody having the structure of the above-mentioned F(ab')$_2$, which uses the region of the amino acid residue positions 20 to 109 of the human integrin $\beta_7$ as an epitope, is generated;
(2) Meanwhile, an antibody having the structure of F(ab')$_2$ that specifically binds to the other antigen is also similarly generated;
(3) The antibodies of the respective F(ab')$_2$ structures obtained in (1) and (2) are treated with a reducing agent, such as DTT, and then any one of the treated products is further treated with Ellman's reagent; and
(4) The treated antibodies of the F(ab')$_2$ structures obtained in (3) are mixed and allowed to react with each other.

The bispecific antibody may also be produced by a procedure described in the following (A) to (D).
(A) An antibody using the region of the amino acid residue positions 20 to 109 of the human integrin $\beta_7$ as an epitope is generated.
(B) Meanwhile, an antibody that specifically binds to the other antigen is similarly generated.
(C) The amino acid sequences of respective variable regions obtained in (A) and (B) and the base sequences of polynucleotides encoding the variable regions are identified.
(D) An expression vector having incorporated therein polynucleotides having the respective base sequences identified in (C) together with, as necessary, polynucleotides having a base sequence for a constant domain and a linker sequence is generated, and then the expression vector is introduced into host cells suited for antibody production, such as CHO cells.

As another embodiment of the antibody (I), the antibody (I) may have bound thereto a cytotoxin (substance having cytotoxic activity). The cytotoxin is not particularly limited as long as the cytotoxin is a substance that causes some damage to cells, such as the killing of cells or the inhibition of cell growth.

Examples of such cytotoxin may include: alkylating agents, such as cyclophosphamide hydrate, iphosphamide, thiotepa, busulfan, melphalan, nimustine hydrochloride, ranimustine, dacarbazine, and temozolomide; metabolic antagonists, such as methotrexate, pemetrexed sodium hydrate, fluorouracil, doxifluridine, capecitabine, tegafur, cytarabine, gemcitabine hydrochloride, fludarabine phosphate, nelarabine, cladribine, and calcium levofolinate; antibiotic substances, such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin; microtubule inhibitors, such as vincristine sulfate, vinblastine sulfate, vindesine sulfate, and paclitaxel; aromatase inhibitors, such as anastrozole, exemestane, letrozole, and fadrozole hydrochloride hydrate; platinating agents, such as cisplatin, carboplatin, nedaplatin, and oxaliplatin; topoisomerase inhibitors, such as irinotecan hydrochloride hydrate, nogitecan hydrochloride, etoposide, and sobuzoxane; adrenal cortex steroids, such as prednisolone and dexamethasone; thalidomide and a derivative thereof, specifically lenalidomide; bortezomib serving as a protease inhibitor; and radioactive isotopes, such as 90-Ittrium.

Of those, calicheamicin, melphalan, vincristine sulfate, doxorubicin hydrochloride, prednisolone, dexamethasone, thalidomide, lenalidomide, and bortezomib are preferred, and calicheamicin having proven excellence in binding to an antibody is more preferred.

Each of those cytotoxins is commercially available, and one kind or two or more kinds in appropriate combination may be selected from the above-mentioned cytotoxins.

The manner of binding between the cytotoxin and the above-mentioned antibody is not particularly limited, and a person skilled in the art can easily bind the cytotoxin to the above-mentioned antibody by, for example, appropriately adopting a commonly used genetic engineering technology or protein engineering technology. More specifically, there may be given, for example, a method involving binding the cytotoxin to a functional group, such as an amino group, a thiol group, a guanidyl group, a hydroxy group, or a carboxyl group, of an amino acid residue side chain of the antibody (I) via a linker.

The antibody (I) may be a polyclonal antibody or may be a monoclonal antibody. The antibody (I) is preferably a monoclonal antibody.

The term "monoclonal" means being obtained from a substantially uniform population, and the "monoclonal antibody" means an antibody obtained from such population. That is, it is understood that individual antibodies included in such population are identical to each other except for a naturally occurring mutation that may be present in a minute amount.

Further, with regard to a specific binding target (epitope) of an antibody, for example, in the case of the antibody (I), the epitope is present in the region of the amino acid residue positions 20 to 109 of the human integrin $\beta_7$. In this regard, in the case of a polyclonal antibody, the epitope is a plurality of sites in the region of the amino acid residue positions 20 to 109 of the human integrin $\beta_7$, whereas in the case of a monoclonal antibody, the epitope is a single site. For this reason, the monoclonal antibody exhibits high specificity, and hence is more advantageous.

The term "monoclonal" to be used as a modifier is understood to mean being obtained from a substantially uniform population as described above, and should not be understood as a modifier for specifying a production method for the antibody.

Other than the above-mentioned method, a person skilled in the art can easily produce the antibody (I) by adopting a hybridoma method, a recombinant DNA method using a host cell (III) harboring a polynucleotide (II) to be described below, isolation from a phage library, or the like.

For example, there may be given a method involving: immunizing an animal suited for antibody production, such as a mouse, a rat, or a rabbit, with a peptide corresponding to the region of the amino acid residue positions 20 to 109 of the human integrin $\beta_7$; then recovering B-cells and subjecting the recovered B-cells to a hybridoma method; and performing screening through use of the function exhibited by the antibody (I) described above as an indicator, to thereby produce the antibody (I).

In addition to the foregoing, there may be given a method involving: generating cells expressing chimeric integrin $\beta_7$ in which only the region of the amino acid residue positions 20 to 109 of integrin $\beta_7$ is of human origin and the rest is of non-human origin, such as mouse origin; immunizing an animal suited for antibody production, such as a mouse, a rat, or a rabbit (preferably a mouse), with the cells; then recovering B-cells and subjecting the recovered B-cells to a hybridoma method; and performing screening through use of the function exhibited by the antibody (I) described above as an indicator, to thereby produce the antibody (I).

Examples of the function exhibited by the antibody (I) may include: an increase in affinity for the region of the amino acid residue positions 20 to 109 of the human integrin $\beta_7$ in the presence of at least part of the region of the amino acid residue positions 379 to 721 of the human integrin $\beta_7$; and an increase in the affinity through activation of the human integrin $\beta_7$. Accordingly, the antibody (I) may be obtained by a method shown in a screening method (X) to be described below, which utilizes such function.

An epitope for the antibody (I) is present in the region of the amino acid residue positions 20 to 109 of the human integrin $\beta_7$, and hence the antibody (I) is expected to exhibit cytotoxic activity or the like on cells expressing the integrin $\beta_7$ by combining one or two or more of not only the above-mentioned ADCC activity and CDC activity, but also apoptosis-inducing activity, survival signal-blocking activity, and the like on such cells. Accordingly, a composition including the antibody (I) is useful as a pharmaceutical composition (VII) as described in detail below.

In particular, the antibody (I) uses the region of the amino acid residue positions 20 to 109 of the human integrin $\beta_7$ as an epitope, and the affinity of the antibody (I) for the epitope is increased through activation of the integrin $\beta_7$. Active-form integrin $\beta_7$ is expressed in blood cells, such as plasma cells, and hence the antibody (I) is used as an active ingredient of a pharmaceutical composition for cancer thereof (e.g., blood cancer). In particular, the antibody (I) is effectively used as a pharmaceutical composition for a disease causing an abnormality in the above-mentioned cells (e.g., myeloma or multiple myeloma).

(II) Polynucleotide

A polynucleotide (II) is a polynucleotide having a base sequence encoding the amino acid sequence of the antibody (I). The term "polynucleotide" includes, for example, a single-stranded or double-stranded form in which a ribonucleotide, a deoxyribonucleotide, any one nucleotide thereof, or the like is appropriately modified by a known method.

A person skilled in the art can appropriately determine the base sequence of the polynucleotide (II), for example, in silico on the basis of the amino acid sequence of the antibody (I). The kinds of codons to be used for determining such base sequence are not limited. The base sequence is preferably determined in consideration of the codon frequency of a host in which the polynucleotide is to be used.

A specific base sequence of the polynucleotide (II) is not particularly limited. Correspondence between each SEQ ID NO in which an amino acid sequence identified as one embodiment of the antibody (I) is set forth and the SEQ ID NO in which a base sequence encoding such amino acid sequence is set forth is shown in Table 2 below. That is, preferred base sequences of the polynucleotide (II) are base sequences set forth in SEQ ID NOS: 11 to 20.

TABLE 2

| Amino acid sequence | Base sequence |
| --- | --- |
| SEQ ID NO: 1 | SEQ ID NO: 11 |
| SEQ ID NO: 2 | SEQ ID NO: 12 |
| SEQ ID NO: 3 | SEQ ID NO: 13 |
| SEQ ID NO: 4 | SEQ ID NO: 14 |
| SEQ ID NO: 5 | SEQ ID NO: 15 |
| SEQ ID NO: 6 | SEQ ID NO: 16 |
| SEQ ID NO: 7 | SEQ ID NO: 17 |
| SEQ ID NO: 8 | SEQ ID NO: 18 |
| SEQ ID NO: 9 | SEQ ID NO: 19 |
| SEQ ID NO: 10 | SEQ ID NO: 20 |

The polynucleotide (II) may adopt an embodiment of being incorporated into a vector. The vector is not particularly limited, and may be, for example, a vector for cloning or a vector for expression, and its intended use is not limited.

In addition, the vector for expression may be a vector for prokaryotic cells, such as *Escherichia coli* or actinomycetes, or may be a vector for eukaryotic cells, such as yeast cells, insect cells, or mammalian cells.

A base sequence encoding a signal peptide may be appropriately added to the 5'-end side of the polynucleotide (II) (corresponding to the N-terminus side of the antibody (I)).

A specific method of using the polynucleotide (II) is not particularly limited. For example, the polynucleotide (II) may be used for expressing the antibody (I) by being introduced into the following host cell (III).

(III) Host Cell

A host cell (III) is a cell harboring the polynucleotide (II). The term "harbor" refers to the keeping of a state in which the polynucleotide (II) is present in the cell, and means that the cell is in a state of not spontaneously discharging the polynucleotide to the outside of the cell irrespective of whether the discharge is active.

The embodiment in which the host cell (III) harbors the polynucleotide (II) is not particularly limited. For example, the polynucleotide may be harbored in the form of a vector in the cell, or the polynucleotide (II) may be harbored in the form of being integrated into the genome in the cell.

A specific cell kind of the host cell (III) may be a eukaryotic cell, such as a yeast cell, an insect cell, or a mammalian cell, or may be a prokaryotic cell, such as *Escherichia coli* or an actinomycete, and is not particularly limited.

(IV) Chimeric Antigen Receptor

A chimeric antigen receptor is an artificial T-cell receptor (TCR)-like protein, and is a protein in which an antigen recognition site expressed on the cell membrane of T-cells (corresponding to an extracellular domain) is replaced with a desired antigen recognition site and which is constructed so as to be able to more effectively exhibit a function, such as cytotoxic activity, of T-cells themselves.

The chimeric antigen receptor (IV) is a chimeric antigen receptor whose epitope is identical to that of the antibody (I), and more specifically, is a protein including an antigen recognition site of the antibody (I). That is, the epitope present in the antigen recognition site included in the chimeric antigen receptor may be the same as the one described in detail in the antibody (I).

More specifically, the chimeric antigen receptor (IV) is a protein in which the antigen recognition site of the antibody (I), a spacer sequence, a transmembrane domain, a costimulator, and an TCR intracellular domain are arranged in the stated order from the N-terminus of the chimeric antigen receptor (IV).

The antigen recognition site of the antibody (I) to be arranged in the chimeric antigen receptor (IV) may be as described in detail in the antibody (I), and specific examples thereof may include a heavy chain variable region and/or a light chain variable region. Of those, the antigen recognition site preferably has the structure of scFv while having a heavy chain variable region and a light chain variable region.

In such scFv, for example, between the heavy chain variable region and the light chain variable region, a spacer sequence consisting of about 10 to about 25 amino acid residues may be appropriately arranged. The number of amino acid residues is more preferably from about 15 to about 18. Such spacer sequence may be identical to the above-mentioned spacer sequence to be arranged in the chimeric antigen receptor (IV), or may be different therefrom.

The spacer sequence to be arranged in the chimeric antigen receptor (IV) is not particularly limited. For example, the spacer sequence may be consisting of about 10 to about 25 amino acid residues. The number of amino acid residues is more preferably from about 15 to about 18.

The transmembrane domain to be arranged in the chimeric antigen receptor (IV) is not particularly limited. Specifically, a cell transmembrane domain derived from a protein, such as CD28 or 4-1BB, expressed in T-cells or the like may be adopted while being allowed to appropriately have a mutation introduced thereinto.

The costimulator to be arranged in the chimeric antigen receptor (IV) may be a costimulator of T-cells or the like, and is not particularly limited. For example, 4-1BB, OX40, CD28, or the like may be adopted while being allowed to appropriately have a mutation introduced thereinto.

The TCR intracellular domain to be arranged in the chimeric antigen receptor (IV) is not particularly limited. For example, an intracellular domain derived from CD3, which is also called a TCRζ chain, or the like may be adopted while being allowed to appropriately have a mutation introduced thereinto. It is preferred that a mutation be introduced into CD3 so as to include an Immunoreceptor Tyrosine-based Activation Motif (ITAM).

The chimeric antigen receptor (IV) preferably has the amino acid sequence set forth in SEQ ID NO: 21.

A mutation may be appropriately introduced into an amino acid sequence identifying the above-mentioned chimeric antigen receptor. In addition, a mutation may also be similarly introduced into each of the above-mentioned transmembrane domain, costimulator, and TCR intracellular domain. A specific number of mutations to be introduced is not particularly limited.

For example, identity between an amino acid sequence before mutation introduction and an amino acid sequence after mutation introduction is about 70%, preferably about 75%, more preferably about 80%, more preferably about 85%, more preferably about 90%, more preferably about 95%, more preferably about 96%, more preferably about 97%, more preferably about 98%, most preferably about 99%. Such numerical value is one obtained by rounding.

The above-mentioned introduction of a mutation into an amino acid sequence refers to substitution, deletion, insertion, or the like. Specific mutation introduction is not particularly limited as long as the mutation introduction can be achieved by adopting a commonly used method. For example, in the case of the substitution, a conservative substitution technology may be adopted.

For the production of such chimeric antigen receptor, a person skilled in the art can easily produce the chimeric antigen receptor with reference to a method described in, for example, each of Non Patent Literatures 4 to 6.

(V) Polynucleotide

A polynucleotide (V) is a polynucleotide encoding the amino acid sequence of the chimeric antigen receptor (IV) unlike the polynucleotide (II).

As in the polynucleotide (II), the base sequence of the polynucleotide (V) may be appropriately determined, for example, in silico on the basis of the amino acid sequence of the chimeric antigen receptor (IV). The kinds of codons to be used for determining the base sequence are not limited. The base sequence is preferably determined in consideration of the codon frequency of cells serving as a target for which the polynucleotide is to be used.

A specific base sequence is not particularly limited. For example, there may be given a polynucleotide having the base sequence set forth in SEQ ID NO: 22, which is determined on the basis of the amino acid sequence of the chimeric antigen receptor (IV) having the amino acid sequence set forth in SEQ ID NO: 21. Of course, in consideration of the kinds of the codons to be used being not limited, needless to say, the base sequence to be determined on the basis of such amino acid sequence is not limited to the base sequence set forth in SEQ ID NO: 22.

A base sequence encoding a signal peptide may be appropriately added to the 5'-end side of the polynucleotide (V) (corresponding to the N-terminus side of the chimeric antigen receptor (IV)).

A specific method of using the polynucleotide (V) is not particularly limited. For example, the polynucleotide (V) may be used for expressing the chimeric antigen receptor (IV) by being introduced into the following cell (VI).

(VI) Cell

A cell (VI) is a cell harboring the polynucleotide (V) unlike the host cell (III). The term "harbor" may be the same as in the host cell (III). A specific kind of the cell may also be the same as in the host cell (III), but the cell (VI) preferably has cytotoxic activity. Examples thereof may include a T-cell, an NK cell, and a K cell. Of those, a killer T-cell (sometimes referred to as cytotoxic T-cell [CTL]), which is a kind of T-cell, is most preferred.

It is preferred that, when the polynucleotide (V), which encodes the chimeric antigen receptor, included in the cell (VI) is expressed, the antigen recognition site of the antibody (I) serving as a component of the chimeric antigen receptor (IV) be exposed to the outside of the cell, and the transmembrane domain, the costimulator, or the TCR intracellular domain serving as a component of the chimeric antigen receptor (IV) be localized on a cell membrane or inside the cell.

The costimulator, or the domain to be localized on the cell membrane or inside the cell activates a signal that induces cytotoxic activity in cells when the antigen recognition site of the antibody (I) binds to the region of the amino acid residue positions 20 to 109 of the human integrin $\beta_7$. In addition, the affinity of the antibody (I) for the region of the amino acid residue positions 20 to 109 of the human integrin $\beta_7$ is increased through activation of the human integrin $\beta_7$. Therefore, the antibody (I) attacks, or exhibits cytotoxic activity on, a cell or tissue expressing active-form integrin $\beta_7$ serving as a target.

When the cell exhibiting such function is a T-cell, the cell is referred to as chimeric antigen receptor T-cell (VI-4). Like the chimeric antigen receptor T-cell, a cell having the possibility of exhibiting cytotoxic activity, such as an NK cell, can also exhibit an effect similar to that of the chimeric antigen receptor T-cell (such cell is referred to as chimeric antigen receptor NK cell) through cooperation between the binding of the antigen recognition site to the region of the amino acid residue positions 20 to 109 of active-form human integrin $\beta_7$, and the activation of a signal that induces cytotoxic activity at the cell membrane or the intracellular domain.

As described above, the cell (VI) exhibits cytotoxic activity and the like on a cell or tissue expressing active-form integrin $\beta_7$. Accordingly, as with the antibody (I), a composition including the cell (VI) may be said to be useful as such a pharmaceutical composition (IV) as described in detail below. The active-form integrin $\beta_7$ is expressed in blood cells, such as plasma cells, and hence the cell (VI) is used as an active ingredient of a pharmaceutical composition for cancer (e.g., blood cancer). In particular, the cell (VI) is effectively used as a pharmaceutical composition for a disease causing an abnormality in the above-mentioned cells (e.g., myeloma or multiple myeloma).

(VII) Pharmaceutical Composition

A pharmaceutical composition (VII) includes the antibody (I) or the cell (VI). The cell (VI) is preferably the chimeric antigen receptor T-cell (VI-4).

The content of the antibody (I) or the cell (VI) in the pharmaceutical composition (VII) is not particularly limited. For example, in the case of the antibody (I), the content may be from about 0.001 part by weight to about 10 parts by weight with respect to 100 parts by weight of the pharmaceutical composition. In addition, in the case of the cell (VI), the content may be from about 1 cell/mL to about $10^4$ cells/mL.

An administration method for the pharmaceutical composition (VII) is not particularly limited. Because its active ingredient is an antibody or a cell, parenteral administration or non-enteral administration is preferred. Examples thereof include intravenous administration, intramuscular administration, and subcutaneous administration. Of those, intravenous administration is preferred.

A dosage form of the pharmaceutical composition (VII) may be prepared together with a pharmacologically acceptable and commonly used carrier depending on the above-mentioned administration method. In consideration of the above-mentioned preferred administration method, the dosage form is preferably an injection.

A target disease of the pharmaceutical composition (VII) is not particularly limited. A specific example of the target disease is cancer, preferably blood cancer, more preferably a disease causing neoplastic growth of plasma cells. The term "disease causing neoplastic growth of plasma cells" refers to a disease characterized by neoplastic growth of abnormal plasma cells and an increase in abnormal protein secreted therefrom. Examples of such disease may include myeloma, multiple myeloma, plasma cell leukemia, plasmacytoma, H chain disease, and systemic AL amyloidosis. In another embodiment, the target disease of the pharmaceutical composition (VII) may be a different hematologic malignancy, such as malignant lymphoma or leukemia.

An administration target (subject) of the pharmaceutical composition (VII) may be a patient who has developed the above-mentioned disease, or may be an animal having a risk of developing the above-mentioned disease. Whether "having a risk of developing" may be determined by a diagnosis method (XI) to be described later. The animal may be, for example, a mammal, and is preferably a human.

The dose of the pharmaceutical composition (VII) varies depending on various conditions of the administration target, such as the severity of the disease, the degree of a desired effect achieved by the administration, body weight, sex, age, and animal species, and cannot be unconditionally determined. For example, when the active ingredient is the antibody (I), the dose may be generally from about 1 μg/kg (body weight) to about 10 g/kg (body weight) per day. In addition, when the active ingredient is the cell (VI), the dose may be generally from about $10^4$ cells/kg (body weight) to about $10^9$ cells/kg (body weight).

As with its dose, the administration schedule of the pharmaceutical composition (VII) also varies depending on various conditions of the administration target, such as the severity of the disease, and cannot be unconditionally determined. For example, the pharmaceutical composition (VII) is preferably administered in the above-mentioned daily dose at a frequency of from once a day to once a month.

(VIII) Treatment or Prevention Method for Disease

A treatment or prevention method (VIII) for a disease is a treatment or prevention method for a disease including a step of administering a therapeutically effective amount of the antibody (I) or the cell (VI) to a subject. The cell (VI) is preferably the chimeric antigen receptor T-cell (VI-4).

The subject may be the same as in the pharmaceutical composition (VII). When the subject is a patient who has developed a disease, the administration of the therapeutically effective amount of the antibody (I) or the cell (VI) is expected to achieve a therapeutic effect thereon, and when the subject is an animal having a risk of developing a disease, the administration is expected to achieve a preventing effect thereon. As described in a diagnosis method (XI) to be described below, the preventing means keeping of a numerical value measured by a commonly used immunological method from reaching a numerical value at which it is judged that a disease has developed.

The disease may be the same as in the pharmaceutical composition (VII), and is exemplified by, for example, cancer. A preferred example of the cancer may be a disease causing neoplastic growth of plasma cells (e.g., multiple myeloma).

The therapeutically effective amount may be the same as the dose of the pharmaceutical composition (VII), and a formulation of the antibody (I) or the cell (VI) may be the same as the dosage form of the pharmaceutical composition (VII). In addition, an administration method for the antibody (I) or the cell (VI), an administration schedule therefor, and the like may also be as described in detail in the pharmaceutical composition (VII).

The treatment or prevention method (VIII) for a disease may encompass a treatment or prevention method for multiple myeloma including targeting active-form human integrin $\beta_7$. An example of the targeting may be application of the antibody (I) or the cell (VI).

(IX) Use

A use (IX) is a use of the antibody (I) or the cell (IV), for producing a pharmaceutical composition.

The pharmaceutical composition may be the same as the pharmaceutical composition (VII). The cell (IV) is preferably the chimeric antigen receptor T-cell (VI-4).

In addition, a target disease of the pharmaceutical composition is also the same, and the pharmaceutical composition is used for treating, for example, cancer, preferably blood cancer, more preferably a disease causing neoplastic growth of plasma cells (e.g., myeloma or multiple myeloma).

Besides, the content of the antibody (I) or the cell (VI) serving as an active ingredient in the pharmaceutical composition, the dosage form thereof, an administration method therefor, an administration schedule therefor, and the like may also be the same as those described in detail in the pharmaceutical composition (VII).

(X) Screening Method

A screening method (X) is a screening method for an active ingredient of a pharmaceutical composition for treating or preventing a disease causing neoplastic growth of plasma cells, including a step of selecting, from a compound library, a candidate substance that specifically binds to human integrin $\beta_7$ and binds to a region of the amino acid residue positions 20 to 109 of the human integrin $\beta_7$.

The pharmaceutical composition may be the same as the pharmaceutical composition (VII), and an example of an active ingredient of the pharmaceutical composition for treating or preventing cancer, preferably blood cancer, more preferably a disease causing neoplastic growth of plasma cells (e.g., myeloma or multiple myeloma) is the antibody (I).

The compound library is not particularly limited, and an existing library may be used. The compound library is preferably an antibody library, and the library preferably includes hybridomas generated using antibody-producing cells, such as B-cells, obtained from an animal immunized with a desired antigen.

Here, the desired antigen is not particularly limited, and is preferably, for example, the region of the amino acid residue positions 20 to 109 of the human integrin $\beta_7$. The desired antigen is more preferably active-form human integrin $\beta_7$.

A method of selecting the candidate substance is not particularly limited. For example, there may be adopted means involving: selecting a candidate substance that specifically binds to human integrin $\beta_7$; confirming that the candidate substance binds to a peptide fragment corresponding to the region of the amino acid residue positions 20 to 109 of the human integrin $\beta_7$, through use of commonly used immunoassay means; and selecting such candidate substance.

In addition, there may be adopted means involving: selecting a candidate substance that specifically binds to the human integrin $\beta_7$; further confirming a candidate substance that binds to cells expressing the chimeric integrin $\beta_7$ in which only the region of the amino acid residue positions 20 to 109 of integrin $\beta_7$ is of human origin and the rest is of non-human origin, such as mouse origin, described in detail in the antibody (I), through use of commonly used immunoassay means; and selecting such candidate substance. Means involving selecting such candidate substance may also be adopted.

In addition, there may also be adopted means involving: selecting a candidate substance that specifically binds to the human integrin $\beta_7$; further treating cells expressing the chimeric integrin $\beta_7$ in which only the region of the amino acid residue positions 20 to 109 of integrin $\beta_7$ is of human origin and the rest is of non-human origin, such as mouse origin, described in detail in the antibody (I) with a phorbol ester, a manganese salt, or the like, and confirming a candidate substance showing an increased degree of binding after the treatment as compared to that before the treatment; and selecting such candidate substance.

In addition, there may also be adopted means involving: selecting a candidate substance that specifically binds to the human integrin $\beta_7$; further generating cells expressing the chimera in which a region of the amino acid residue positions 111 to 378 of the human integrin $\beta_7$ is replaced with one of mouse origin described in detail in the antibody (I), and a chimera in which a region of the amino acid residue positions 110 to 721 of the human integrin $\beta_7$ is replaced with one of mouse origin; confirming a candidate substance showing a higher degree of bind for the former; and selecting such candidate substance.

Further, the screening method (X) may also include a step of selecting a candidate substance through use of the presence of cytotoxic activity as an indicator. Specific cells serving as a target on which the cytotoxic activity is to be confirmed are not particularly limited. Examples thereof may include blood cells expressing active-form integrin $\beta_7$ of human origin having a feature in the PSI domain of the human integrin $\beta_7$ described above.

Here, when the candidate substance to be screened is an antibody, the step of selecting a candidate substance through use of the presence of cytotoxic activity as an indicator may be a step of selecting an antibody having ADCC activity or CDC activity.

The candidate substance to be selected by the screening method (X) as described above is preferably an antibody, more preferably a monoclonal antibody. The candidate substance to be selected is most preferably the antibody (I).

(XI) Diagnosis Method

A diagnosis method (XI) is a diagnosis method for cancer, and includes a step of bringing a sample collected from a subject into contact with the antibody (I).

The subject may be the same as the subject described in detail in the treatment or prevention method (VIII) for a disease.

The sample collected from a subject may be blood or bone marrow fluid.

A specific diagnosis method is not particularly limited, but may involve, for example, judging that the subject has developed, or has a risk of developing, cancer when cells that bind to the antibody (I) are detected.

A person skilled in the art can easily determine the degree of binding by adopting a commonly used immunoassay method. Any one of whether the subject has developed cancer and whether the subject has a risk of developing cancer may be determined depending on the degree measured here.

Specific diagnosis of cancer is not particularly limited, but, for example, the subject may be diagnosed as having developed, or having a risk of developing, blood cancer, more preferably a disease causing neoplastic growth of plasma cells (e.g., myeloma or multiple myeloma) when cells that bind to the antibody (I) are plasma cells.

(XII) Kit

A kit (XII) is a kit for diagnosis of cancer, including the antibody (I).

The cancer is not particularly limited, and may be as described in detail in the above-mentioned pharmaceutical composition (VII), and is preferably blood cancer, more preferably a disease causing neoplastic growth of plasma cells (e.g., myeloma or multiple myeloma).

The kit (XII) may be appropriately accompanied by a manual. In such manual, the method described in detail in the above-mentioned diagnosis method (XI) may be described to serve as a criterion for the diagnosis of cancer.

EXAMPLES

Now, Examples for describing the present invention in more detail are described. Needless to say, the present invention is not limited to Examples described below.

Test Method: Flow Cytometry and Sorting

In the following Examples, flow cytometry (FACS) used for selecting cells was performed in the following manner.

Bone marrow mononuclear cells collected from an ilium of a myeloma patient who had given informed consent were suspended in an ACK solution (150 mM $NH_4Cl$ and 10 mM $KHCO_3$), and the whole was left at rest at 4° C. for 3 minutes to remove red blood cells. The bone marrow mononuclear cells after the removal were washed with PBS supplemented with 2% fetal bovine serum, and then, in order to prevent the binding of a non-specific antibody, blocking was performed at 4° C. for 20 minutes in PBS containing 10% human AB serum.

After that, each antibody (see below) labeled with a fluorescent dye was added thereto to perform staining at 4° C. for 30 minutes. After that, the cells were washed with PBS, and then suspended in PBS containing 1 µg/ml propidium iodide (PI), followed by FACS analysis. The analysis of the cells and cell sorting were performed using FACS Aria Cell Sorter (manufactured by Becton Dickinson Immunocytometry Systems).

For the staining of the cells, the following monoclonal antibodies were appropriately selected and used.

APC-conjugated anti-human CD34 antibody (manufactured by BD Pharmingen)

PE-Cy7-conjugated anti-human CD34 antibody (manufactured by BD Pharmingen)

APC/Cy7-conjugated anti-human CD19 antibody (manufactured by Biolegend)

FITC-conjugated anti-human CD38 antibody (manufactured by eBioscience)

APC-conjugated anti-human CD138 antibody (manufactured by Biolegend)

PE/Cy7-conjugated anti-human CD3 antibody (manufactured by Biolegend)

FITC-conjugated anti-human CD14 antibody (manufactured by BD Pharmingen)

PE/Cy7-conjugated anti-human CD45 antibody (manufactured by Biolegend)

Example 1

Generation of Monoclonal Antibody Library that Binds to Myeloma Cell Line and does not Bind to Healthy Person Peripheral Blood In antibody therapy against multiple myeloma, it is important to use an antibody that binds to myeloma cells but does not bind to normal blood cells. In view of this, such antibody was identified by the following method. First, 10,000 clones or more of monoclonal antibodies that bound to various myeloma cell lines were generated using the following technique.

Balb/c mice were immunized at the footpad twice a week for from 2 weeks to 3 weeks through use of six kinds of human myeloma cell lines (MM.1s cells, RPMI8226 cells, INA6 cells, U266 cells, OPM2 cells, and KMS12BM cells) as antigens. After that, a lymph node below the knee was removed, and a cell suspension was generated and subjected to cell fusion with a SP2/0 mouse myeloma cell line to generate hybridomas. The cell fusion was performed using a method using polyethylene glycol (PEG method). After that, the cells were cultured in hypoxanthine-aminopterin-thymidine medium (HAT medium) to select hybridomas (>10,000 clones).

Finally, through use of culture supernatants of the hybridomas, a supernatant including antibodies that bound to the myeloma cell line used for the immunization and did not bind to healthy person peripheral blood-derived mononuclear cells was selected using FACS. Antibody candidates specific to myeloma cells obtained as a result of the foregoing were about 200 clones, and the hybridomas expressing those antibody candidates were grown and then cryopreserved.

Example 2

Identification of Antibody that Specifically Binds to Myeloma Cells in Human Multiple Myeloma Patient Bone Marrow About 200 clones of candidate antibodies obtained in Example 1 described above were used to stain myeloma patient-derived bone marrow cells, followed by analysis using FACS.

Each candidate antibody was added to multiple myeloma patient-derived bone marrow cells, and the cells were incubated at 4° C. for 30 minutes and then washed. A PE-conjugated anti-mouse IgG antibody was added as a secondary antibody, and the cells were further incubated at 4° C. for 30 minutes. After washing, finally, the cells were stained using an APC-conjugated anti-human CD138 antibody, FITC-conjugated anti-human CD38, or PE/Cy7-conjugated anti-human CD45. As a negative control, a sample having added thereto an isotype control in place of the candidate antibody was prepared as the same time.

Those cells were analyzed using FACS to select an antibody that bound to $CD45^-CD38^{++}CD138^+$ myeloma plasma cells and $CD45^-$ $CD38^{++}CD138^-$ myeloma progenitor cells, but did not bind to $CD45^+$ blood cells.

Figure 2:
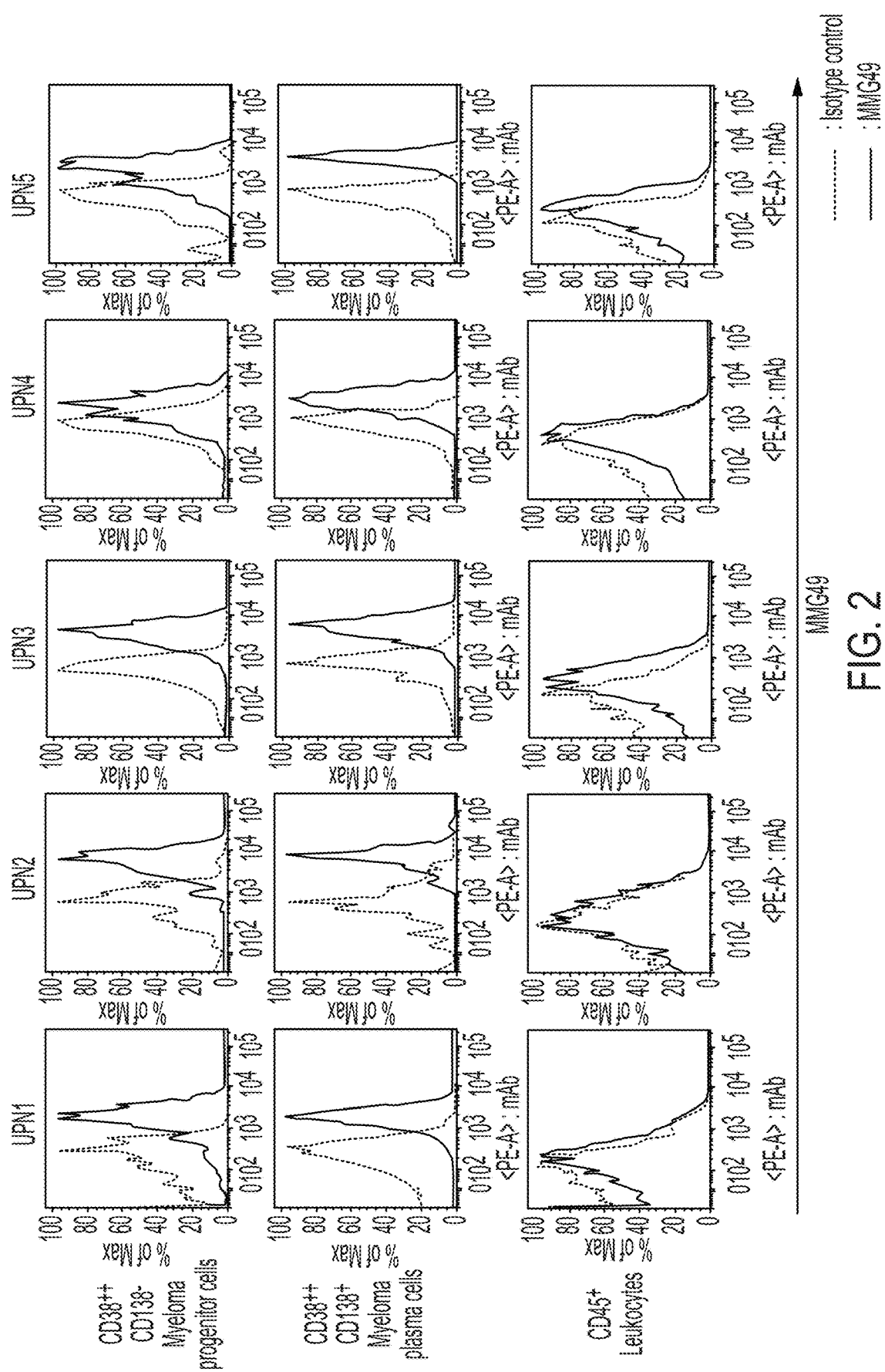
FIG. 2 shows graphs for results obtained in Example 2 by analyzing, by FACS, the binding of the MMG49 antibody to the myeloma progenitor cell fraction, myeloma plasma cell fraction, and CD45$^+$ leukocytes of a plurality of myeloma patient-derived bone marrow cells (UPN1 to UPN5).

As a result, an MMG49 antibody was identified as an antibody satisfying the above-mentioned condition (FIG. 1 and FIG. 2). In each histogram in the figures, the Y-axis represents the number of cells, and the X-axis represents the binding strength of the MMG49 antibody.

Example 3

Identification of Antigen Protein to which MMG49 Antibody Binds

An antigen protein to which the MMG49 antibody bound was identified by an expression cloning method.

First, a cDNA library was generated from MM.1s cells, to which the MMG49 antibody was known to bind, using a superscript choice system for cDNA synthesis (Invitrogen), and was inserted into a pMXs retrovirus vector (donated by Professor Toshio Kitamura at the Institute of Medical Science of the University of Tokyo) using a BstXI adaptor (Invitrogen). The thus generated cDNA library was introduced into plat-E cells (donated by Professor Toshio Kitamura), and BaF3 cells were infected with the resultant retrovirus. Thus, BaF3 cells expressing an MM.1s-derived cDNA library were obtained.

Figure 3:
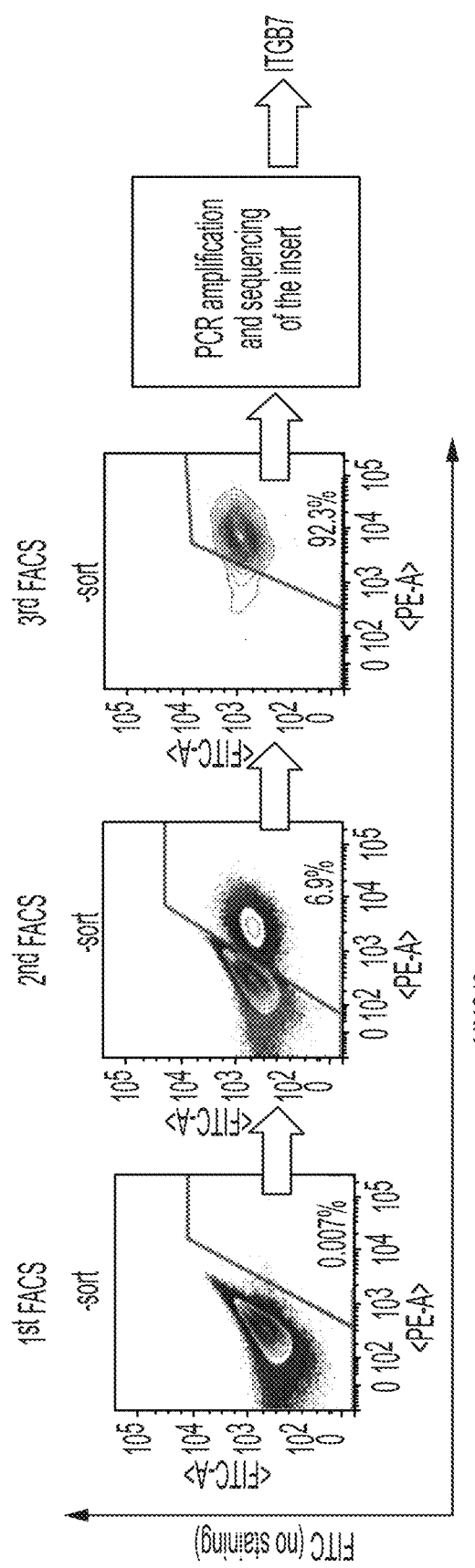
FIG. 3 is an illustration of a process of identifying an antigen protein recognized by the MMG49 antibody by an expression cloning method in Example 3. There is illustrated a process of concentrating BaF3 cells that bind to the MMG49 antibody, from an initial concentration of 0.1% or less, by FACS sorting.

Next, the cells were repeatedly concentrated by staining the cells with the MMG49 antibody and sorting positive cells by FACS (FIG. 3). After the third sorting, most cells were cells that bound to the MMG49 antibody. Then, the retrovirus insert carried by those cells was amplified by PCR, and then sequenced to identify its base sequence. As a result, it was revealed that the insert carried by the cells was ITGB7.

Example 4

Confirmation that Antigen to which MMG49 Antibody Binds is ITGB7-Expressed Protein by Generation of ITGB7-Deficient Myeloma Cells An ITGB7-deficient U266 myeloma cell line was generated using a Crisp-cas9 system.

First, a vector was generated by inserting a double-stranded DNA sequence serving as an ITGB7-specific target sequence into a PX330 (addgene) vector. The vector was introduced together with a linear hygromycin-resistance gene expression vector (Clontech) serving as a vector for drug selection into U266 cells through use of Nucleofector (trademark) II (Lonza). After that, for clones that had grown in a medium supplemented with hygromycin, the expression of ITGB7 was stained using an FIB27 antibody (anti-integrin $\beta_7$ antibody; Biolegend), followed by analysis by FACS, to thereby identify ITGB7-deficient cells.

Figure 4:
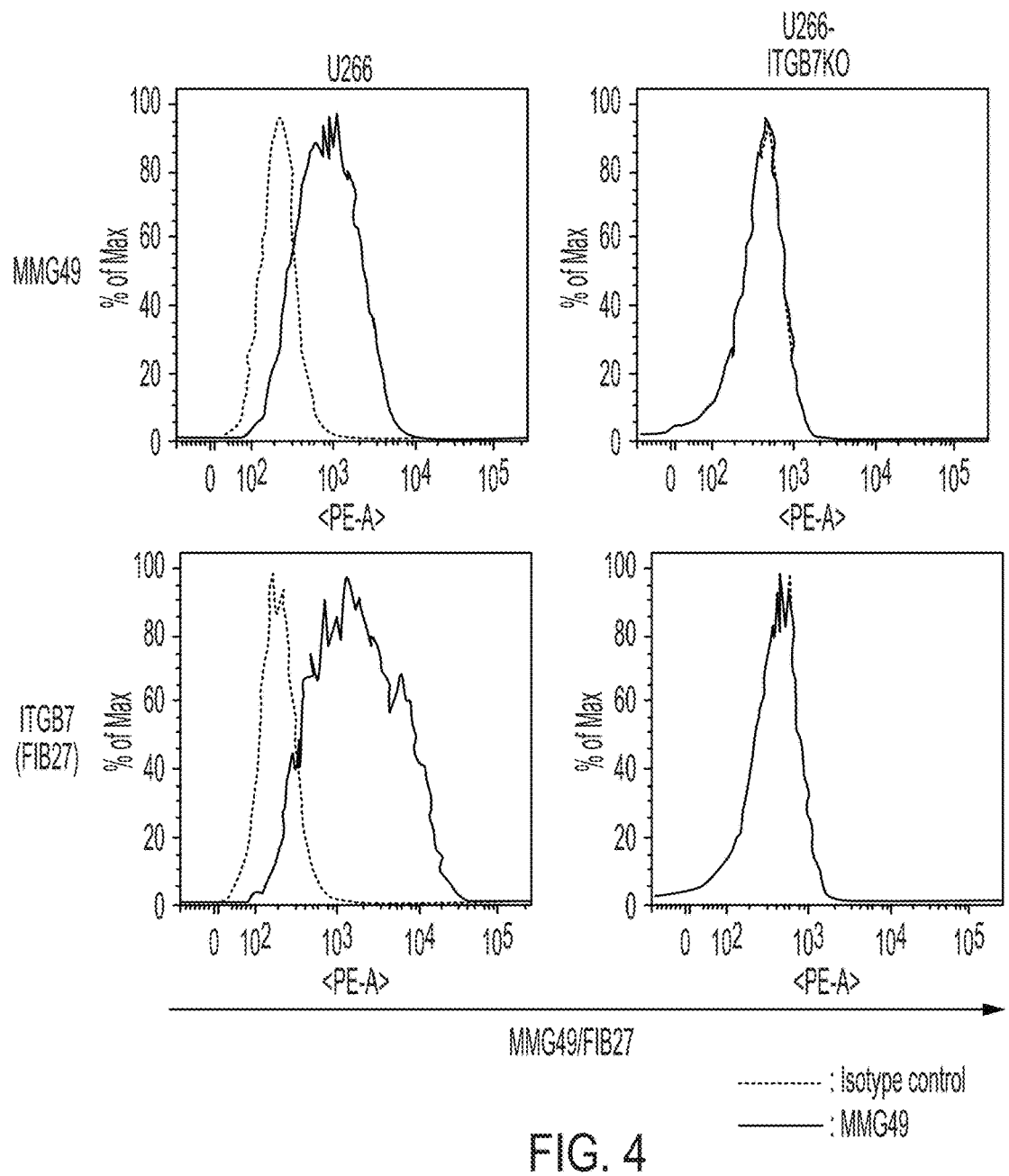
FIG. 4 shows graphs for results obtained in Example 4 by staining ITGB7-deficient U266 cells generated using a Crisp-cas9 system with the MMG49 antibody or an FIB27 antibody (commercially available anti-integrin $\beta_7$ antibody), followed by FACS analysis.

Next, the resultant ITGB7-deficient cells were stained using the MMG49 antibody and analyzed by FACS. As a result, it was found that the MMG49 antibody bound to wild-type U266 cells, whereas the binding of the MMG49 antibody had completely disappeared in the ITGB7-deficient strain (FIG. 4). This shows that MMG49 is bound to only the ITGB7-expressed protein (integrin $\beta_7$).

Figure 5:
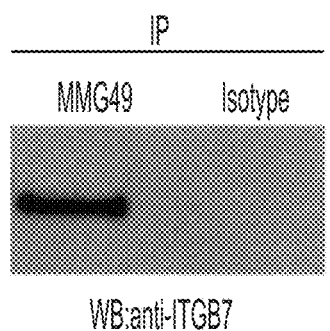
FIG. 5 is an image for showing results obtained in Example 4 by subjecting a product immunoprecipitated from a cell lysate derived from MM1s myeloma cells with the MMG49 antibody or an isotype control antibody, to SDS-PAGE, and then performing western blot with a commercially available anti-integrin $\beta_7$ antibody (Abcam plc).

Next, immunoprecipitation from a lysate of MM1s myeloma cells was performed using the MMG49 antibody, followed by SDS-PAGE. Subsequently, WB was performed using an anti-integrin $\beta_7$ antibody (Miltenyi). As a result, integrin $\beta_7$ was detected in the product immunoprecipitated with the MMG49 antibody (FIG. 5). This shows that the MMG49 antibody is bound to the integrin $\beta_7$.

Example 5

Measurement of Binding Pattern of MMG49 Antibody in Cell Fractions of Healthy Person Peripheral Blood and Myeloma Patient Bone Marrow Through use of a commercially available anti-integrin $\beta_7$ antibody (FIB27 antibody; Biolegend) and the MMG49 antibody, binding to various cell fractions in healthy person peripheral blood and bone marrow cells was measured.

Red blood cells were removed from healthy person-derived peripheral blood cells using HES40, and then an Fc receptor blocking reagent (Miltenyi) was added to block non-specific antibody binding. After that, the MMG49 antibody or the FIB27 antibody, or mouse IgG2a serving as an isotype control was added, and the cells were incubated at 4° C. for 30 minutes and then washed. A PE-conjugated anti-mouse IgG antibody was added as a secondary antibody, and the cells were further incubated at 4° C. for 30 minutes.

The resultant cells were washed, and then, finally, stained using an APC/Cy7-conjugated anti-human CD19 antibody, an FITC-conjugated anti-human CD14 antibody, or a PE/Cy7-conjugated anti-human CD3 antibody. The cells after the staining were analyzed using FACS, to thereby measure the binding of the MMG49 antibody and the FIB27 antibody in each fraction (FIG. 6).

Figure 6A:
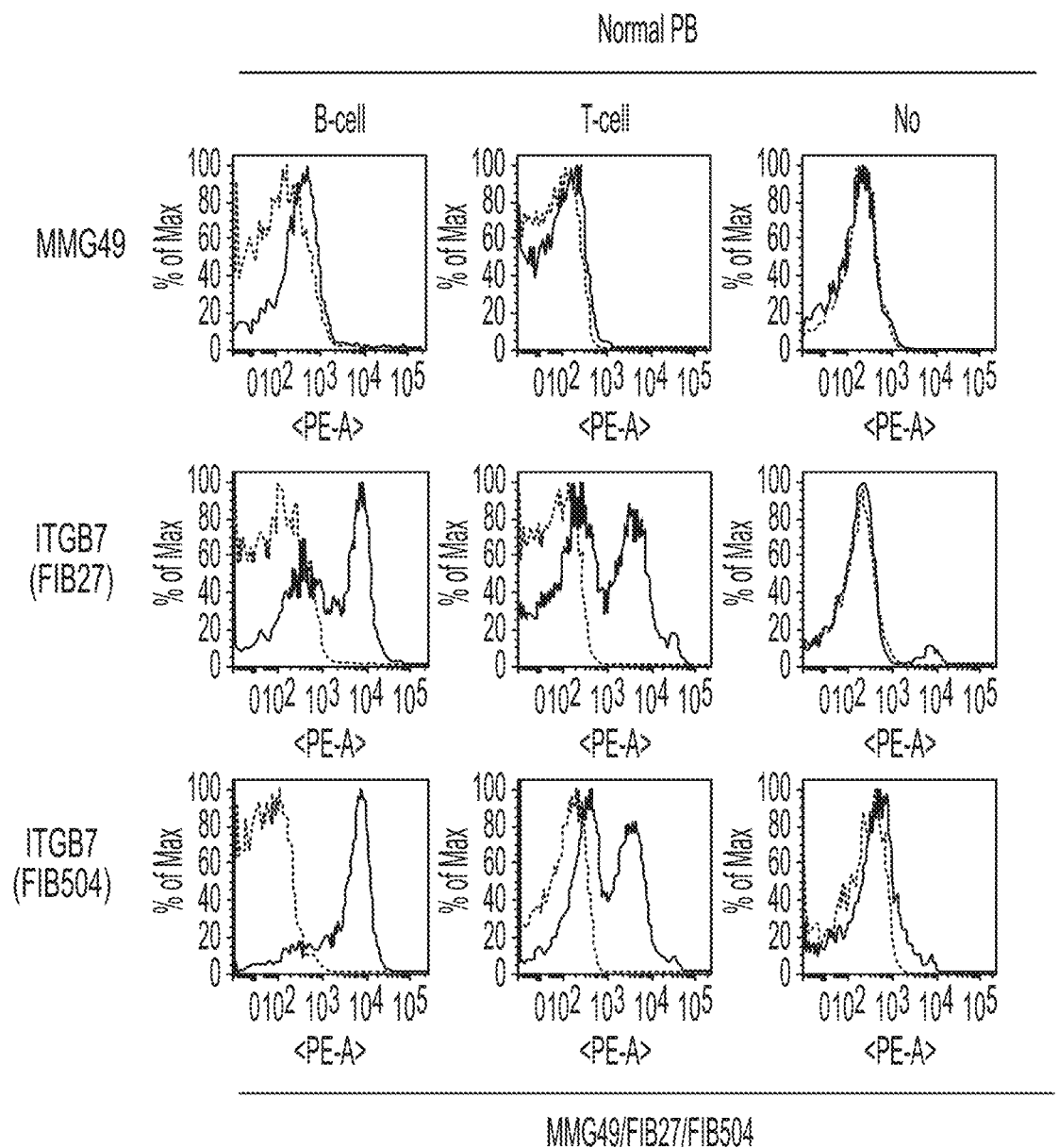
FIGS. 6A and 6B are graphs showing results obtained in Example 5 by analyzing the binding of each of the MMG49 antibody, the FIB27 antibody, and an FIB504 antibody to each cell fraction of healthy person peripheral blood cells (in the figures, B-cells, T-cells, monocytes, neutrophils, red blood cells, and platelets are shown in the stated order from the left-hand side) through use of FACS.
Figure 6B:
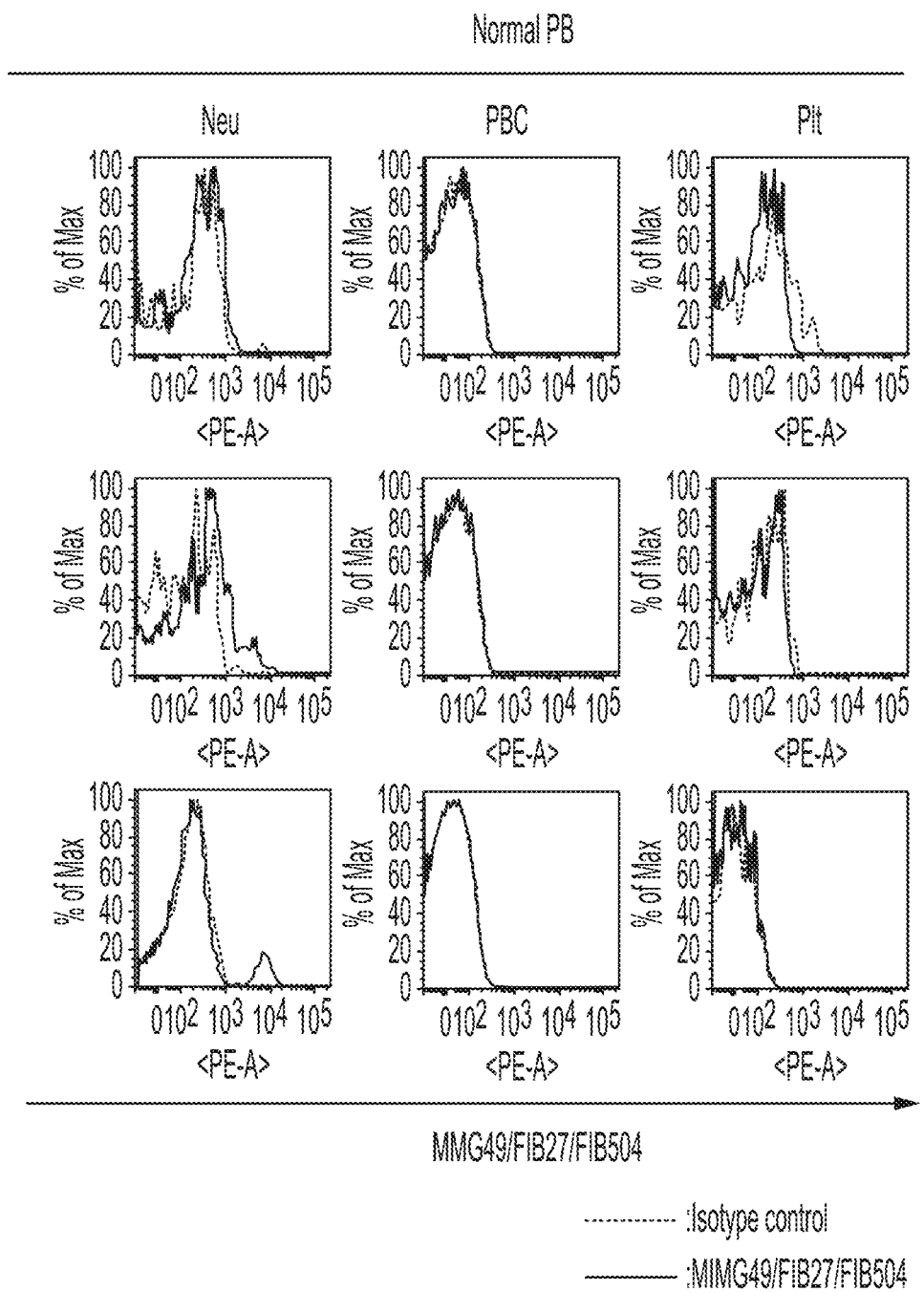

In addition, 100 µl of PBS (containing EDTA) supplemented with 1 µl of peripheral blood of a healthy person was similarly stained using the MMG49 antibody or the FIB27 antibody, and finally stained using a Pacific blue-conjugated anti-human CD235 antibody (BD Pharmingen) or an FITC-conjugated anti-human CD41antibody (BD Pharmingen), and thus the presence or absence of the binding of each antibody to CD235$^+$ red blood cells and platelets was also similarly investigated by FACS analysis (FIG. 6). The results of the foregoing show that the FIB27 antibody strongly binds to many lymphoid cells, whereas the binding of the MMG49 antibody to the above-mentioned normal blood cells is extremely weak.

Figure 7A:
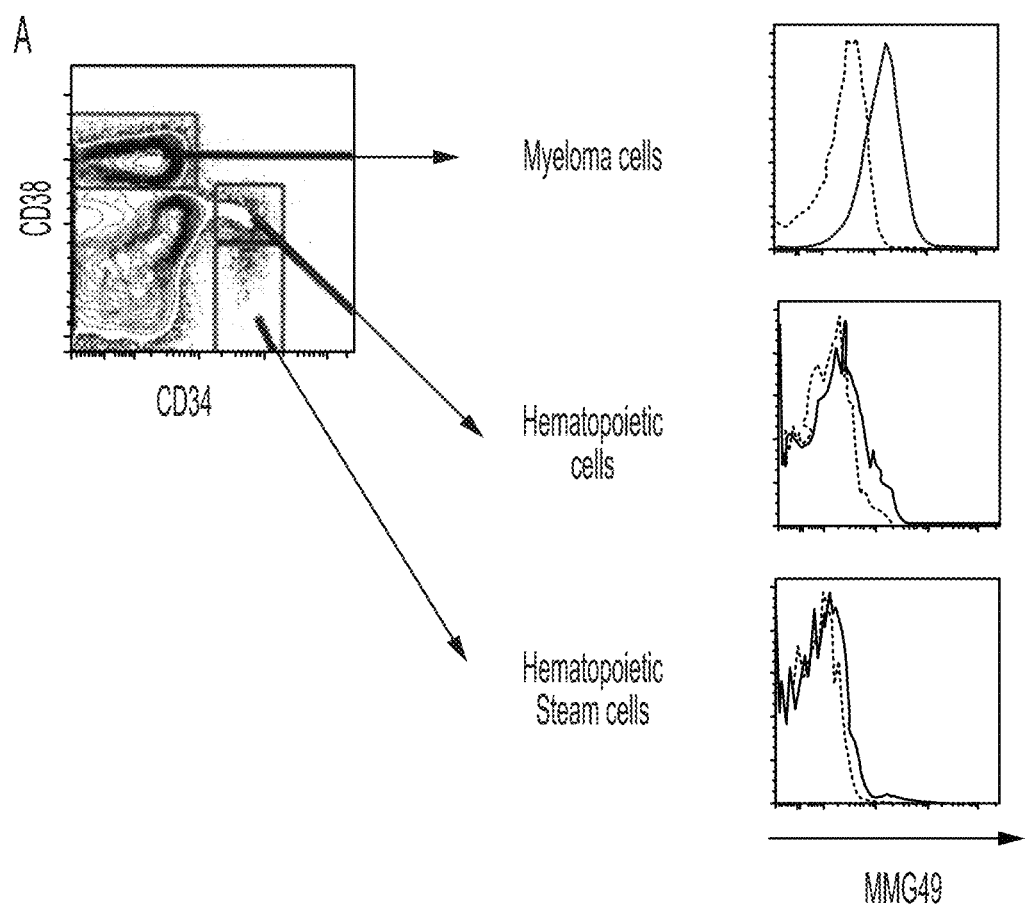
FIGS. 7A and 7B are graphs showing results obtained in Example 5 by analyzing, by FACS, the binding of the MMG49 antibody to each of cell fractions of myeloma patient-derived bone marrow cells. On the left-hand side, a method of identifying each cell fraction is illustrated, and on the right-hand side, graphs for showing the binding of MMG49 to each fraction are shown.
Figure 7B:
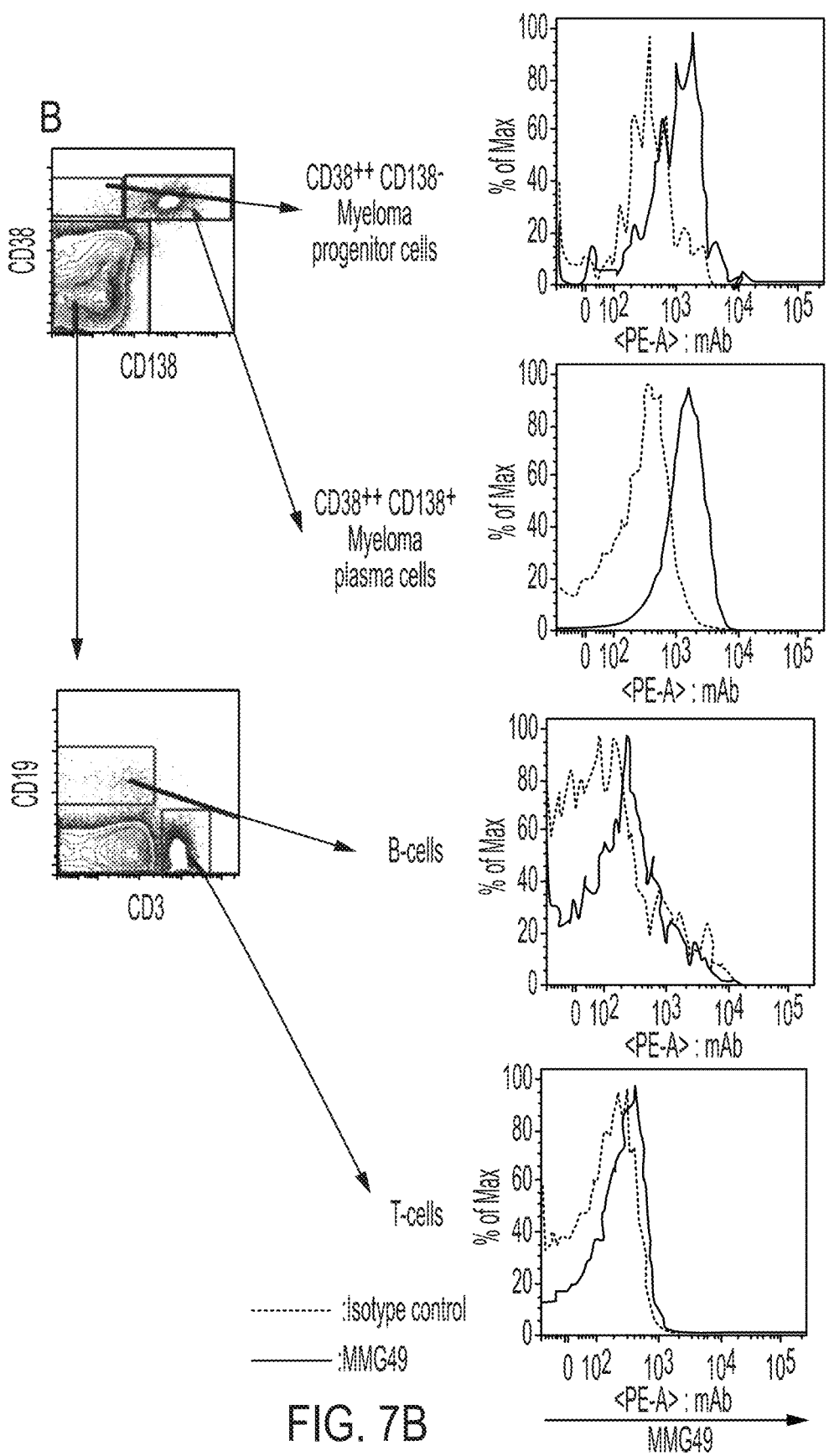

Further, in order to elucidate whether the binding of the MMG49 antibody to each normal cell fraction except for myeloma cells was absent in bone marrow, bone marrow cells of a myeloma patient were also similarly stained using the MMG49 antibody, and finally stained using an APC-conjugated anti-human CD34 antibody (manufactured by BD Pharmingen), Alexa647-conjugated human CD3 (manufactured by BD Pharmingen), a Cy7APC-conjugated anti-CD19 human antibody (manufactured by BD Pharmingen), a PE-Cy7-conjugated anti-CD38 human antibody (manufactured by BD Pharmingen), or an FITC-conjugated anti-CD14 human antibody (manufactured by BD Pharmingen). Those myeloma patient-derived bone marrow cells after the staining were analyzed using FACS, and thus the binding of the MMG49 antibody in each fraction was measured (FIG. 7). The results of the foregoing show that the MMG49 antibody strongly binds to myeloma cells, but hardly binds to all normal blood cells including hematopoietic stem cell and progenitor cell fractions.

Example 6

Analysis of Binding of MMG49 to Various Cell Lines

The binding of the MMG49 antibody and the FIB27 antibody in various cell lines (MM1s cells, U266 cells, RPMI8226 cells, and JJN3 cells) was analyzed using FACS. A staining method is the same as in the case of peripheral blood or the like described above in Example 5.

Figure 8:
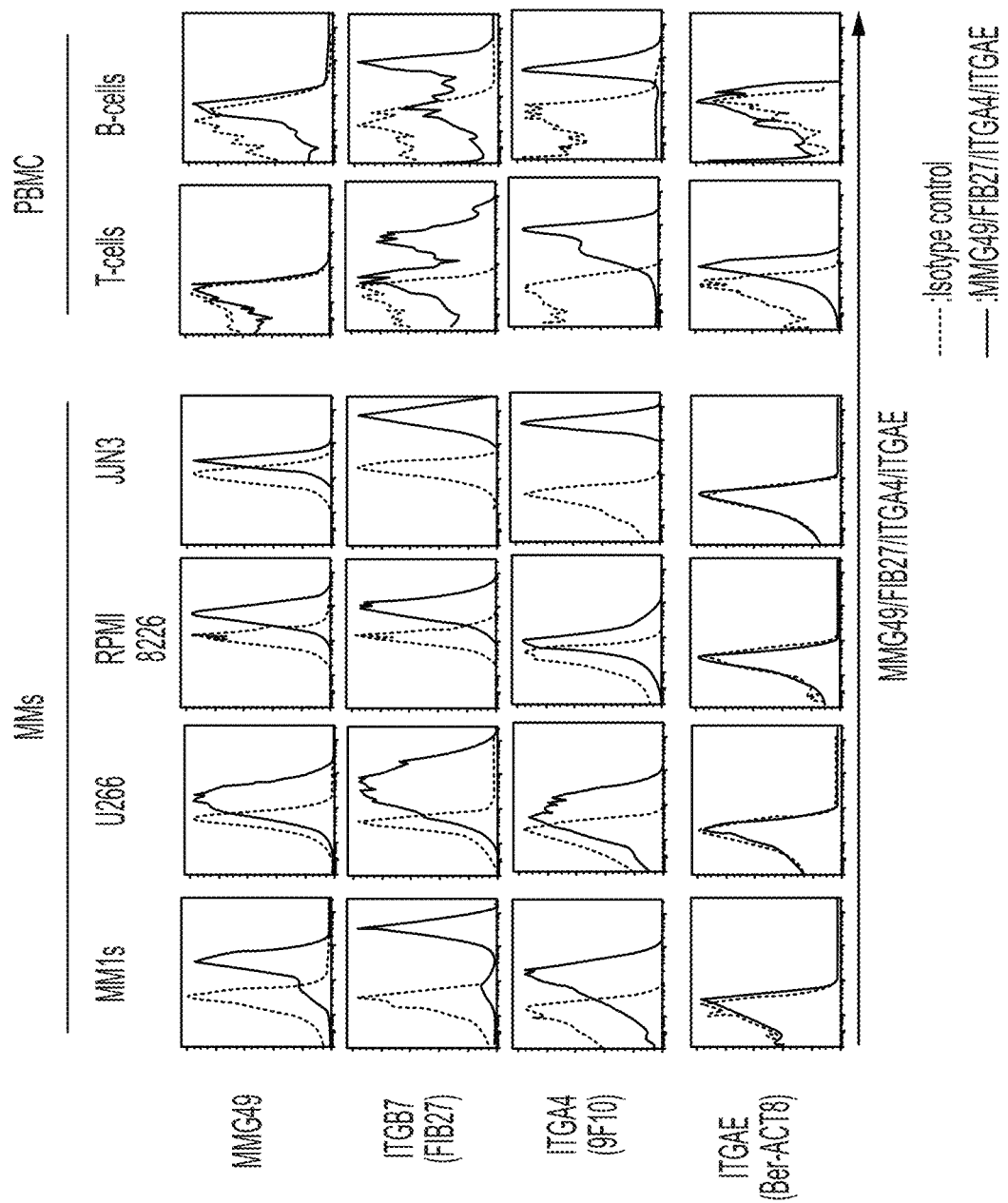
FIG. 8 is graphs showing results obtained in Example 6 by analyzing the binding of each of the MMG49 antibody and the FIB27 antibody to each of various myeloma cell lines, and T-cells and B-cells derived from peripheral blood through use of FACS. There are also shown results of confirming the expression of ITGA4 (binding of an anti-integrin $\alpha_4$ antibody) and the expression of ITGAE (binding of an anti-integrin $\alpha_E$ antibody) in the above-mentioned cells by FACS analysis.
Figure 9:
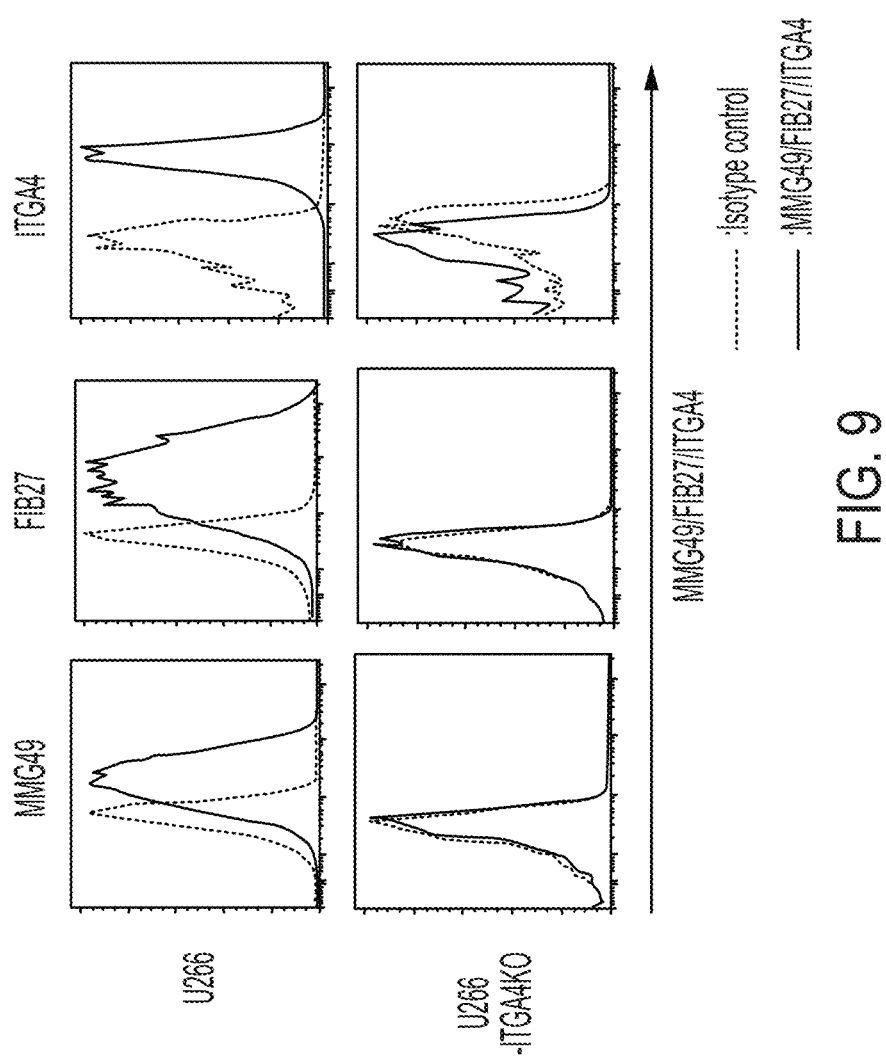
FIG. 9 is graphs showing results obtained in Example 6 by analyzing, by FACS, the binding of the MMG49 antibody and the FIB27 antibody to U266 cells and ITGA4 (integrin $\alpha_4$)-deficient U266 cells. There are also shown results obtained by analyzing, by FACS, the expression of ITGA4 (binding of the anti-integrin $\alpha_4$ antibody) in the above-mentioned cells.

Integrin $\beta_7$ is known to form a heterodimer with integrin $\alpha_4$ or integrin $\alpha_E$ and be expressed on a cell surface. Therefore, the expression thereof was also analyzed at the same time using FACS, with an Alexa647-conjugated anti-human CD49d antibody (Biolegend) and an APC-conjugated anti-human CD103 antibody (Biolegend). CD103 represents the integrin $\alpha_E$, and CD49d represents the integrin $\alpha_4$. In the same manner as in Example 5 described above, the expression levels of the integrin $\alpha_E$ and the integrin $\alpha_4$ in healthy person-derived peripheral blood were also investigated (FIG. 8).

As a result, ITGA4 was expressed in most of the myeloma cell lines, and ITGAE was expressed in none of the cell lines. The FIB27 antibody was bound to all myeloma cell lines, but the binding of the MMG49 antibody did not coincide with the expression level of the FIB27 antibody. Further, the binding of the MMG49 antibody or the FIB27 antibody to ITGA4-deficient U266 cells generated using a Crisp-cas9 system was investigated by FACS, and as a result, it was found that the binding of both the antibodies to U266 cells had disappeared due to ITGA4 deficiency. That is, it was found that both the MMG49 antibody and the FIB27 antibody recognized $\beta_7$ integrin expressed as $\alpha_4\beta_7$ integrin.

Example 7

Analysis of Correlation between Activation of Integrin and Binding of MMG49 Antibody In consideration of the unique binding manner of the MMG49 antibody described above, it was supposed that the MMG49 antibody recognized integrin $\beta_7$ that had been changed in structure through activation.

In view of the foregoing, K562 cells caused to forcibly express $\alpha_4\beta_7$ and human normal peripheral blood CD4T-cells concentrated using a CD4 T-cell enrichment kit (BD pharmingen) were washed with 5 mM EDTA/HBS, and then incubated in 1 mM Ca$^{2+}$/1 mM Mg$^{2+}$/HBS (buffer for low activity) or 2 mM Mn$^{2+}$/HBS (activating buffer) together with the MMG49 antibody or the FIB27 antibody at room temperature for 30 minutes, followed by washing. A PE-conjugated anti-mouse IgG antibody was added as a secondary antibody, and the cells were further incubated at room temperature for 30 minutes. The resultant cells were analyzed using FACS, to thereby measure the binding of the MMG49 antibody and the FIB27 antibody in cells in which the integrin $\alpha_4\beta_7$ had been activated.

Figure 10A:
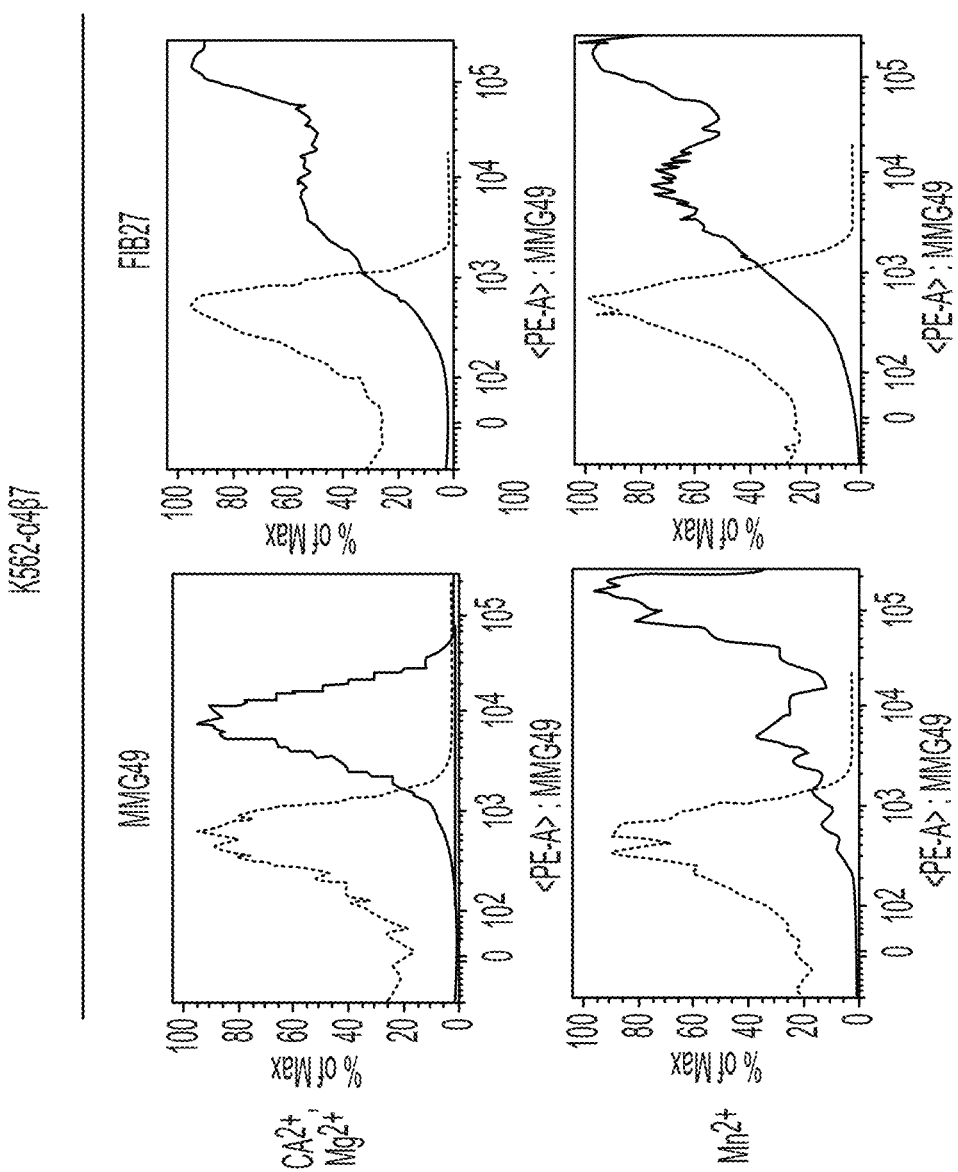
FIGS. 10A and 10B are graphs showing results obtained in Example 7 by allowing integrin $\alpha_4\beta_7$-forcibly expressing K562 cells and human normal peripheral blood-derived T-cells treated in the presence of $Ca^{2+}/Mg^{2+}$ or $Mn^{2+}$ at 37° C. for 20 minutes to react with the MMG49 antibody or an isotype antibody, then staining the cells using an anti-mouse IgG antibody as a secondary antibody, and subjecting the stained cells to FACS analysis.
Figure 10B:
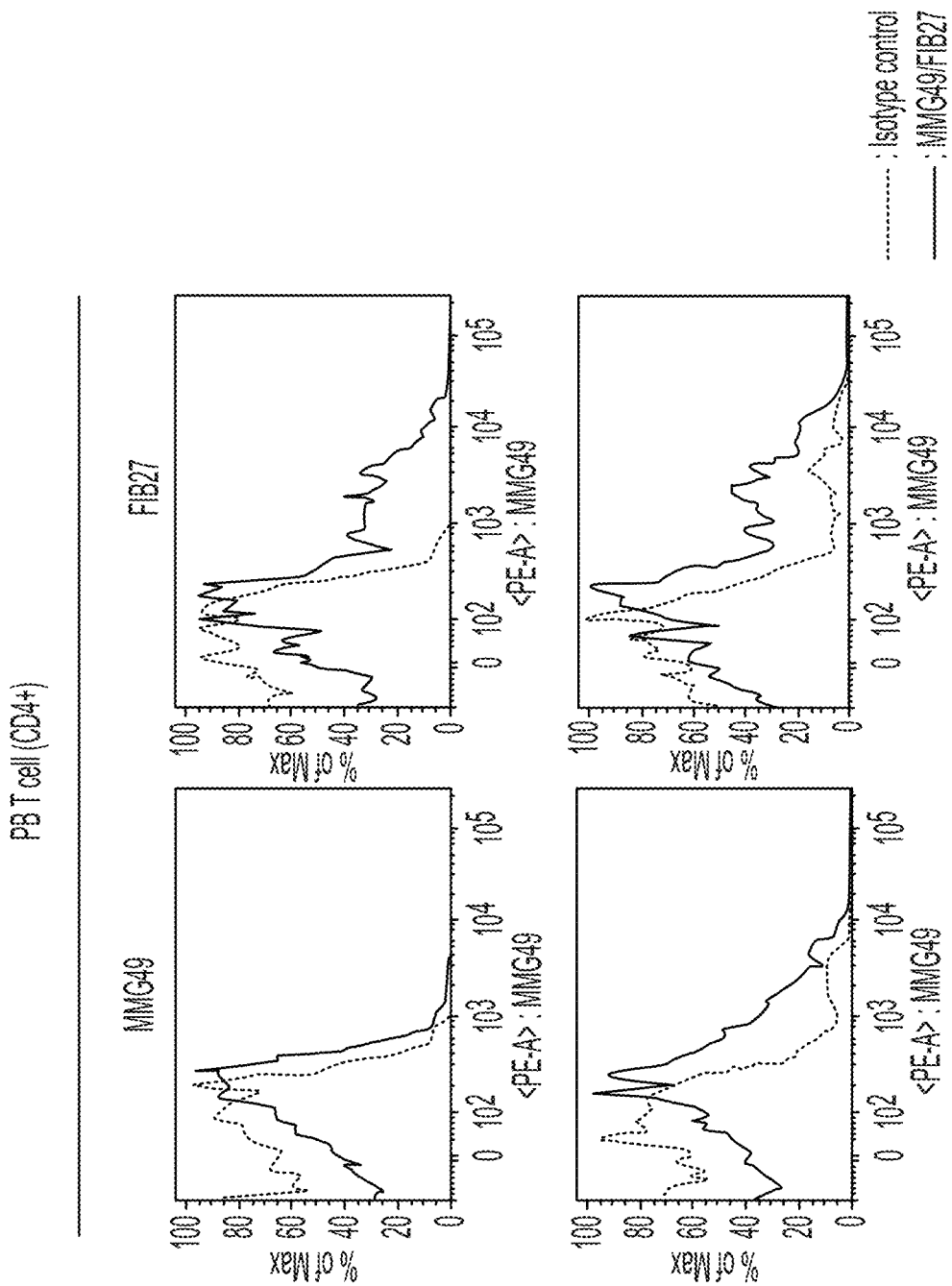

As a result, an enhancement in binding of the MMG49 antibody in the presence of Mn$^{2+}$ was observed (FIG. 10). Meanwhile, no similar change was observed for the FIB27 antibody. This suggests the possibility that the MMG49 antibody is an antibody specific to activated conformation of integrin $\beta_7$.

Example 8

Identification of Epitope essential for Recognition by MMG49 Antibody

Figure 11:
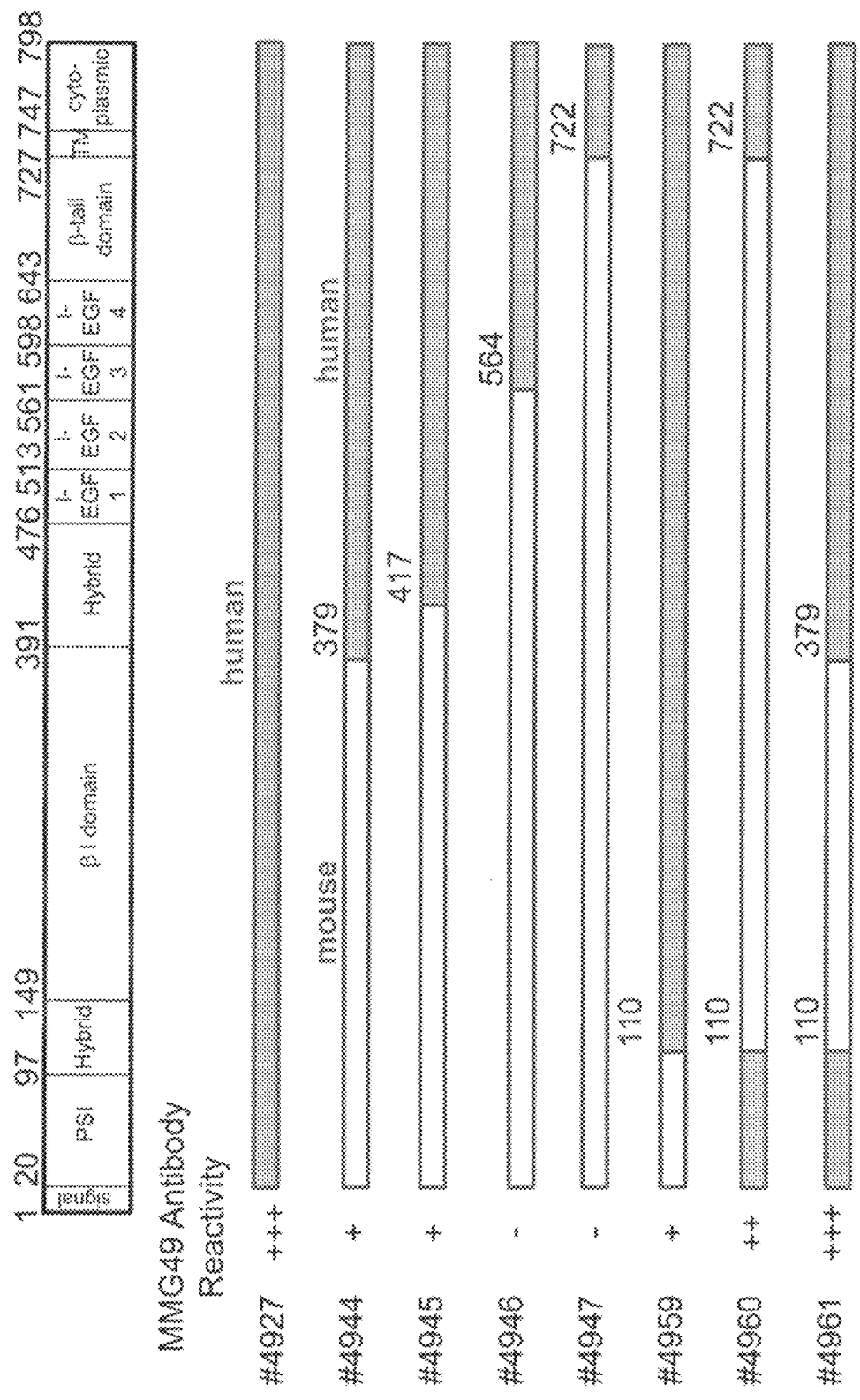
FIG. 11 is a diagram illustrating the construction of human/mouse chimeric integrin $\beta_7$ proteins and the presence or absence of the binding of the MMG49 antibody to 293T cells caused to transiently express the proteins in Example 8.

In order to identify an epitope recognized by the MMG49 antibody, vectors for expressing eight kinds of human/mouse chimeric integrin $\beta_7$ proteins as illustrated in FIG. 11 were generated using an overlapping PCR method.

Each expression vector was introduced into 293T-cells by a lipofection method, and 48 hours after that, the presence or absence of the binding of the MMG49 antibody was analyzed. The cells were suspended in PBS supplemented with 1% fetal bovine serum, the MMG49 antibody was added, and then the whole was left at rest at room temperature for 30 minutes. After washing, an Alexa488-anti-mouse IgG antibody was added, and the whole was left at rest at room temperature for 30 minutes, followed by analysis by FACS.

Figure 12A:
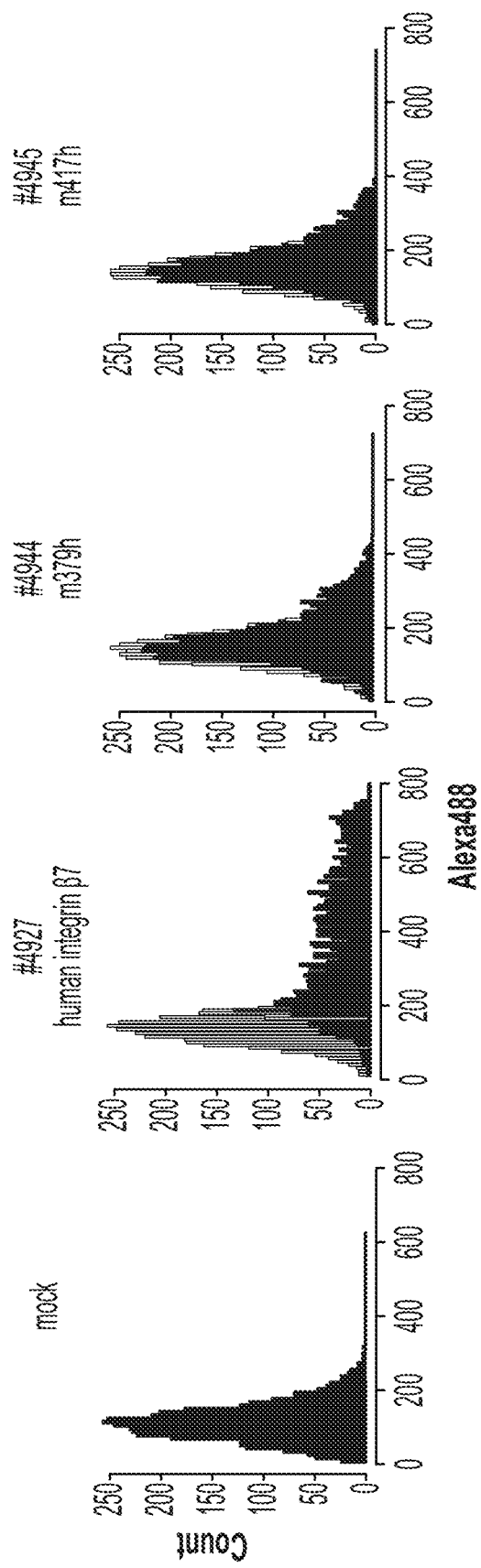
FIGS. 12A and 12B are graphs showing results obtained in Example 8 by analyzing, by FACS, the binding of the MMG49 antibody to 293T cells caused to transiently express the human/mouse chimeric integrin $\beta_7$ proteins.
Figure 12B:
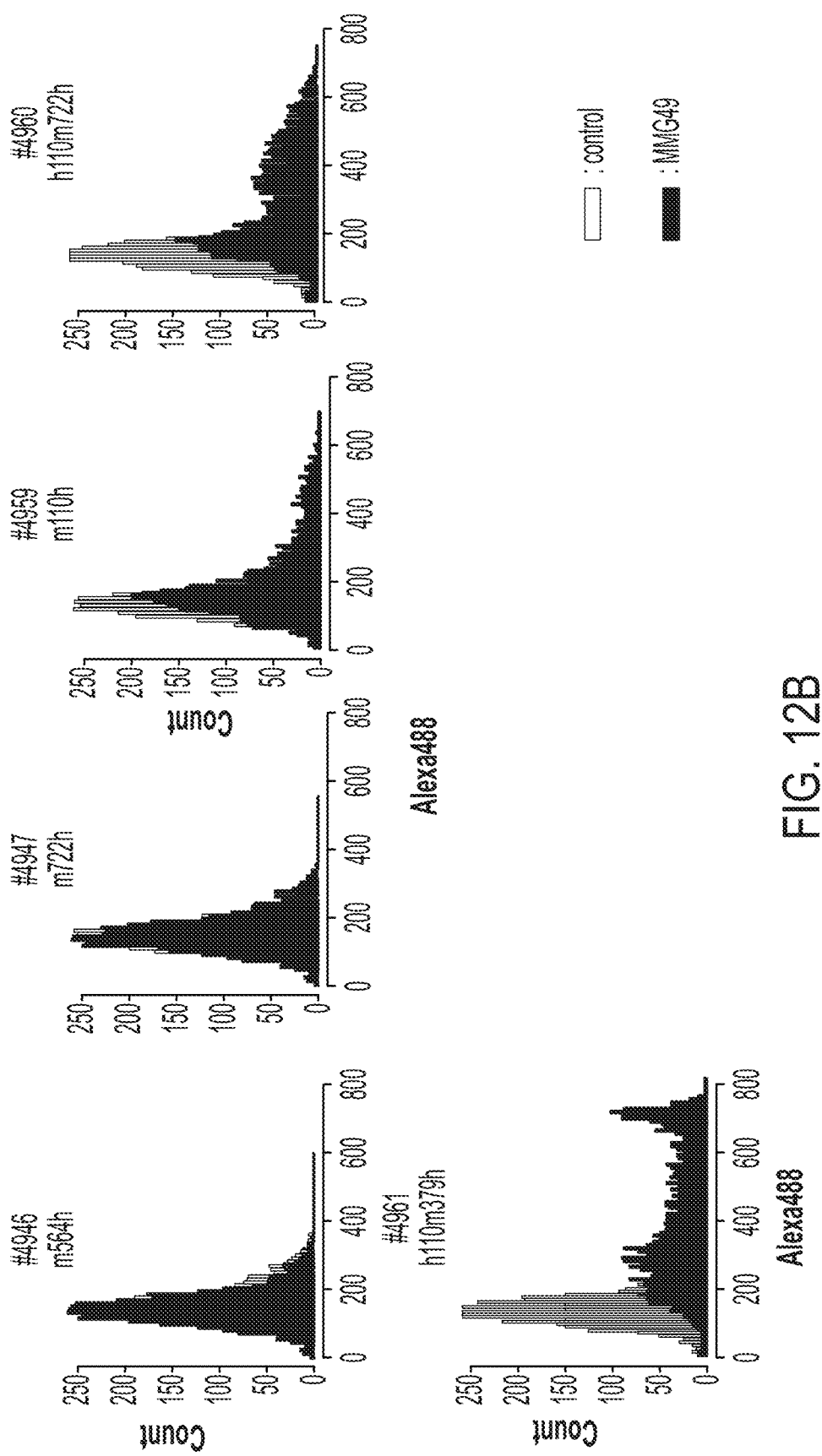
Figure 13:
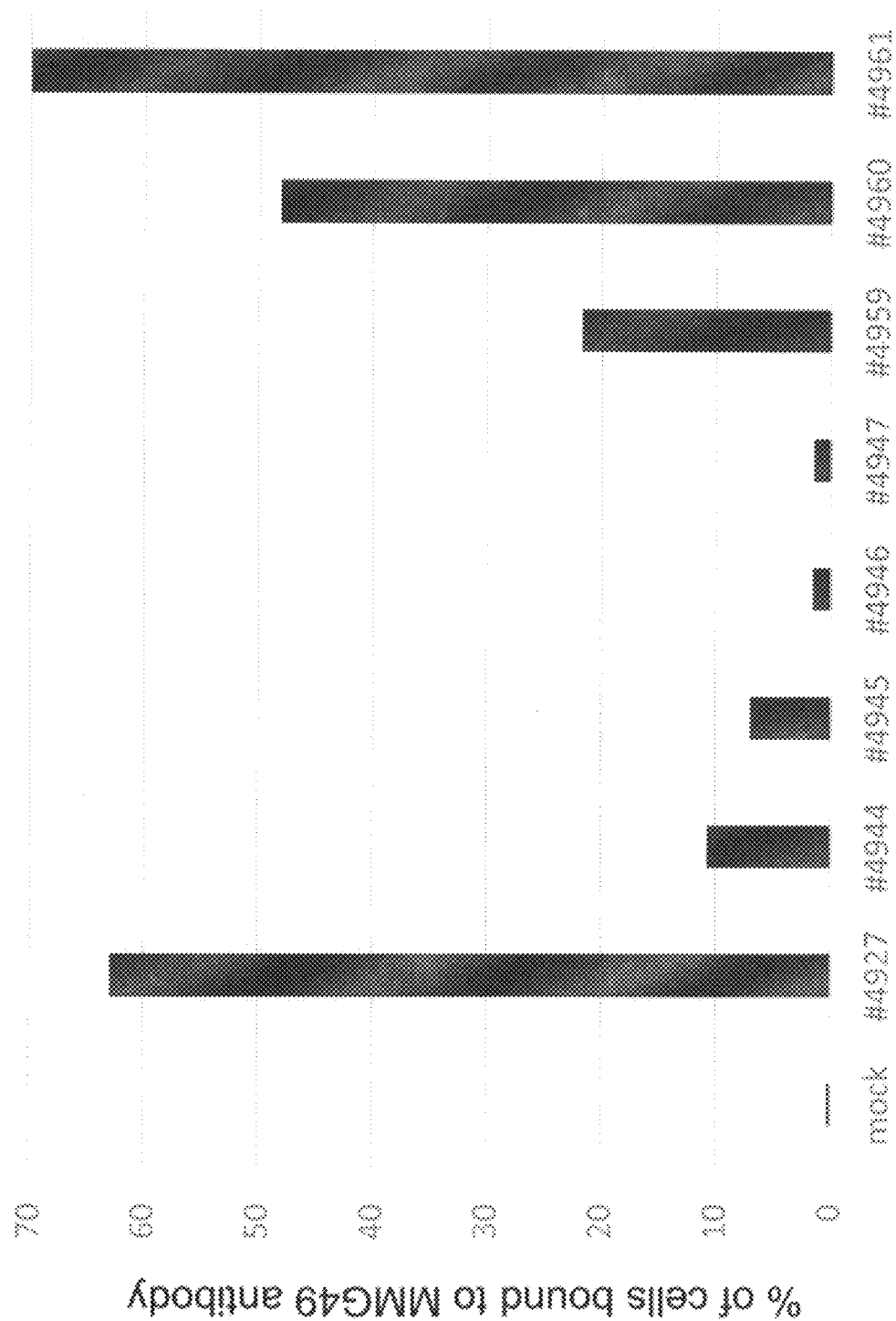
FIG. 13 is a graph summarizing the results shown in FIG. 12. In the graph in FIG. 13, the axis of ordinate represents the percentage of cells bound to the antibody, and the axis of abscissa represents various human/mouse chimeric integrin $\beta_7$ proteins.

As a result, it was revealed that the MMG49 antibody strongly bound to a chimeric integrin $\beta_7$ protein (#4960) in which a region of the amino acid residue positions 110 to 721 was of mouse origin and the rest (region of the amino acid residue positions 20 to 109 and region of the amino acid residue positions 722 to 798) had sequences of human origin in almost the same manner as in the case of a chimeric integrin $\beta_7$ protein entirely of human origin (#4927) (FIG. 11 to FIG. 13).

In view of the fact that the region of the amino acid residue positions 722 to 798 includes a transmembrane domain (TM) and an intracellular domain (cytoplasmic), and that a region of the amino acid residue positions 1 to 19 is a signal peptide, it was shown that an epitope essential for the binding of the MMG49 antibody was present in the region of the amino acid residue positions 20 to 109 including a PSI domain.

In addition, it was revealed that the MMG49 antibody had a slightly increased avidity for a chimeric integrin $\beta_7$ protein (#4961) in which a region of the amino acid residue positions 110 to 378 was of mouse origin, and in which a region of the amino acid residue positions 20 to 109 and a region of amino acid residue positions 379 to 798 were of human origin as compared to the chimeric integrin $\beta_7$ protein (#4960), and the increased avidity was at exactly the same binding level as in the case of the chimeric integrin $\beta_7$ protein entirely of human origin (#4927).

Further, it was also revealed that the MMG49 antibody had slightly increased binding capacity for a chimeric integrin $\beta_7$ protein (#4944) in which the above-mentioned region of the amino acid residue positions 20 to 109, which had been shown to include the epitope of the MMG49 antibody, and a region of the amino acid residue positions 1 to 378 including a region corresponding to a signal peptide of the amino acid residue positions 1 to 19 were of mouse origin, and in which a region of the amino acid residue positions 379 to 798 was of human origin, and a chimeric integrin $\beta_7$ protein (#4945) in which a region of the amino acid residue positions 1 to 416 was of human origin and a region of the amino acid residue positions 417 to 798 was of human origin as compared to a chimeric integrin $\beta_7$ protein (#4946) in which a region of the amino acid residue positions 1 to 563 was of mouse origin and a region of the amino acid residue positions 564 to 798 was of human origin, and a chimeric integrin $\beta_7$ protein (#4947) in which a region of the amino acid residue positions 1 to 721 was of mouse origin and a region of the amino acid residue positions 722 to 798 was of human origin.

In view of the above-mentioned experimental results, it was also revealed that the specific avidity, that is, affinity of the MMG49 antibody for the region of the amino acid residue positions 20 to 109 of the integrin $\beta_7$ was increased by the region of the amino acid residue positions 379 to 721 of human integrin $\beta_7$, that is, in the presence of the region of the amino acid residue positions 379 to 721 of human integrin $\beta_7$.

Example 9

Determination of Base Sequence of Antibody Molecule Variable Regions of MMG49 Antibody The subclass of the MMG49 antibody was confirmed using an Isotyping kit (Roche), and was confirmed to be IgG2a subclass. Further, the base sequences and amino acid sequences of variable regions of the MMG49 antibody were determined.

A sequence determination method was performed using a Smarter RACE cDNA amplification kit (Clontech). That is, cDNAs generated from mRNAs derived from hybridomas MMG49 producing the MMG49 antibody were used as templates to amplify cDNA fragments of H-chain and κ-chain variable regions by a PCR reaction, and their base sequences were read. The read amino acid sequence and base sequence, and hypervariable regions (CDR1 to CDR3) of the H-chain variable region are shown in Tables 3 and 4 below.

The read amino acid sequence and base sequence, and hypervariable regions (CDR1 to CDR3) of the L-chain (κ-chain) variable region are also shown in Tables 3 and 4 below.

Figure 14:
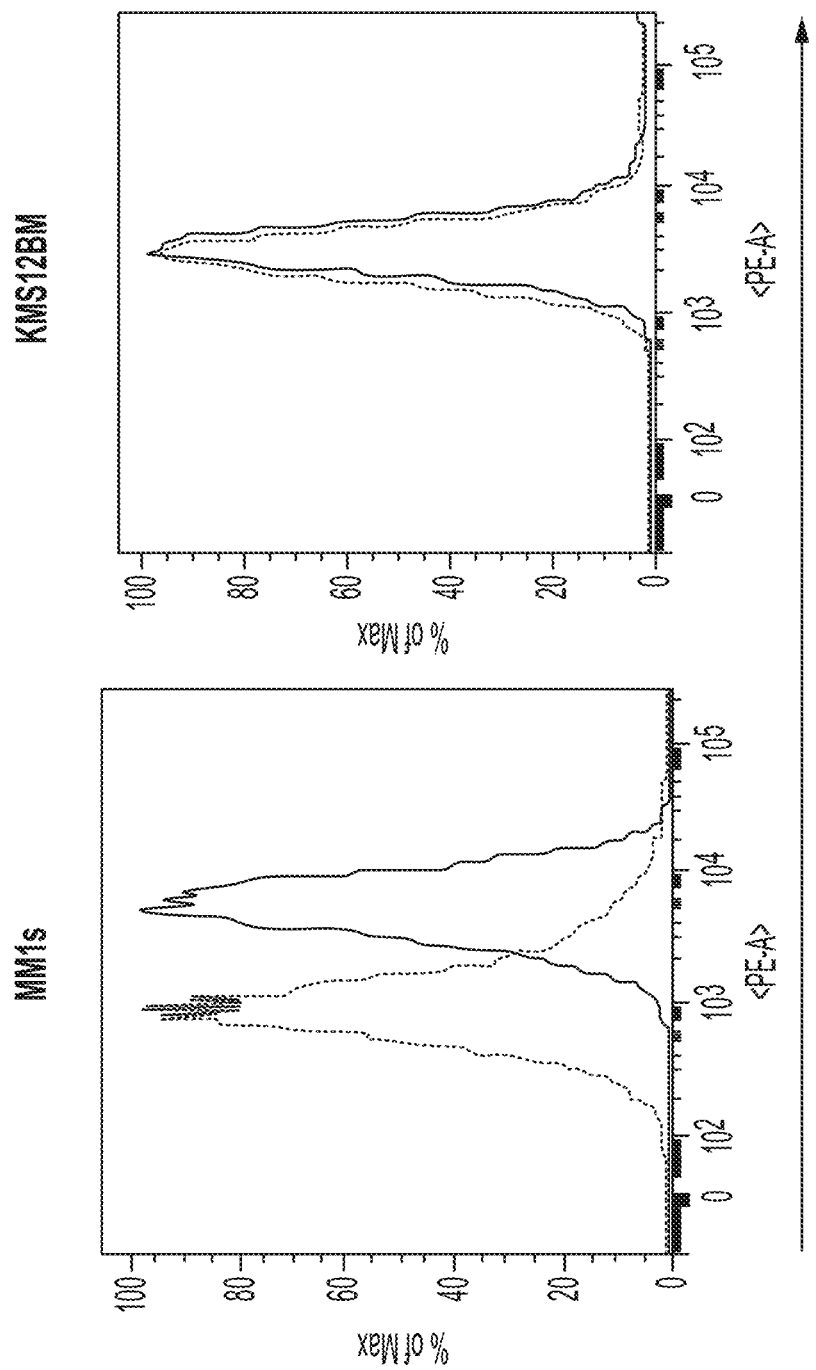
FIG. 14 is graphs showing results obtained by staining MM1s cells and KMS12BM cells with a chimerized MMG49 antibody generated by linking variable regions of the MMG49 antibody to a human IgG4 antibody constant domain.

In order to confirm the specificity of the isolated variable region sequences of the MMG49 antibody, variable region sequence cDNAs were bound to a human IgG4 constant domain and human IgL κ-chain constant domain sequence to generate a chimerized antibody. Specifically, each variable region sequence was inserted into pFuse-CH-Ig-hG4 or pFuse-CL-Ig-hk (invivogen) using In-Fusion cloning kit (Takara). After that, the resultant was introduced into Free-Style CHO-S cells (Invitrogen), and a chimerized antibody secreted into the culture supernatant thereof was recovered. Next, MM1s cells to which the MMG49 antibody bound and KMS12BM cells to which the MMG49 antibody did not bind were incubated in a buffer supplemented with MMG49-hIgG4, and were washed. After that, biotinylated anti-human IgG (Rockland) was added as a secondary antibody, and the cells were washed again, and then stained by adding streptavidin-PE (Biolegend), followed by FACS analysis. As a result, MMG49-hIgG4 showed a staining pattern similar to that of the original MMG49 antibody, suggesting that the obtained variable region sequences were correct (FIG. 14).

TABLE 3

<Amino acid sequences of MMG49>

| | | |
|---|---|---|
| HeavyCDR1 | (SEQ ID NO: 1) | GYTFSSYW |
| chainCDR2 | (SEQ ID NO: 2) | MLPGSGSS |
| CDR3 | (SEQ ID NO: 3) | ARGDGNYWYFDV |
| Variable region (SEQ ID NO: 4) | | MEWTWVFLFLLSVTAGVHSQVQLQQS GAELMKPGASVKISCKASGYTFSSYW IEWVKQRPGHGLEWIGEMLPGSGSSN YNEKFKGKATFTADTSSNTAYMQLSS LTSEDSAVYYCARGDGNYWYFDVWGA G |

TABLE 3 -continued

<Amino acid sequences of MMG49>

| | | |
|---|---|---|
| LightCDR1 | (SEQ ID NO: 6) | SSVGY |
| chain CDR2 | (SEQ ID NO: 7) | ATS |
| CDR3 | (SEQ ID NO: 8) | QQWSSDPPT |
| Variable region | | MDFQVQIFSFLLISASVIMSRGQIVL |
| (SEQ ID NO: 9) | | SQSPAILSASPGEKVTMTCRASSSVG |
| | | YMHWFQQKPGSSPKPWIYATSNLASG |
| | | VPARFSGSESGTSYSLTISRVEAEDA |
| | | ATYYCQQWSSDPPTFGGGTKLEIK |

TABLE 4

<Base sequences of MMG49>

| | | | |
|---|---|---|---|
| Heavy | CDR1 | (SEQ ID NO: 11) | GGCTACACATTCAGTAGCTACTGG |
| chain | CDR2 | (SEQ ID NO: 12) | ATGTTACCTGGAAGTGGTAGTTCT |
| | CDR3 | (SEQ ID NO: 13) | GCAAGGGGGGATGGTAACTACTGGTACTTCGATGTC |
| | Variable region | | ATGGAATGGACCTGGGTCTTTCTCTTCCTCCTGTCA |
| | (SEQ ID NO: 14) | | GTAACTGCAGGTGTCCACTCCCAGGTTCAGCTGCAG |
| | | | CAGTCTGGAGCTGAGCTGATGAAGCCTGGGGCCTCA |
| | | | GTGAAGATATCCTGCAAGGCTTCTGGCTACACATTC |
| | | | AGTAGCTACTGGATAGAGTGGGTAAAGCAGAGGCCT |
| | | | GGACATGGCCTTGAGTGGATTGGAGAGATGTTACCT |
| | | | GGAAGTGGTAGTTCTAACTACAATGAGAAGTTCAAG |
| | | | GGCAAGGCCACATTCACTGCAGATACATCCTCCAAC |
| | | | ACAGCCTACATGCAACTCAGCAGCCTGACATCTGAG |
| | | | GACTCTGCCGTCTATTACTGTGCAAGGGGGGATGGT |
| | | | AACTACTGGTACTTCGATGTCTGGGGCGCAGGG |
| Light | CDR1 | (SEQ ID NO: 16) | TCAAGTGTAGGTTAC |
| chain | CDR2 | (SEQ ID NO: 17) | GCCACATCC |
| | CDR3 | (SEQ ID NO: 18) | CAGCAGTGGAGTAGTGACCCACCGACG |
| | Variable region | | ATGGATTTTCAAGTGCAGATTTTCAGCTTCCTGCTA |
| | (SEQ ID NO: 19) | | ATCAGTGCTTCAGTCATAATGTCCAGAGGACAAATT |
| | | | GTTCTCTCCCAGTCTCCAGCAATCCTGTCTGCATCT |
| | | | CCAGGGGAGAAGGTCACAATGACTTGCAGGGCCAGC |
| | | | TCAAGTGTAGGTTACATGCACTGGTTCCAGCAGAAG |
| | | | CCAGGATCCTCCCCCAAACCCTGGATTTATGCCACA |
| | | | TCCAACCTGGCTTCTGGAGTCCCTGCTCGCTTCAGT |
| | | | GGCAGTGAGTCTGGGACCTCTTACTCTCTCACAATC |
| | | | AGCAGAGTGGAGGCTGAAGATGCTGCCACTTATTAC |
| | | | TGCCAGCAGTGGAGTAGTGACCCACCGACGTTCGGT |
| | | | GGAGGCACCAAGCTGGAAATCAAA |

TABLE 5

| No. | Primer name | Base sequence |
|---|---|---|
| 23 | 49_car_vk-s5 | gaattccaccatggatttttcaagtgcagatt |
| 24 | 49_car_vk-as6 | gccggaaccgctagtggagccccgtttgatt tccagcttggt |
| 25 | 593_car_vk_as4 | gctgccttctccgctgccaggtttgccggaa ccgctagtggagcc |

Example 10

Generation of Chimeric Antigen Receptor T-cells using Antibody Molecule Variable Regions of MMG49 Antibody Chimeric antigen receptor T-cells (hereinafter referred to as MMG49 antibody-derived chimeric antigen receptor T-cells) were generated using the MMG49 antibody molecule variable region sequences by the following procedure with reference to Non Patent Literatures 2 to 4 and the like.

(1) Cloning of CD28 and CD3z:

RNAs were collected from Jurkat cells through use of Trizol (Invitrogen), and cDNAs were generated using a Superscript III cDNA synthesis kit (Invitrogen). Then, the cDNAs were used as templates to amplify cDNAs of CD28 and CD3z by PCR, each of which was cloned using a TA cloning kit (Invitrogen), and their base sequences were confirmed by sequencing.

Figure 15:
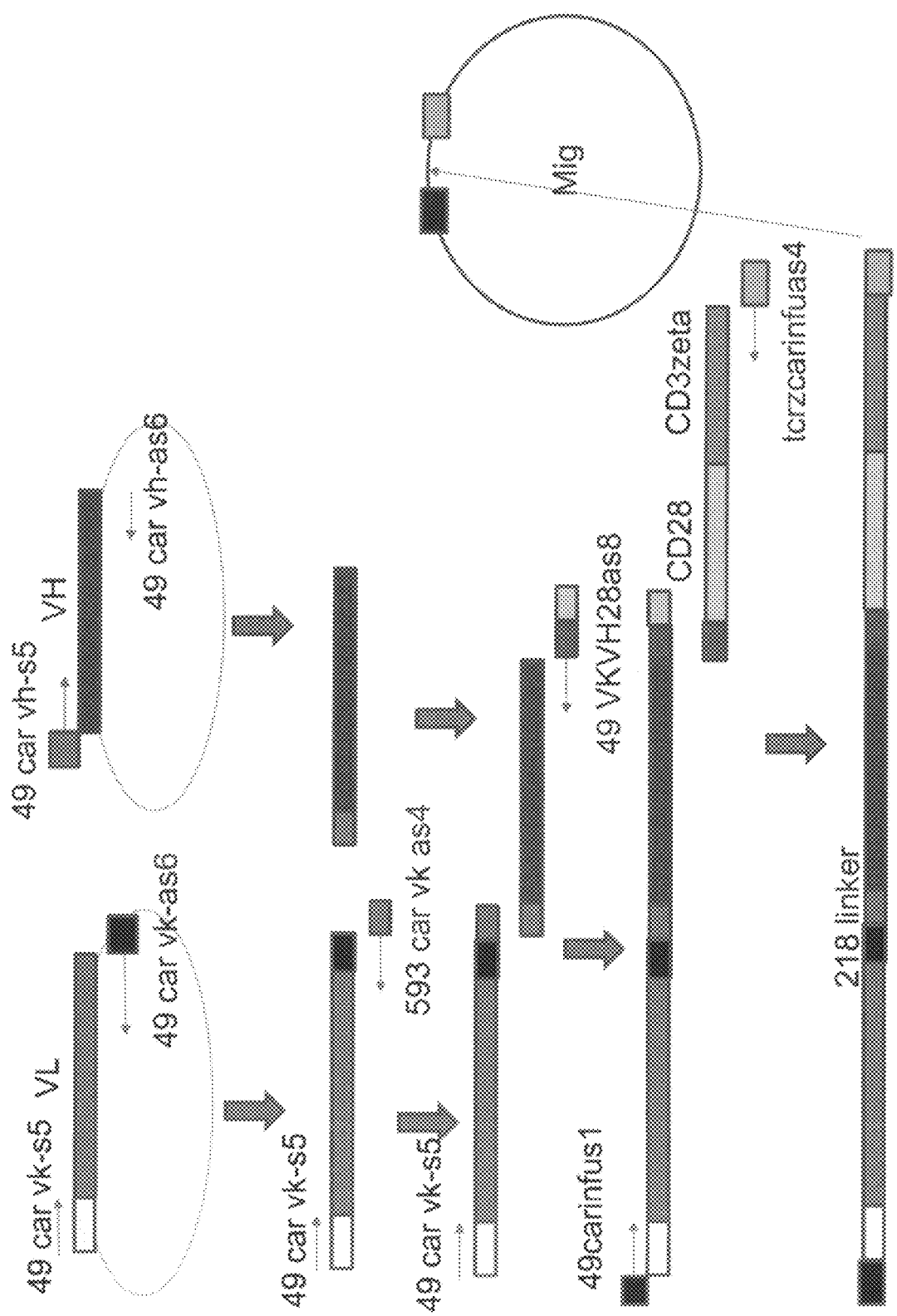
FIG. 15 is a scheme illustrating a method of generating a CAR construct using variable regions of the MMG49 antibody.

(2) Binding of Four Fragments, i.e., MMG49 antibody-derived VL/VH, and CD28/CD3z:

Through use of an overlapping PCR method, respective gene fragments of the MMG49 antibody-derived VL region and VH region, and the CD28 and CD3z cloned above were bound to each other to generate chimeric cDNA. A procedure therefor and primers used are illustrated in FIG. 15. The base sequences of the primers used are shown in Table 5 below.

TABLE 5 -continued

| No. | Primer name | Base sequence |
|---|---|---|
| 26 | 49_car_vh-s5 | aaacctggcagcggagaaggcagccaggttc agctgcagcagtc |
| 27 | 49_car_vh-as6 | tgaggagacggtgaccgtgg |
| 28 | 49_VKVH28as8 | atacataacttcaattgcggccgctgaggag acggtgaccgtgg |
| 29 | 49carinfus1 | ctaggcgccggaattccaccatggatttttc |
| 30 | tcrzcarinfuas4 | aatgtcgacctcgagtggctgttagcgag |

The bound chimeric cDNA was cloned using a Zeroblunt PCR cloning kit (Invitrogen), and then sequenced to confirm its base sequence. In addition, an amino acid sequence (SEQ ID NO: 21) confirmed on the basis of the confirmed base sequence and the base sequence (SEQ ID NO: 22) are shown in the sequence listing. The amino acid sequence set forth in SEQ ID NO: 21 is one obtained by conversion into an amino acid sequence from the start codon (atg) immediately following the Kozak sequence (gaattccacc) shown above in SEQ ID NO: 23, which was excluded.

(3) Insertion into Expression Vector:

Subsequently, the chimeric cDNA bound in (2) was cleaved with two restriction enzymes EcoRI/SalI, and inserted into an MSCV-ires-GFP vector.

The MMG49 antibody-derived chimeric antigen receptor cDNA retrovirus vector generated by the foregoing was introduced into 293T cells together with a gag/pol and VSV-G envelope expression vector through use of lipofectamine 2000 (invitrogen), to thereby generate a retrovirus. After 48 hours from the gene introduction, a supernatant was recovered and used as a virus solution.

(4) Introduction into T-Cells:

Subsequently, cDNA of an MMG49 antibody-derived chimeric antigen receptor was introduced into human T-cells as described below.

Figure 16:
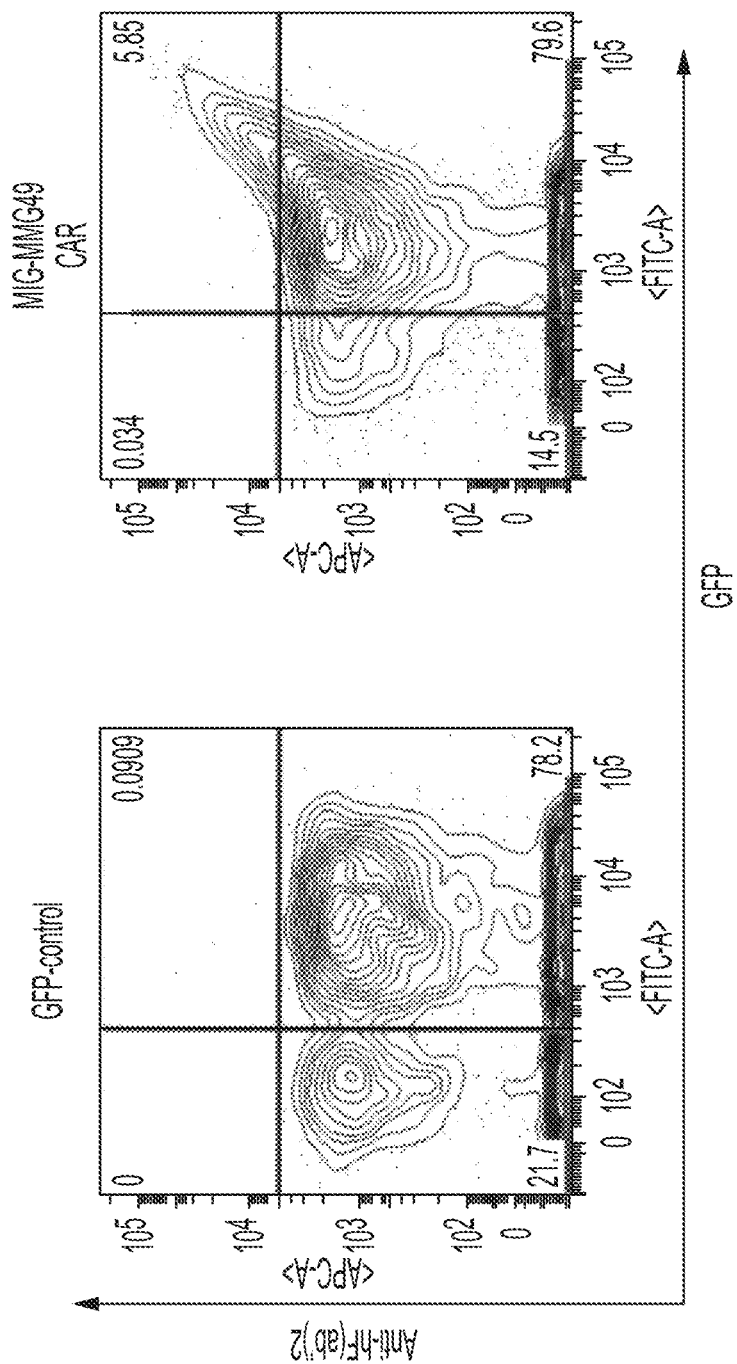
FIG. 16 is graphs showing results obtained by staining T-cells caused to express the CAR construct using variable regions of the MMG49 antibody with a PE-anti-human F(ab')$_2$ antibody.

First, human peripheral blood mononuclear cells were added to a 48-well plate coated with an anti-CD3 antibody (eBioscience) and cultured for 72 hours. X-VIVO15 (Lonza) supplemented with 10% human AB serum and IL-2 (175 IU/L) was used as a culture medium, and the peripheral blood mononuclear cells were stimulated. After that, the virus solution generated above was added to a 48-well plate coated with Retronectin (Takara), and the virus was adsorbed to Retronectin by centrifugation at 1,700×g for 120 minutes. After that, the peripheral blood mononuclear cells (including T-cells) after the stimulation were added, and the gene was introduced thereinto. After that, culture was continued in the above-mentioned medium to amplify MMG49 antibody-derived chimeric antigen receptor T-cells, which were used in the following investigation. The T-cells caused to express a CAR construct using variable regions of the MMG49 antibody were stained using a PE-anti-human F(ab')$_2$ antibody (Jackson Laboratory), and as a result, the expression of human F(ab')$_2$ was detected in proportion to the expression of GFP indicating the introduction of the construct (FIG. 16). That is, it was confirmed that the introduced CAR was expressed on a cell surface.

Example 11

Figure 17:
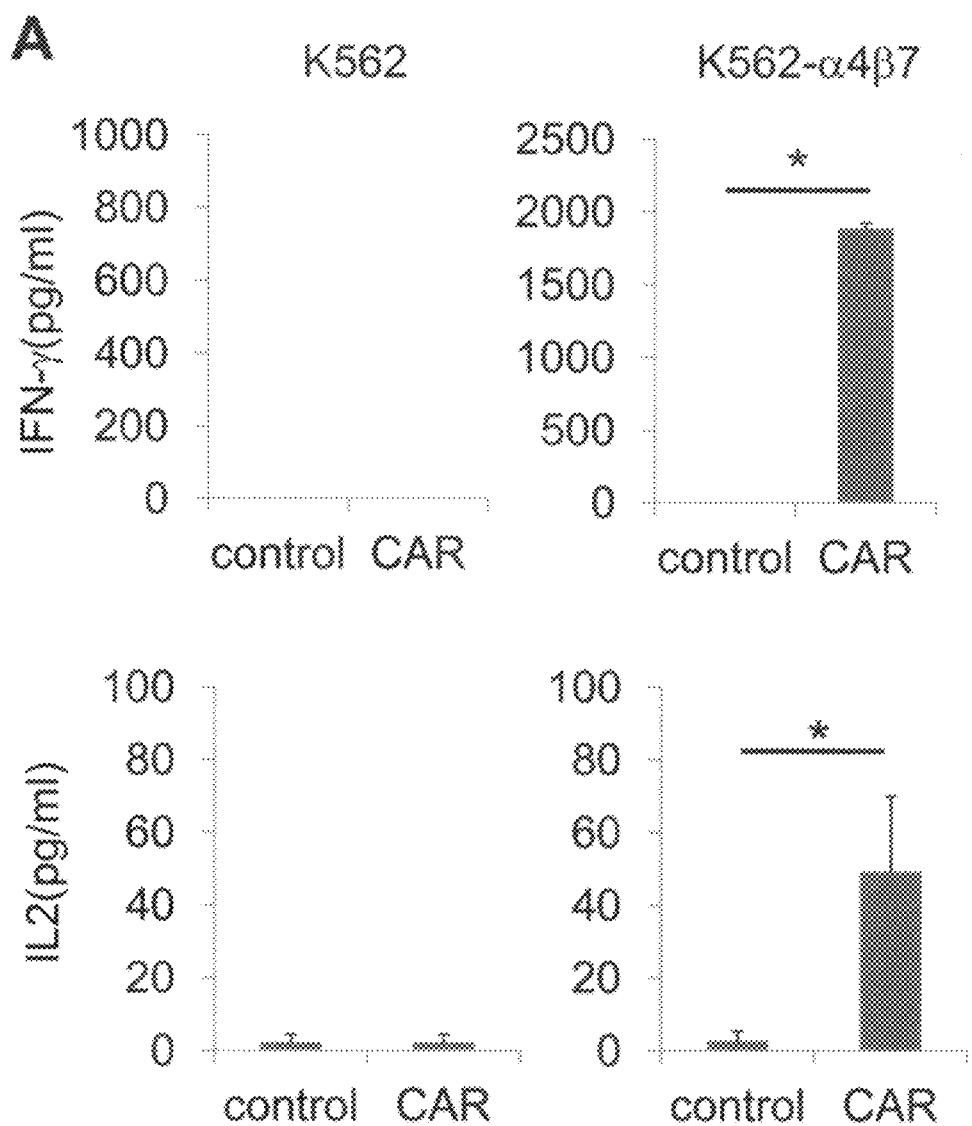
FIG. 17 is graphs showing results obtained in Example 11 by quantitatively determining, by ELISA, the amounts of IFN-γ and IL2 produced through coculture of MMG49 antibody-derived CAR-T cells or T-cells having introduced therein GFP (control) with K562 cells expressing no integrin $\beta_7$ or K562 cells caused to forcibly express integrin $\alpha_4\beta_7$. *: $p<0.05$.

Analysis of Recognition of ITGB7-Expressing Tumor Cells by MMG49 Antibody-Derived Chimeric Antigen Receptor T-Cells and Cytotoxic Activity Thereof The MMG49 antibody-derived chimeric antigen receptor T-cells generated by the above-mentioned method or control T-cells having introduced therein only GFP were cocultured with K562 cells expressing no integrin $\beta_7$ or K562 cells caused to forcibly express integrin $\alpha_4\beta_7$, and the amount of a produced cytokine was quantitatively determined. Specifically, $1\times10^5$ each of the T-cells and the target cells were added to a 96-well plate. After 24 hours, a supernatant was recovered, and the amount of production of IFN-γ was measured by ELISA. The measurement was performed using a Quantikine kit (R&D). As a result, only in the coculture of the K562 cells caused to forcibly express integrin $\alpha_4\beta_7$ with the MMG49 antibody-derived chimeric antigen receptor T-cells, higher production of IFN-γ and IL2 than in the control (T-cells obtained by similarly culturing stimulated peripheral blood mononuclear cells having introduced therein a GFP expression vector) was observed (FIG. 17).

Figure 18:
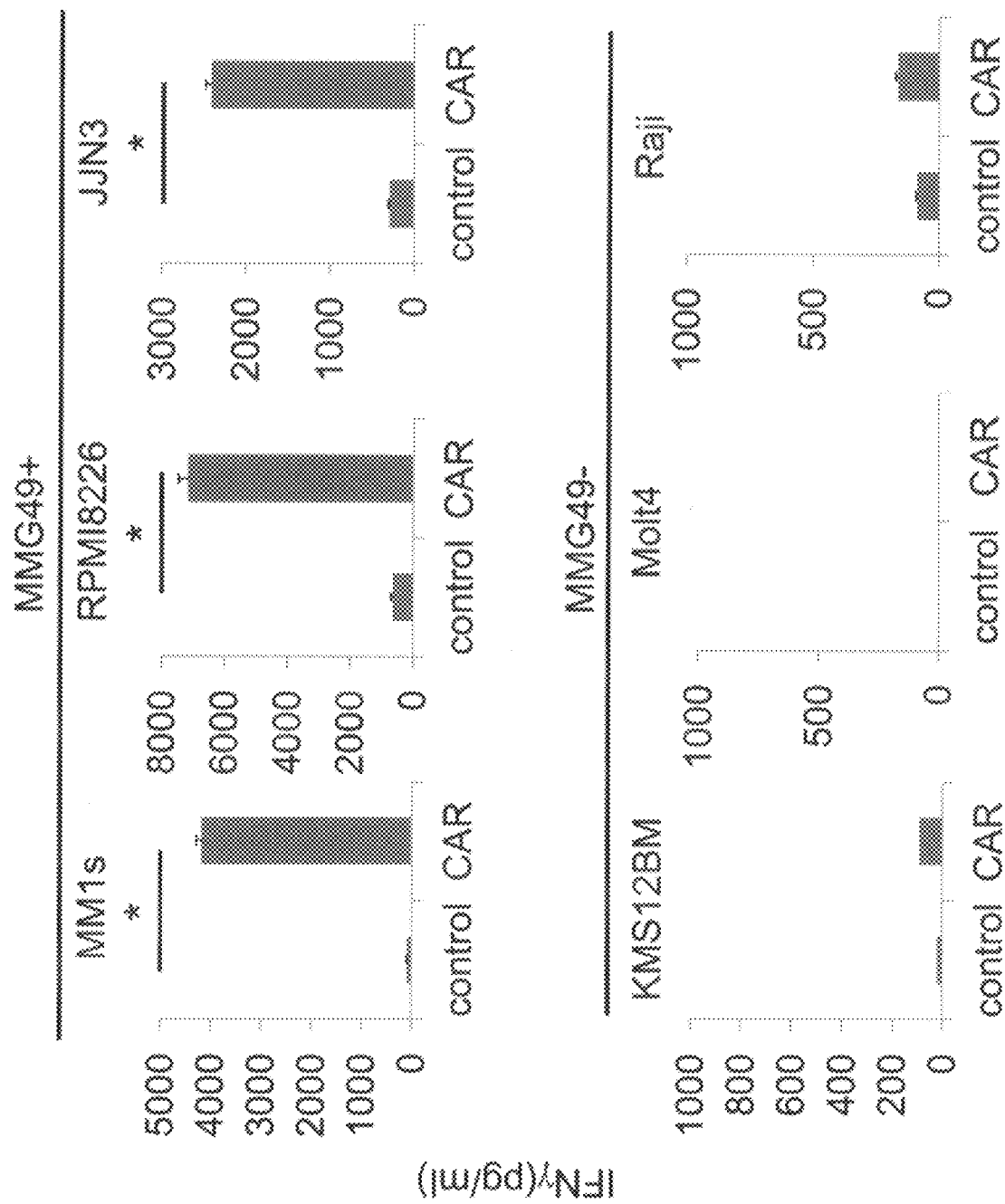
FIG. 18 is graphs showing results obtained in Example 11 by quantitatively determining, by ELISA, the amount of IFN-γ produced through coculture of MMG49 antibody-derived CAR-T cells or T-cells having introduced therein GFP (control) with MMG49 antigen-expressing cells or non-expressing cells.
Figure 19:
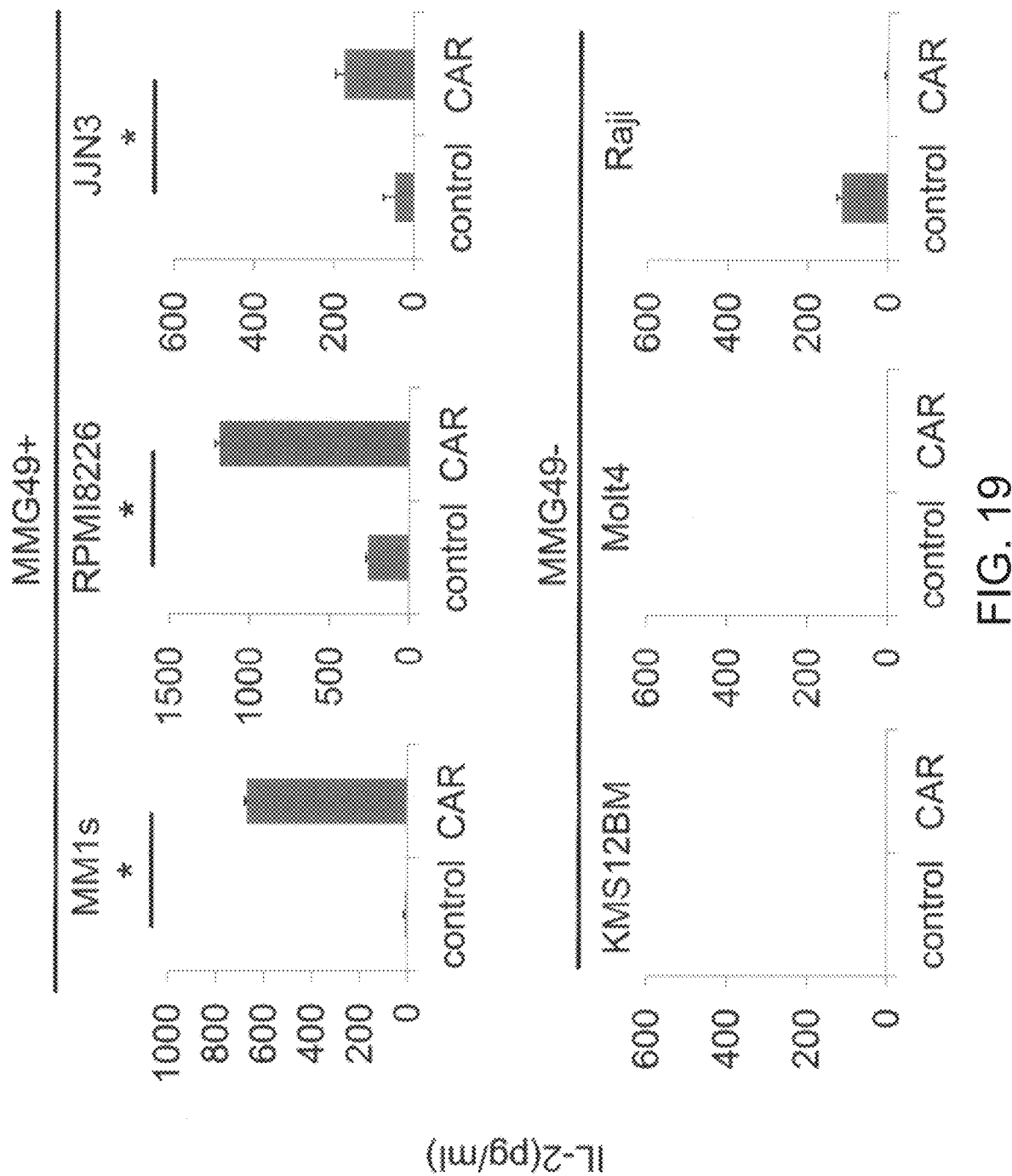
FIG. 19 is graphs showing results obtained in Example 11 by quantitatively determining, by ELISA, the amount of IL2 produced through coculture of MMG49 antibody-derived CAR-T cells or T-cells having introduced therein GFP (control) with MMG49 antigen-expressing cells or non-expressing cells.

Next, the MMG49 antibody-derived chimeric antigen receptor T-cells or control T-cells having introduced therein only GFP were cocultured with myeloma cell lines to which the MMG49 antibody bound (MM.1s cells, RPMI8226 cells, and JJN3 cells) or cells to which the MMG49 antibody did not bind (KMS12BM, Molt4, and Raji cells), and the amount of a produced cytokine was similarly quantitatively determined. As a result, only when the MM.1s, RPMI8226 cells, and JJN3 cells, which were cells to which the MMG49 antibody bound, were cocultured with the MMG49 antibody-derived chimeric antigen receptor T-cells, higher production of IFN-γ and IL2 than in the control (T-cells obtained by similarly culturing stimulated peripheral blood mononuclear cells having introduced therein a GFP expression vector) was observed (FIG. 18 and FIG. 19). The results show that the MMG49 antibody-derived chimeric antigen receptor T-cells are activated by recognizing an antigen recognized by the MMG49 antibody (sometimes referred to as MMG49 antigen).

Further, whether the MMG49 antibody-derived chimeric antigen receptor T-cells damaged a myeloma cell line was investigated by $^{51}$Cr cytotoxicity assay. First, K562 cells expressing no integrin $\beta_7$ or K562 cells caused to forcibly express integrin $\alpha_4\beta_7$ to be used as target cells were cultured in RPMI1640 medium supplemented with 10% FCS, and were prepared so that the number of cells was from $0.5\times10^4$ to $1.0\times10^4$.

An appropriate amount of Na$_2$$^{51}$CrO$_4$ was added thereto and allowed to react therewith at 37° C. for 2 hours to label the cells with $^{51}$Cr, and the resultant cells were washed and then used as target cells. The target cells were mixed with MMG49 antibody-derived chimeric antigen receptor T-cells suspended in RPMI1640 medium supplemented with fetal bovine serum, and the cells were cocultured for 4 hours.

After that, $^{51}$Cr released into the supernatant was measured with a γ-counter. A cell damage percentage (%) was determined on the basis of the following expression (1).

$$(A-B)/(C-D)\times 100 \tag{1}$$

A: Amount of $^{51}$Cr released from cells used in experiment

B: Spontaneous $^{51}$Cr release amount under antibody-free state

C: Maximum $^{51}$Cr release amount with addition of 1% Triton X-100

D: Spontaneous $^{51}$Cr release amount under antibody-free state.

Figure 20:
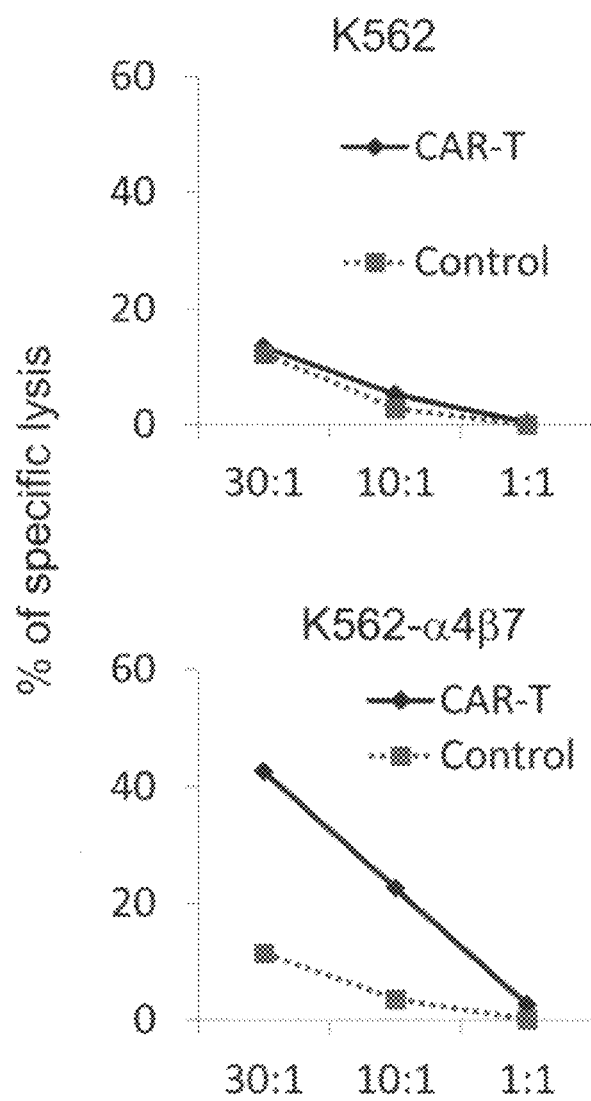
FIG. 20 is graphs showing results obtained in Example 11 by measuring, by $^{51}Cr$ killing assay, the degree of cell damage caused by MMG49 antibody-derived CAR-T cells or T-cells having introduced therein GFP (control) with respect to K562 cells expressing no integrin $\beta_7$ or K562 cells caused to forcibly express integrin $\alpha_4\beta_7$. The y-axis of each of the graphs in FIG. 20 represents a cell damage percentage (%).

As a result, in the K562 cells caused to forcibly express integrin $\alpha_4\beta_7$ to which the MMG49 antibody bound, higher cell damage caused by the MMG49 antibody-derived chimeric antigen receptor T-cells than in the T-cells expressing only GFP serving as a control was observed (FIG. 20).

Figure 21:
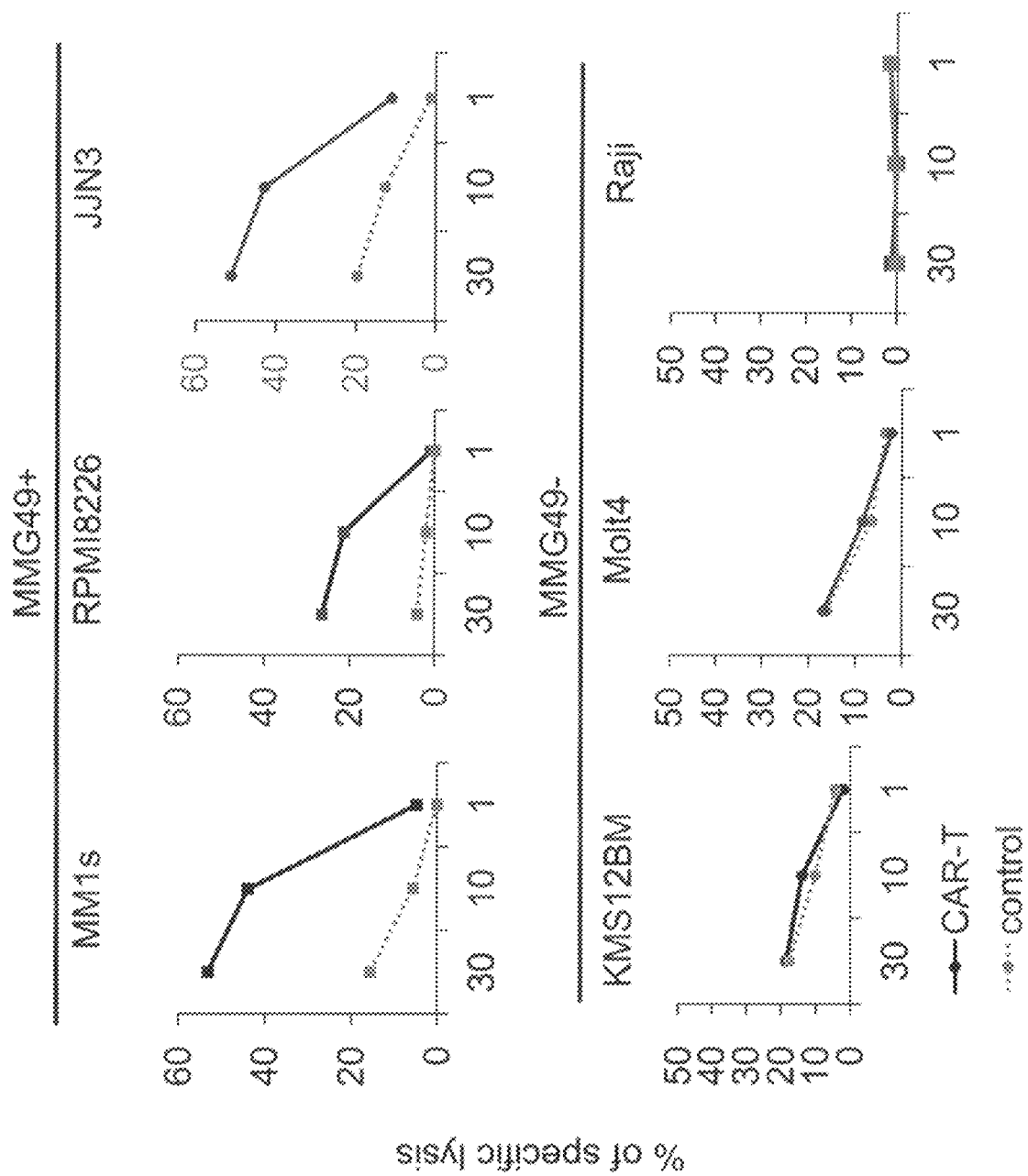
FIG. 21 is graphs showing results obtained in Example 11 by measuring, by $^{51}Cr$ killing assay, the degree of cell damage caused by MMG49 antibody-derived CAR-T cells or T-cells having introduced therein GFP (control) with respect to MMG49 antigen-expressing cells or non-expressing cells.

Next, the MMG49 antibody-derived chimeric antigen receptor T-cells or control T-cells having introduced therein only GFP were cocultured with myeloma cell lines to which the MMG49 antibody bound (MM1s cells, RPMI8226 cells, and JJN3 cells) or cells to which the MMG49 antibody did not bind (KMS12BM, Molt4, and Raji cells), and a similar investigation was performed. As a result, only in the K562 cells caused to forcibly express integrin $\alpha_4\beta_7$ to which the MMG49 antibody bound, higher cell damage caused by the MMG49 antibody-derived chimeric antigen receptor T-cells than in the T-cells expressing only GFP serving as a control was observed (FIG. 21).

The above-mentioned results show that the MMG49 antibody-derived chimeric antigen receptor T-cells can specifically damage cells expressing an antigen to be recognized by the MMG49 antibody.

Example 12

Analysis of Myeloma Cell-Eliminating Ability Exhibited by MMG49 Antibody-Derived Chimeric Antigen Receptor T-Cells in Vivo A therapeutic effect on multiple myeloma was investigated in vivo using the MMG49 antibody-derived chimeric antigen receptor T-cells.

Figure 22:
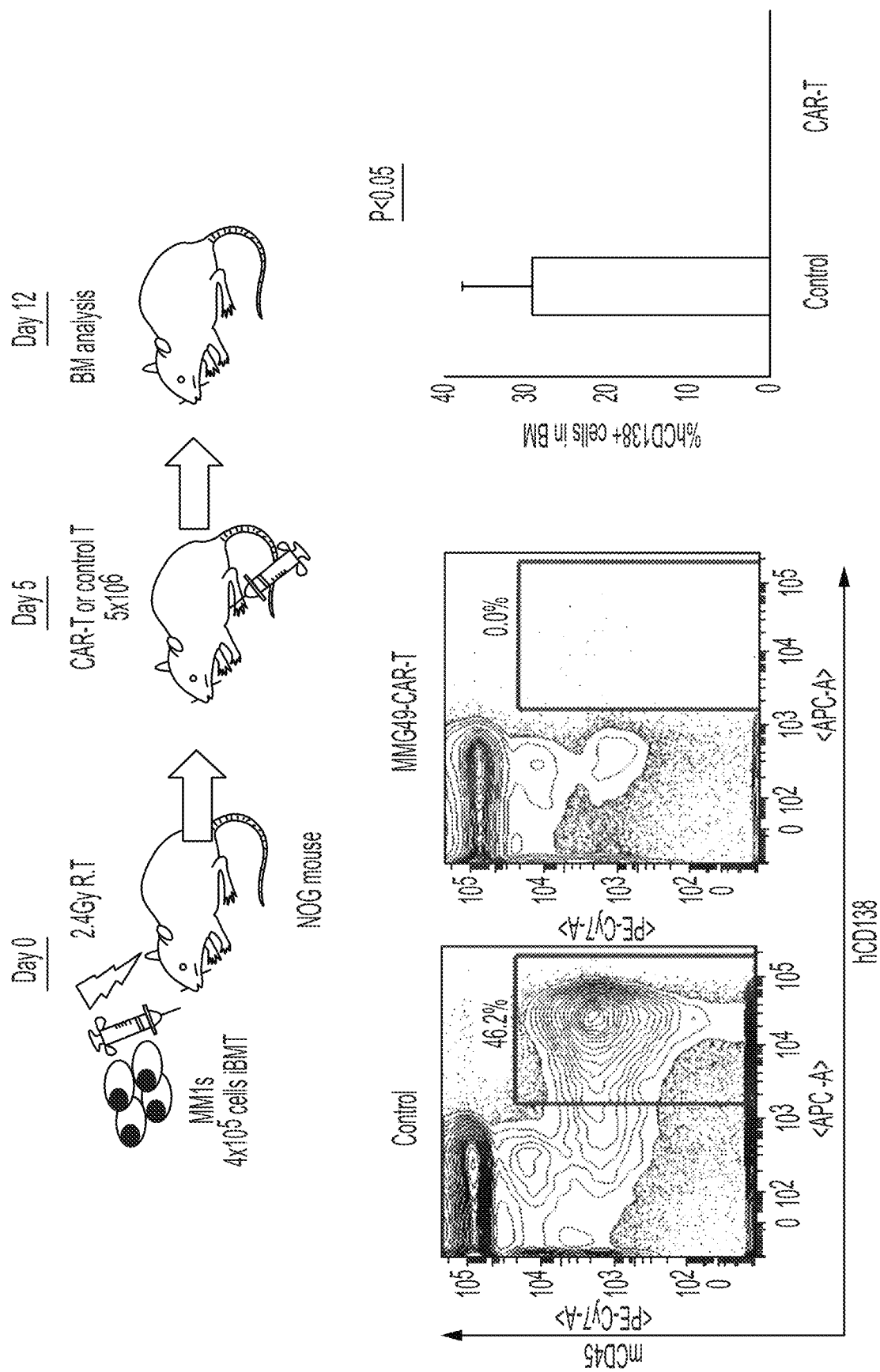
FIG. 22 is a diagram and graphs for illustrating and showing the design of a therapeutic experiment for a myeloma cell line MM1s engrafted in the bone marrow of an NOG mouse and results thereof in Example 12. Bone marrow cells after 1 week from the transfer of MMG49 antibody-derived CAR-T cells or T-cells having introduced therein GFP (control) were collected and analyzed by FACS. MM1s cells can be identified as human CD138$^+$ cells. In an MMG49 antibody-derived CAR-T cell-administered group, MM1s cells in the bone marrow have almost completely disappeared.

Myeloma cell line MM1s cells ($4 \times 10^5$ cells) were transplanted into the bone marrow of NOG mice subjected to radiation exposure at 2.4 Gy. After 5 days, the mice were grouped into an MMG49 antibody-derived chimeric antigen receptor T-cell-administered group and a control T-cell-administered group, and each group was intravenously administered with $5 \times 10^6$ cells per mouse. After 7 days from the administration, the bone marrow was analyzed. As a result, marked growth of myeloma cells was clearly observed in all mice of the control T-cell-administered group, whereas the tumor had almost completely disappeared in the MMG49 antibody-derived chimeric antigen receptor I-cell-administered group. The results show that the administration of the MMG49 antibody-derived chimeric antigen receptor T-cells has an ability to eliminate a tumor expressing the MMG49 antigen even in vivo (FIG. 22).

Further, a therapeutic effect on multiple myeloma was investigated in vivo using a myeloma-systemically seeded model.

Figure 23A:
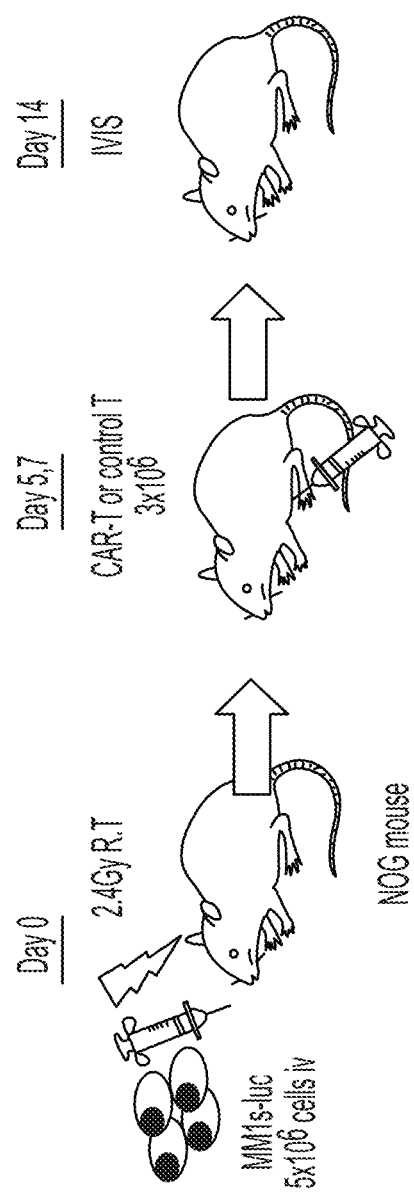
FIGS. 23A and 23B are a diagram, images, and a graph for illustrating and showing the design of a therapeutic experiment for the myeloma cell line MM1s systemically engrafted to an NOG mouse and results thereof in Example 12. The amounts of myeloma cells before and after the transfer of MMG49 antibody-derived CAR-T cells or T-cells having introduced therein GFP (control) were evaluated by fluorescence intensity measurement based on IVIS imaging. In an MMG49 antibody-derived CAR-T cell-administered group, MM1s cells in the bone marrow have almost completely disappeared.
Figure 23B:
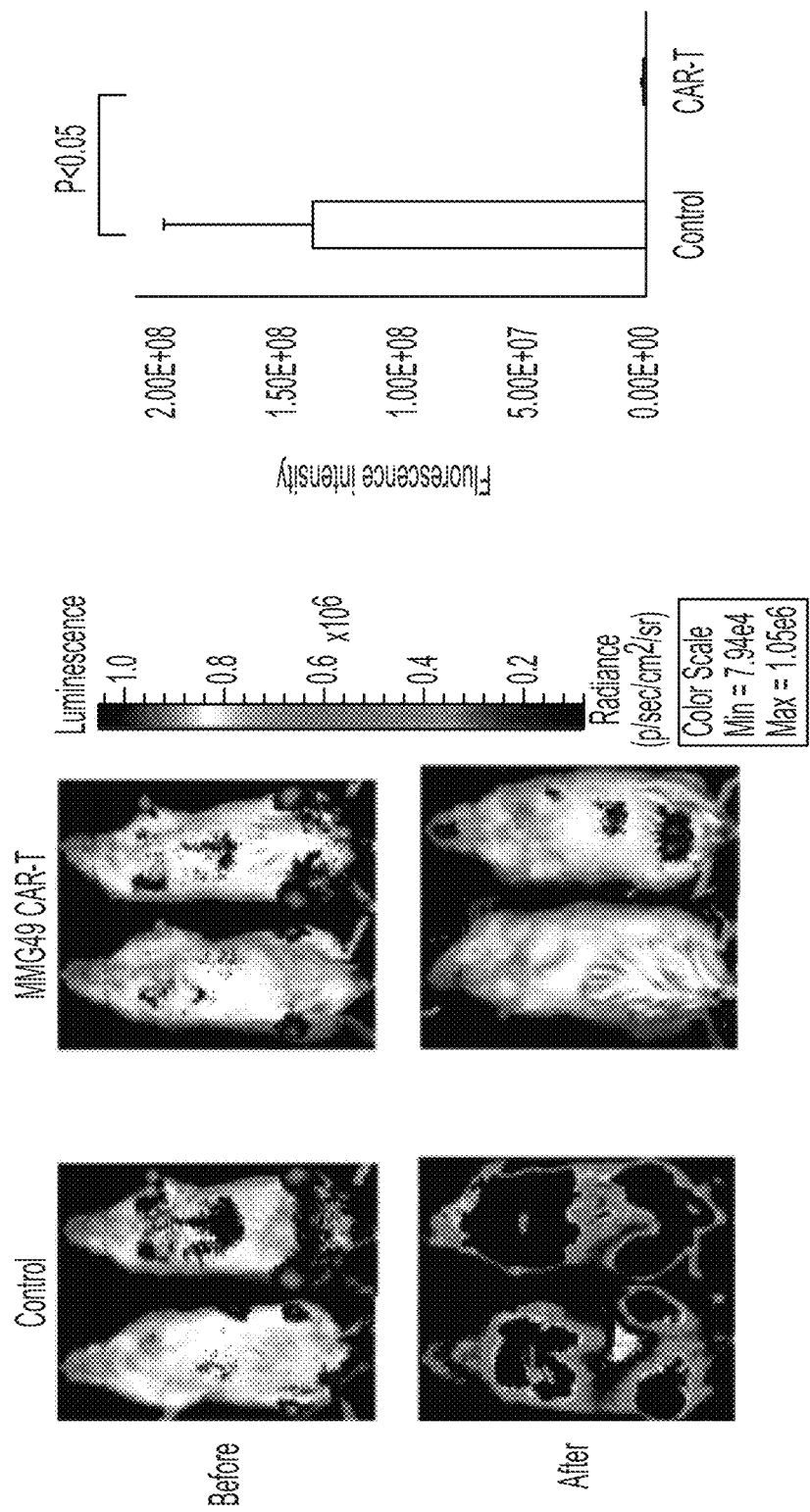

Myeloma cell line MM1s cells ($5 \times 10^6$ cells) having introduced therein luciferase gene were intravenously transplanted into NOG mice subjected to radiation exposure at 2.4 Gy. After 5 days from the transplantation, the degree of engraftment of the tumor cells was measured using an IVIS imaging system (PerkinElmer). After that, the mice were grouped into an MMG49 antibody-derived chimeric antigen receptor T-cell-administered group and a control T-cell-administered group, and each group was intravenously administered with $3 \times 10^6$ cells per mouse 5 days and 7 days after the transplantation. After 7 days from the second T-cell administration, a tumor volume was measured again using the IVIS imaging system. As a result, marked growth of myeloma cells was clearly observed in all mice of the control T-cell-administered group, whereas the tumor had almost completely disappeared in the MMG49 antibody-derived chimeric antigen receptor T-cell-administered group (FIG. 23). The results show that the administration of the MMG49 antibody-derived chimeric antigen receptor T-cells has an ability to eliminate a tumor expressing the MMG49 antigen even in vivo.

Example 13

Figure 25:
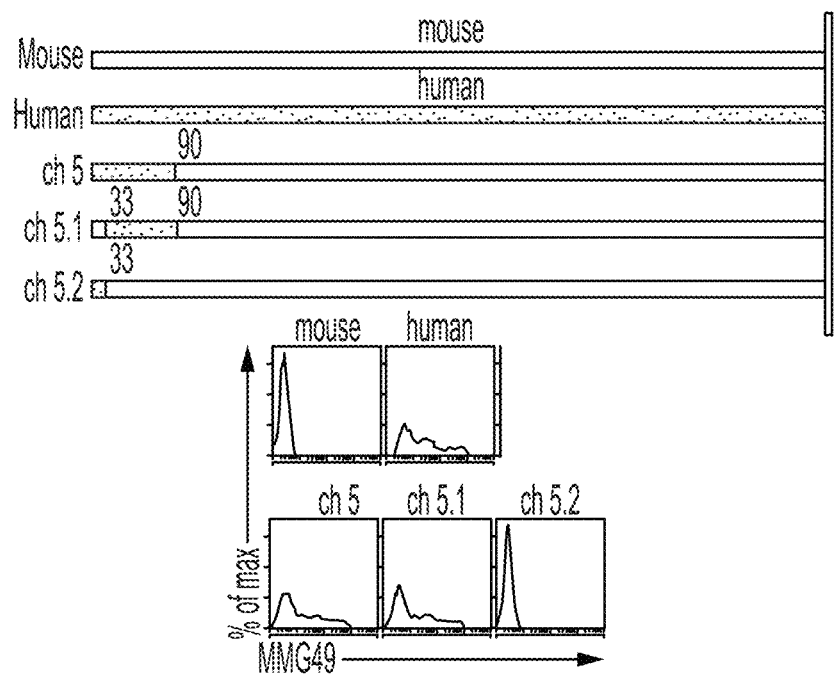
FIG. 25 is a diagram and graphs for illustrating and showing the construction of human/mouse chimeric integrin $\beta_7$ proteins and the presence or absence of the binding of the MMG49 antibody to 293T cells caused to transiently express the proteins in Example 13.

For the epitope of the MMG49 antibody, an experiment for investigating, in more detail, the results of the investigation in Example 8 was performed. Vectors for expressing three kinds of human/mouse chimeric integrin $\beta_7$ protein as illustrated in FIG. 25 were generated, and each of the expression vectors was introduced into 293T cells by a lipofection method. After 48 hours, the presence or absence of the binding of the MMG49 antibody was analyzed by FACS.

As a result, it was revealed that the MMG49 antibody strongly bound to a chimeric integrin $\beta_7$ protein (ch5.1 in FIG. 25) in which regions of the amino acid residue positions 1 to 32 and positions 91 to 798 of integrin $\beta_7$ protein were of mouse origin, and the rest (region of the amino acid residue positions 33 to 90) had a sequence of human origin in almost the same manner as in the case of the integrin $\beta_7$ protein entirely of human origin (#4927 in FIG. 11) (FIG. 25).

Thus, it was strongly suggested that the epitope of the MMG49 antibody was included in the amino acid residues at positions 33 to 90 of the human integrin $\beta_7$ protein.

Example 14

Figure 26:
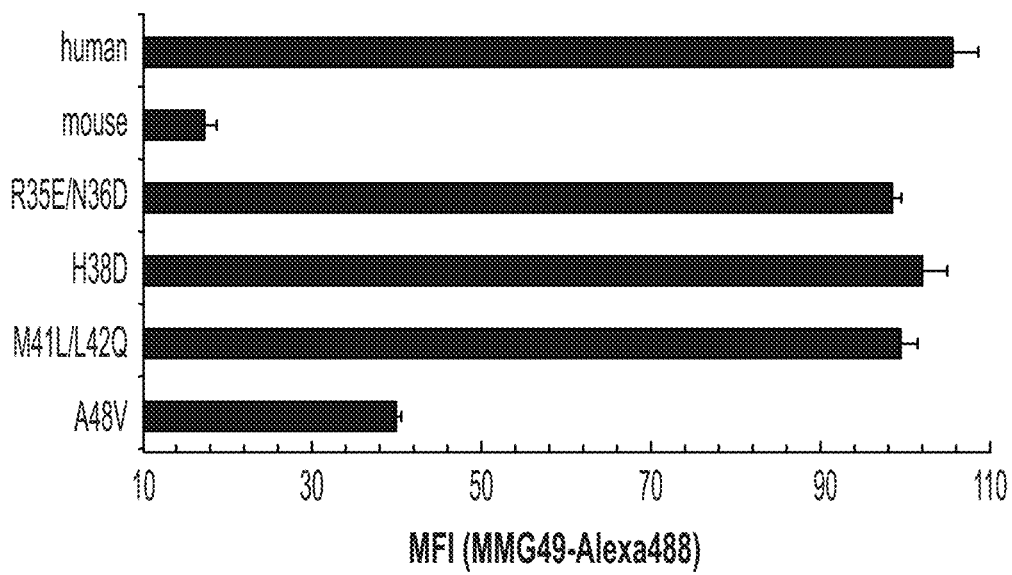
FIG. 26 is a graph for showing results of an experiment for investigating an epitope of the MMG49 antibody in Example 14. MFI on the axis of abscissa represents binding strength to the MMG49 antibody, and a higher numerical value indicates a higher avidity.

Vectors expressing the human integrin $\beta_7$, the mouse integrin $\beta_7$, and various variants obtained by mutating only one or two amino acids of the human integrin $\beta_7$ into an amino acid sequence of mouse origin (R35E/N36D, H38D, M41L/L42Q, and A48V) were introduced into 293T cells by a lipofection method, and an experiment was performed in the same manner as in Example 8 thereafter. As a result, as shown in FIG. 26, it was revealed that only the A48V variant had a remarkably reduced avidity for the MMG49 antibody as compared to the human integrin $\beta_7$, and had a numerical value close to that of the mouse integrin $\beta_7$. The results revealed that the amino acid residue at position 48 of the human integrin $\beta_7$ was strongly related to the epitope of the MMG49 antibody, or included in the epitope of the MMG49 antibody.

Base sequences and amino acid sequences described herein are shown below.

---

The invention claimed is:

1. An anti-integrin beta 7 antibody comprising:
    a heavy chain variable region including
        heavy-chain CDR1 having the amino acid sequence of SEQ ID NO: 1,
        heavy-chain CDR2 having the amino acid sequence of SEQ ID NO: 2, and
        heavy-chain CDR3 having the amino acid sequence of SEQ ID NO: 3; and
    a light chain variable region including
        light-chain CDR1 having the amino acid sequence of SEQ ID NO: 6,
        light-chain CDR2 having the amino acid sequence of SEQ ID NO: 7, and
        light-chain CDR3 having the amino acid sequence of SEQ ID NO: 8.

2. The antibody of claim 1, wherein the heavy chain variable region comprises an amino acid sequence that is at least 90% identical to the amino acid sequence of SEQ ID NO: 4; and wherein the light chain variable region comprises an amino acid sequence that is at least 90% identical to the amino acid sequence of SEQ ID NO: 9.

3. The antibody of claim 2, wherein the heavy chain variable region comprises the amino acid sequence of SEQ ID NO: 4; and wherein the light chain variable region comprises the amino acid sequence of SEQ ID NO: 9.

4. The antibody of claim 1, wherein the antibody is Fv, scFv, a diabody, a triabody, a tetrabody, or a combination thereof.

5. The antibody of claim 1, wherein the antibody comprises a constant region.

6. The antibody of claim 1, wherein the antibody is a chimeric antibody.

7. The antibody of claim 1, wherein the antibody is a humanized antibody.

8. The antibody of claim 1, wherein the antibody is an immunoglobulin, Fab, F(ab')2, a minibody, scFv-Fc, or a combination thereof.

9. The antibody of claim 1, wherein the antibody is IgA, IgD, IgE, IgG, or IgM.

10. The antibody of claim 1, wherein the antibody is multispecific.

11. The antibody of claim 1, whose affinity for human integrin beta7 expressed on myeloma cells is higher than for human integrin beta7 expressed on normal cells.

12. A pharmaceutical composition comprising the antibody of claim 1.

* * * * *